United States Patent
Guttman et al.

(10) Patent No.: US 11,828,684 B2
(45) Date of Patent: Nov. 28, 2023

(54) DETECTION OF MOLECULAR ASSOCIATIONS

(71) Applicant: California Institute of Technology, Pasadena, CA (US)

(72) Inventors: Mitchell Guttman, Los Angeles, CA (US); Mario R. Blanco, Los Angeles, CA (US); Ward Walkup, IV, Lincoln, MA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 542 days.

(21) Appl. No.: 16/573,673

(22) Filed: Sep. 17, 2019

(65) Prior Publication Data

US 2020/0088729 A1    Mar. 19, 2020

Related U.S. Application Data

(60) Provisional application No. 62/732,413, filed on Sep. 17, 2018.

(51) Int. Cl.
*G01N 33/573* (2006.01)
*C12N 15/90* (2006.01)

(52) U.S. Cl.
CPC ......... *G01N 33/573* (2013.01); *C12N 15/907* (2013.01); *C12Y 201/01043* (2013.01)

(58) Field of Classification Search
CPC ............. G01N 33/573; G01N 33/6845; C12N 15/907; C12Y 201/01043
See application file for complete search history.

(56) References Cited

U.S. PATENT DOCUMENTS

| | | |
|---|---|---|
| 2010/0099200 A1 | 4/2010 | Nazabal et al. |
| 2013/0021725 A1 | 8/2013 | Kuhn et al. |
| 2019/0187156 A1 | 6/2019 | Quinodoz et al. |
| 2020/0157153 A1* | 5/2020 | Schmidt-Dannert ...................... C12N 9/0018 |

FOREIGN PATENT DOCUMENTS

| | | |
|---|---|---|
| WO | WO 2003/089900 A2 | 10/2003 |
| WO | WO 2017/192633 A1 | 11/2017 |

OTHER PUBLICATIONS

Zakeri "Peptide tag forming a rapid covalent bound to a protein, through engineering a bacterial adhesion" PNAS 2012 109: E692-E697) (Year: 2012).*
Castello "Identification of RNA-binding domains of RNA-binding proteins in cultured cells on a system-wide scale with RBDmap" (Nature Protocols 2017 12:2447-2464). (Year: 2017).*
Li (J. Mol. Biol. 2014 426: 309-317). (Year: 2014).*
Si SpyTag/SpyCatcher Cyclization Enhances the Thermostability of Firefly Luciferase PlosOne 2016 e0162318 (Year: 2016).*
Bantignies, F. et al. Polycomb-Dependent Regulatory Contacts between Distant Hox Loci in *Drosophila*. Cell 144, 214-226 (2011).
Beltran, M. et al. The interaction of PRC2 with RNA or chromatin is mutually antagonistic. Genome Res. 26, 896-907 (2016).
Blackstock, D. et al., Halo-tag mediated self-labeling of fluorescent proteins to molecular beacons for nucleic acid detection, ChemCommun. 2014, vol. 50, pp. 13735-13738.
Bolger, A. M., Lohse, M. & Usadel, B. Trimmomatic: a flexible trimmer for Illumina sequence data. Bioinformatics 30, 2114-2120 (2014).
Brockdorff, N. Noncoding RNA and Polycomb recruitment. RNA 19, 429-442 (2013).
Castello, A. et al. Insights into RNA biology from an atlas of mammalian mRNA-binding proteins. Cell 149, 1393-1406 (2012).
Castello, A., Hentze, M. W. & Preiss, T. Metabolic Enzymes Enjoying New Partnerships as RNA-Binding Proteins. Trends Endocrinol. Metab. 26, 746-57 (2015).
Cerase, A. et al. Spatial separation of Xist RNA and polycomb proteins revealed by superresolution microscopy. Proc Natl Acad Sci U S A 111, 2235-2240 (2014).
Chen, C.-K. et al. Xist recruits the X chromosome to the nuclear lamina to enable chromosome-wide silencing. Science (80-. ). 354, (2016).
Cheutin, T. & Cavalli, G. Polycomb silencing: from linear chromatin domains to 3D chromosome folding. Curr Opin Genet Dev 250, 30-37 (2014).
Chu, C. et al. Systematic discovery of Xist RNA binding proteins. Cell 161, 404-416 (2015).
Cifuentes-Rojas, C., Hernandez, A. J., Sarma, K. & Lee, J. T. Regulatory Interactions between RNA and Polycomb Repressive Complex 2. Mol Cell 55, 171-185 (2014).
Cirillo, D. et al. Quantitative predictions of protein interactions with long noncoding RNAs. Nat. Methods 14, 5-6 (2016).
Da Rocha, S. T. et al. Jarid2 is Implicated in the Initial Xist-Induced Targeting of PRC2 to the Inactive X Chromosome. Mol Cell 53, 301-316 (2014).
Darnell, R. B. HITS-CLIP: panoramic views of protein-RNA regulation in living cells. Wiley Interdiscip Rev RNA 1, 266-286 (2010).
Davidovich, C. et al. Toward a Consensus on the Binding Specificity and Promiscuity of PRC2 for RNA. Mol Cell 57, 552-558 (2015).
Davidovich, C., Zheng, L., Goodrich, K. J. & Cech, T. R. Promiscuous RNA binding by Polycomb repressive complex 2. Nat Struct Mol Biol 20, 1250-1257 (2013).
Derrien, T. et al. The Gencode v7 catalog of human long noncoding RNAs: analysis of their gene structure, evolution, and expression. Genome Res 22, 1775-1789 (2012).
Dobin, A. et al. STAR: ultrafast universal RNA-seq aligner. Bioinformatics 29, 15-21 (2013).

(Continued)

*Primary Examiner* — Changhwa J Cheu
(74) *Attorney, Agent, or Firm* — KNOBBE, MARTENS, OLSON & BEAR LLP

(57) ABSTRACT

In some embodiments, methods of detecting an association between a query protein and a target moiety are described. In some embodiments, compositions are described. In some embodiments, kits are described.

16 Claims, 49 Drawing Sheets

Specification includes a Sequence Listing.

(56) References Cited

OTHER PUBLICATIONS

Engreitz, Jesse M. et al.; "The Xist lncRNA exploits three-dimensional genome architecture to spread across the X-chromosome"; Science; Aug. 16, 2013; 341(6147); 18pp.; doi:10.1126/science.1237973.
Froberg, J. E., Yang, L. & Lee, J. T. Guided by RNAs: X-Inactivation as a Model for lncRNA Function. J. Mol. Biol. 425, 3698-3706 (2013).
G Hendrickson, D., Kelley, D. R., Tenen, D., Bernstein, B. & Rinn, J. L. Widespread RNA binding by chromatin-associated proteins. Genome Biol. 17, 28 (2016).
Galupa, R. & Heard, E. X-chromosome inactivation: new insights into cis and trans regulation. Curr. Opin. Genet. Dev. 31, 57-66 (2015).
Guttman, M. & Rinn, J. L. Modular regulatory principles of large non-coding RNAs. Nature 482, (2012).
Guttman, M. et al. lincRNAs act in the circuitry controlling pluripotency and differentiation. Nature 477, 295-300 (2011).
Hafner, M. et al. Transcriptome-wide identification of RNA-binding protein and microRNA target sites by PAR-CLIP. Cell 141, 129-141 (2010).
Huarte, M. et al. A large intergenic noncoding RNA induced by p53 mediates global gene repression in the p53 response. Cell 142, 409-419 (2010).
Kalantry, S. & Magnuson, T. The Polycomb group protein EED is dispensable for the initiation of random X-chromosome inactivation. PLoS Genet 2, e66 (2006).
Kaneko, S. et al. Interactions between JARID2 and noncoding RNAs regulate PRC2 recruitment to chromatin. Mol Cell 53, 290-300 (2014).
Kaneko, S. et al. Phosphorylation of the PRC2 component Ezh2 is cell cycle-regulated and up-regulates its binding to ncRNA. Genes Dev. 24, 2615-20 (2010).
Kaneko, S., Son, J., Shen, S. S., Reinberg, D. & Bonasio, R. PRC2 binds active promoters and contacts nascent RNAs in embryonic stem cells. Nat Struct Mol Biol 20, 1258-1264 (2013).
Kanhere, A. et al. Short RNAs are transcribed from repressed polycomb target genes and interact with polycomb repressive complex-2. Mol. Cell 38, 675-88 (2010).
Keene, J. D., Komisarow, J. M. & Friedersdorf, M. B. RIP-Chip: the isolation and identification of mRNAs, micro RNAs and protein components of ribonucleoprotein complexes from cell extracts. Nat. Protoc. 1, 302-307 (2006).
Khalil, A. M. et al. Many human large intergenic noncoding RNAs associate with chromatin-modifying complexes and affect gene expression. Proc Natl Acad Sci U S A 106, 11667-11672 (2009).
Kohlmaier, A. et al. A chromosomal memory triggered by Xist regulates histone methylation in X inactivation. PLoS Biol. 2, E171 (2004).
Konig, J. et al. iCLIP reveals the function of hnRNP particles in splicing at individual nucleotide resolution. Nat Struct Mol Biol 17, 909-915 (2010).
Koziol, M. J. & Rinn, J. L. RNA traffic control of chromatin complexes. Curr. Opin. Genet. Dev. 20, 142-8 (2010).
Kozlov, I.A. et al., Efficient Strategies for the Conjugation of Oligonucleotides to Antibodies Enabling Highly Sensitive Protein Detection, Wiley InterScience, Mar. 8, 2004, pp. 621-630.
Kundu, S. et al. Polycomb Repressive Complex 1 Generates Discrete Compacted Domains that Change during Differentiation. Mol. Cell 65, 432-446.e5 (2017).
Kwon, S. C. et al. The RNA-binding protein repertoire of embryonic stem cells. Nat Struct Mol Biol 20, 1122-1130 (2013).
Lassmann, T., Hayashizaki, Y. & Daub, C. O. TagDust—a program to eliminate artifacts from next generation sequencing data. Bioinformatics 25, 2839-2840 (2009).
Lee, J. T. Epigenetic regulation by long noncoding RNAs. Science (80-.). 338, 1435-1439 (2012).
Lee, J. T. Lessons from X-chromosome inactivation: long ncRNA as guides and tethers to the epigenome. Genes Dev 23, 1831-1842 (2009).
Lee, S. et al. Noncoding RNA NORAD Regulates Genomic Stability by Sequestering PUMILIO Proteins. Cell 164, 69-80 (2016).
Licatalosi, D. D. et al. HITS-CLIP yields genome-wide insights into brain alternative RNA processing. Nature 456, 464-469 (2008).
Los, G.V et al., HaloTag: A Novel Protein Labeling Technology for Cell Imaging and Protein Analysis, ACS Chemical Biology, vol. 3, No. 6, Jun. 6, 2008, pp. 373-382.
Lu Z. et al. RNA Duplex Map in Living Cells Reveals Higher-Order Transcriptome Structure. Cell 165, 1267-1279 (2016).
Margueron, R. & Reinberg, D. The Polycomb complex PRC2 and its mark in life. Nature 469, 343-349 (2011).
McHugh, Colleen A. et al.; "The Xist lncRNA interacts directly with Sharp to silence transcription through HDAC3", Nature vol. 521, May 14, 2015, 24pp.
Mili, S. & Steitz, J. A. Evidence for reassociation of RNA-binding proteins after cell lysis: implications for the interpretation of immunoprecipitation analyses. RNA 10, 1692-1694 (2004).
Minajigi, A. et al. Chromosomes. A comprehensive Xist interactome reveals cohesin repulsion and an RNA-directed chromosome conformation. Science (80-.). 349, (2015).
Mohammad, F. et al. Kcnq1ot1/Lit1 noncoding RNA mediates transcriptional silencing by targeting to the perinucleolar region. Mol. Cell. Biol. 28, 3713-28 (2008).
Moindrot, B. et al. A Pooled shRNA Screen Identifies Rbm15, Spen, and Wtap as Factors Required for Xist RNA-Mediated Silencing. Cell Rep. (2015). doi:10.1016/j.celrep.2015.06.053.
Monfort, A., Minin, G. Di, Postlmayr, A., Arieti, F. & Wutz, A. Identification of Spen as a Crucial Factor for Xist Function through Forward Genetic Screening in Haploid Embryonic Stem. Cell Rep. 1-8 (2015). doi:10.1016/j.celrep.2015.06.067.
Ozdilek, B. A. et al. Intrinsically disordered RGG/RG domains mediate degenerate specificity in RNA binding. Nucleic Acids Res. (2017). doi:10.1093/nar/gkx460.
Pandey, R. R. et al. Kcnq1ot1 antisense noncoding RNA mediates lineage-specific transcriptional silencing through chromatin-level regulation. Mol. Cell 32, 232-46 (2008).
Peritz, T. et al. Immunoprecipitation of mRNA-protein complexes. Nat. Protoc. 1, 577-580 (2006).
Plath, K. et al. Role of histone H3 lysine 27 methylation in X inactivation. Science (80-.). 300, 131-135 (2003).
Portoso, M. et al. PRC2 is dispensable for HOTAIR ?mediated transcriptional repression. EMBO J. 36, 981-994 (2017).
Ray, D. et al. Rapid and systematic analysis of the RNA recognition specificities of RNA-binding proteins. Nat. Biotechnol. 27, 667-670 (2009).
Rinn, J. L. & Chang, H. Y. Genome regulation by long noncoding RNAs. Annu Rev Biochem 81, 145-166 (2012).
Rinn, J. L. et al. Functional demarcation of active and silent chromatin domains in human Hox loci by noncoding RNAs. Cell 129, 1311-1323 (2007).
Schoeftner, S. et al. Recruitment of PRC1 function at the initiation of X inactivation independent of PRC2 and silencing. EMBO J. 25, 3110-3122 (2006).
Shishkin, A. A. et al. Simultaneous generation of many RNA-seq libraries in a single reaction. Nat. Methods 12, 323-5 (2015).
Simon, J. A. & Kingston, R. E. Mechanisms of polycomb gene silencing: knowns and unknowns. Nat Rev Mol Cell Biol 10, 697-708 (2009).
Singh, V. et al, Genetically Encoded Multispectral Labeling of Proteins with Polyfluorophores on a DNA Backbone, NIH Public Access Author Manuscript, J. Am. Chem. Soc. 2013, 135(16) 19 pages.
Spitale, R. C., Tsai, M.-C. & Chang, H. Y. RNA templating the epigenome: long noncoding RNAs as molecular scaffolds. Epigenetics 6, 539-43 (2011).
Sundararaman, B. et al. Resources for the Comprehensive Discovery of Functional RNA Elements. Mol. Cell 61, 903-913 (2016).
Terranova, R. et al. Polycomb group proteins Ezh2 and Rnf2 direct genomic contraction and imprinted repression in early mouse embryos. Dev. Cell 15, 668-79 (2008).
Tichon, A. et al. A conserved abundant cytoplasmic long noncoding RNA modulates repression by Pumilio proteins in human cells. Nat. Commun. 7, 12209 (2016).

(56) References Cited

OTHER PUBLICATIONS

Tsai, M. C. et al. Long noncoding RNA as modular scaffold of histone modification complexes. Science (80-.). 329, 689-693 (2010).
Ule, J. et al. Clip Identifies Nova-Regulated RNA Networks in the Brain. Science (80-.). 302, 1212-1215 (2003).
Van Nostrand, E. L. et al. Robust transcriptome-wide discovery of RNA-binding protein binding sites with enhanced CLIP (eCLIP). Nat. Methods (2016). doi:10.1038/nmeth.3810.
Wang, D. et al. LncRNA MALAT1 enhances oncogenic activities of EZH2 in castration-resistant prostate cancer. Oncotarget 6, 41045-55 (2015).
Wang, X. et al. Targeting of Polycomb Repressive Complex 2 to RNA by Short Repeats of Consecutive Guanines. Mol. Cell 65, 1056-1067.e5 (2017).
Woo, C. J. et al. Gene activation of SMN by selective disruption of lncRNA-mediated recruitment of PRC2 for the treatment of spinal muscular atrophy. Proc. Natl. Acad. Sci. U. S. A. 114, E1509-E1518 (2017).
Wu, H.-A. & Bernstein, E. Partners in Imprinting: Noncoding RNA and Polycomb Group Proteins. Dev. Cell 15, 637-638 (2008).
Wutz, A. Gene silencing in X-chromosome inactivation: advances in understanding facultative heterochromatin formation. Nat. Rev. Genet. 12, 542-553 (2011).
Wutz, A., Rasmussen, T. P. & Jaenisch, R. Chromosomal silencing and localization are mediated by different domains of Xist RNA. Nat. Genet. 30, 167-174 (2002).
Xu H. et al. FastUniq: A Fast De Novo Duplicates Removal Tool for Paired Short Reads. PLoS One 7, e52249 (2012).
Yang, L. et al. ncRNA- and Pc2 methylation-dependent gene relocation between nuclear structures mediates gene activation programs. Cell 147, 773-788 (2011).
Yang, Y. W. et al. Essential role of lncRNA binding for WDR5 maintenance of active chromatin and embryonic stem cell pluripotency. Elife 3, e02046 (2014).
Yeo, G. W. et al. An RNA code for the FOX2 splicing regulator revealed by mapping RNA-protein interactions in stem cells. Nat. Struct. Mol. Biol. 16, 130-137 (2009).
Zhao, J. et al. Genome-wide identification of polycomb-associated RNAs by RIP-seq. Mol Cell 40, 939-953 (2010).
Zhao, J., Sun, B. K., Erwin, J. A., Song, J. J. & Lee, J. T. Polycomb proteins targeted by a short repeat RNA to the mouse X chromosome. Science (80-.). 322, 750-756 (2008).
Zovoilis, A., Cifuentes-Rojas, C., Chu, H.-P., Hernandez, A. J. & Lee, J. T. Destabilization of B2 RNA by EZH2 Activates the Stress Response. Cell 167, 1788-1802.e13 (2016).
International Search Report and Written Opinion in Application No. PCT/US2019/051500, dated Nov. 19, 2019.
Rosenberg et al., "Denaturing CLIP, dCLIP, Pipeline Identifies Discrete RNA Footprints on Chromatin-Associated Proteins and Reveals that CBX7 Targets 30 UTRs to Regulate mRNA Expression", Cell Systems 5, 368-385, Oct. 25, 2017.

* cited by examiner

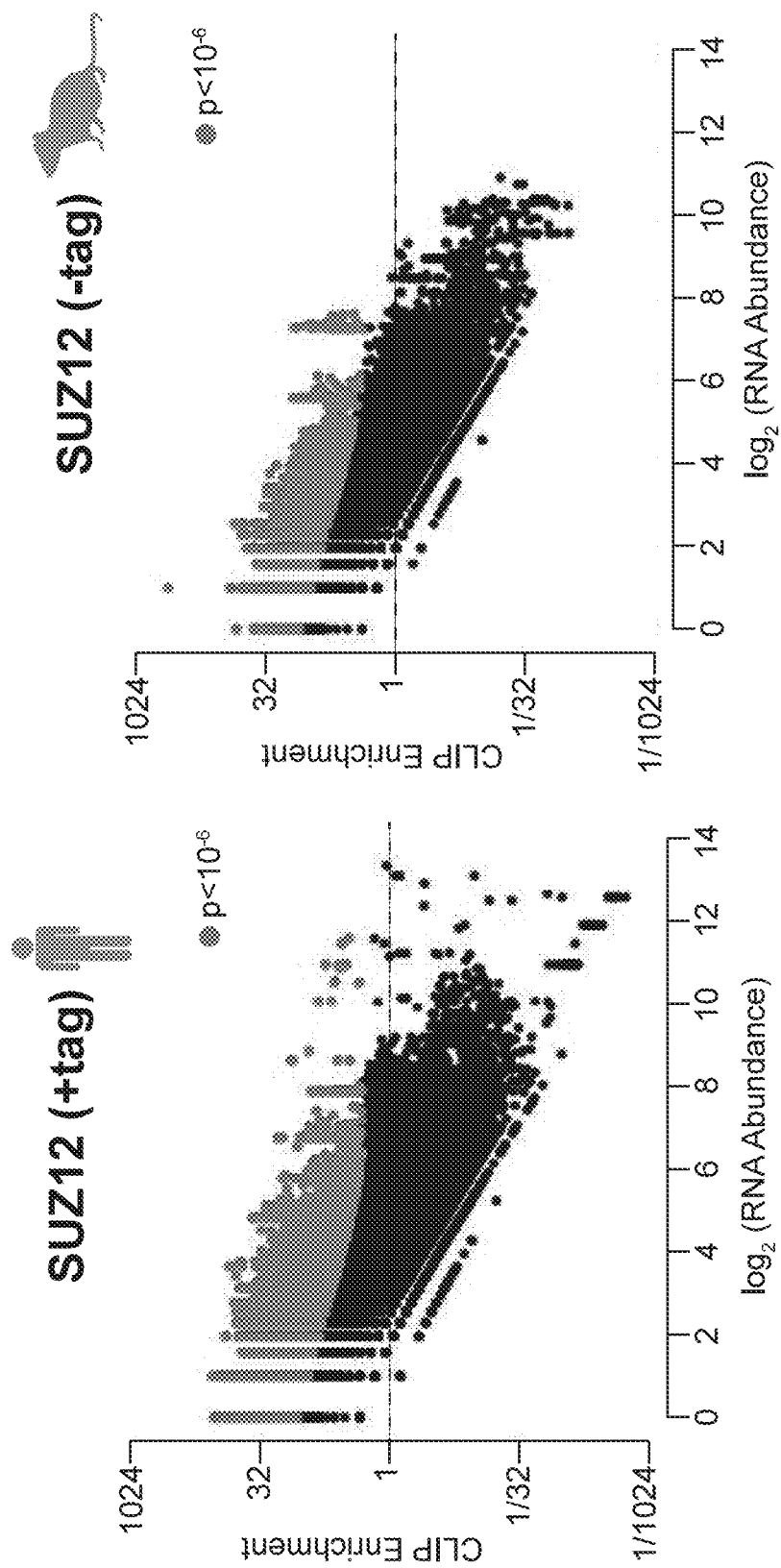

CLAP Replicates

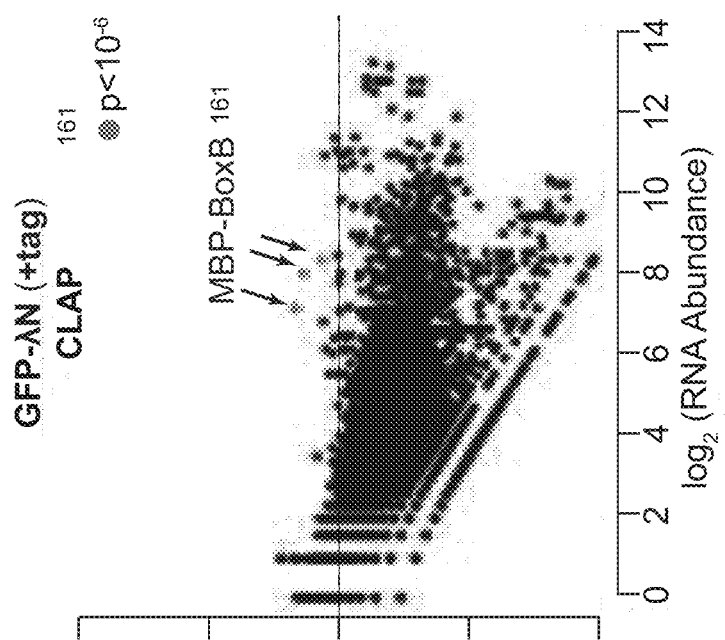
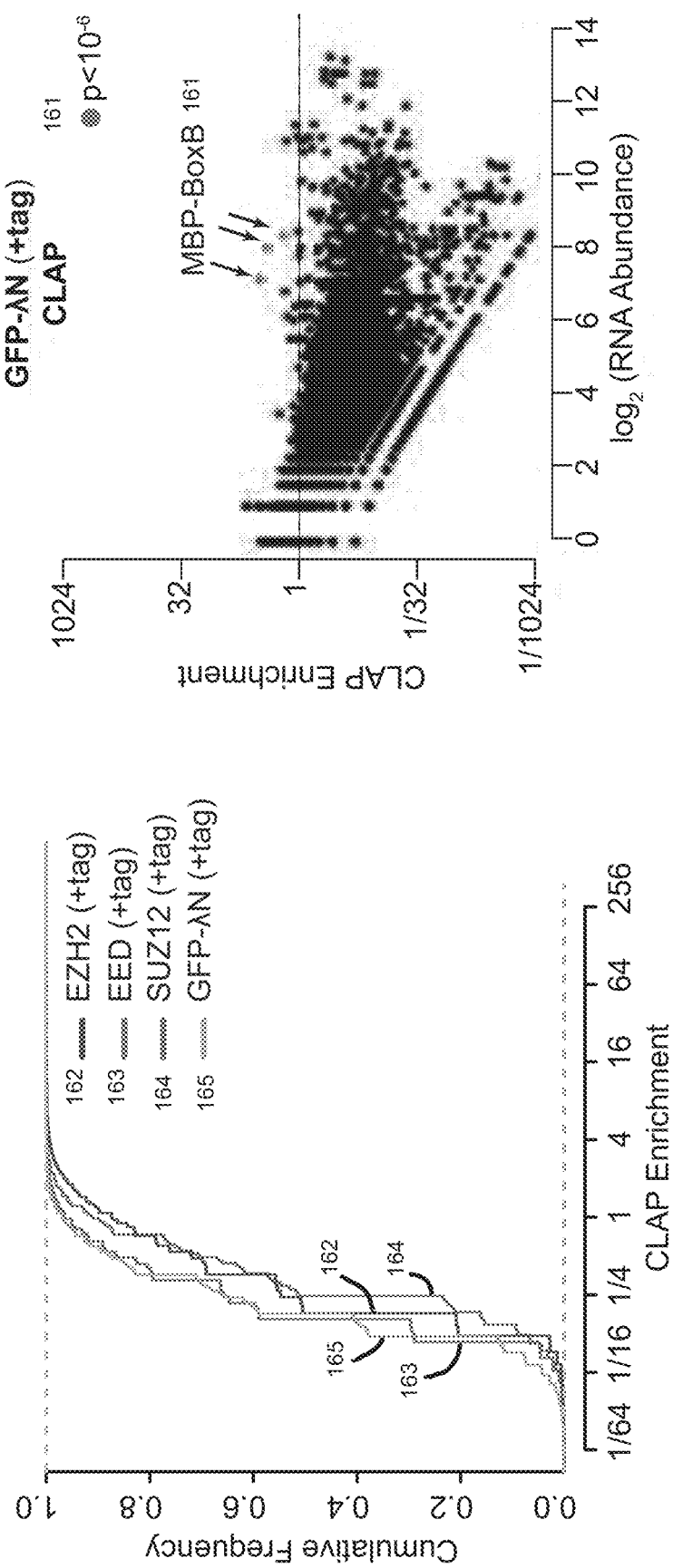
FIG. 16B
FIG. 16A

DETECTION OF MOLECULAR ASSOCIATIONS

INCORPORATION BY REFERENCE TO ANY PRIORITY APPLICATIONS

This application claims the benefit of U.S. Provisional App. No. 62/732,413, filed Sep. 17, 2018, which is incorporated by reference in its entirety herein. Any and all applications for which a foreign or domestic priority claim is identified in the Application Data Sheet as filed with the present application are hereby incorporated by reference under 37 CFR 1.57.

STATEMENT REGARDING FEDERALLY SPONSORED R&D

This invention was made with government support under Grant No. OD012190 awarded by the National Institutes of Health. The government has certain rights in the invention.

REFERENCE TO SEQUENCE LISTING, TABLE, OR COMPUTER PROGRAM LISTING

The present application is being filed along with a Sequence Listing in electronic format. The Sequence Listing is provided as a file CALTE144ASEQLIST.txt, created and last modified on Sep. 17, 2019, which is 1,467 bytes in size. The information in the electronic format of the Sequence Listing is incorporated herein by reference in its entirety.

BACKGROUND

Protein interactions with other molecules are of interest in many areas of biology. For example, RNA-protein interactions are involved in many aspects of RNA biogenesis, processing, and function. Recent attempts to define RNA-protein interactions have led to the discovery of many RNA binding proteins (RBPs) that do not contain canonical RNA binding domains, including chromatin regulators, transcriptional regulators, and metabolic proteins. RNA-protein interactions may play numerous roles, including in chromatin biology, gene regulation, and metabolic control.

FIELD

Some embodiments herein relate to methods, compositions, and kits for detecting associations between proteins and other molecules, for example protein-RNA interactions.

SUMMARY

In some embodiments, a method of detecting an association between a query protein and a target moiety is described. The method can comprise providing a query protein comprising a tag. The method can comprise contacting the query protein with a composition comprising the target moiety, so that the target moiety associates with the query protein. The method can comprise applying a cross-linking agent or force to the query protein and the composition, thus crosslinking the query protein to the target moiety associated therewith. The method can comprise covalently binding the tag to a substrate, thus covalently immobilizing the query protein and crosslinked target moiety on the substrate. The method can comprise washing the immobilized query protein and crosslinked target moiety under denaturing conditions, in which the query protein remains immobilized on the substrate. The method can comprise detecting the target moiety associated with the query protein after the washing. In the method of some embodiments, the method is performed in multiplex, comprising two or more different query proteins, each comprising a different barcode. In the method of some embodiments, the barcode comprises a polynucleotide comprising a coding sequence of the query protein. For example, the barcode can comprise a covalent polypeptide tag fused to the polynucleotide, and wherein said covalent polypeptide tag is covalently bound to a counterpart polypeptide sequence on the query protein. By way of example, the counterpart polypeptide sequence may be disposed at an N terminus of the query protein. Examples of suitable covalent polypeptide tags and counterpart polypeptide sequences include, but are not limited to Spytag and SpyCatcher; or Isopeptag and pilin-C; or SnoopTag and SnoopCatcher; or DogTag and SnoopTagJr; or SdyTag and SdyCatcher. In the method of some embodiments, the providing query protein comprises fusing the covalent polypeptide tag to the polynucleotide encoding the query protein, in which the counterpart polypeptide sequence is disposed at an N-terminal portion of the query protein. The method can further comprise transcribing the polynucleotide in vitro, thus producing the query protein comprising the counterpart polypeptide sequence disposed at the N-terminal portion and further comprising the tag. The method can further comprise covalently binding the polypeptide tag to the counterpart polypeptide sequence, thereby making the query protein comprising the tag and the barcode. In any method described herein, the contacting and applying can be in vivo. For example, providing the query protein comprising the tag comprises expressing a nucleic acid encoding the query protein comprising the tag in vivo. By way of example, the method can comprise administering a vector comprising the nucleic acid encoding the query protein comprising the tag to a cell. In some embodiments, for any of the methods described herein, the tag comprises a haloalkane dehalogenase (such as a HaloTag tag) and the substrate comprises a haloalkane resin; or the tag comprises a DNA methyltransferase (such as a SNAP-tag) and the substrate comprises a benzylguanine resin; or the tag comprises a DNA methyltransferase (such as a CLIP-tag) and the substrate comprises a benzylcytosine resin; or the tag comprises an isopeptag (such as TDKDMTITFTNKKDAE—SEQ ID NO: 1) and the substrate comprises a pilin-C protein; or the tag comprises a SpyTag (such as AHIVMV-DAYKPTK—SEQ ID NO: 2), and the substrate comprises a SpyCatcher protein; or the tag comprises SnoopTag (such as KLGDIEFIKVNK—SEQ ID NO: 3) and the substrate comprises a SnoopCatcher protein; or the tag comprises DogTag (such as DIPATYEFTDGKHYITNEPIPPK—SEQ ID NO: 4) and the substrate comprises SnoopTagJr; or the tag comprises SdyTag (such as DPIVMIDNDKPIT—SEQ ID NO: 5) and the substrate comprises SdyCatcher; or the tag comprises $Cpe0147_{565-587}$ and the substrate comprises $Cpe0147_{439-563}$. In some embodiments, for any of the methods described herein, the target moiety is a protein, a nucleic acid, or a protein-nucleic acid complex. In some embodiments, for any of the methods described herein, n the target moiety is an RNA. In some embodiments, for any of the methods described herein, the washing is at a temperature effective to fragment RNA, thereby fragmenting the target moiety. In some embodiments, for any of the methods described herein, the target moiety is a rare RNA present in 200 or fewer copies per composition. In some embodiments, for any of the methods described herein, the query protein is of unknown RNA binding specificity. In some embodiments, for any of the methods described herein, target moiety is a protein such as an RNA binding protein or complex, and the crosslinking agent comprises a protein-protein crosslinker. In some embodiments, for any of the methods described herein, detecting the target moiety comprises sequencing the target moiety or mass spectrometry. In some embodiments, for any of the methods described herein, the composition comprises a sample. In some embodiments, for any of the methods described herein, the composition further comprises a moiety from a different taxonomic species than the target moiety. In some embodiments, for any of the methods described herein, the substrate comprises a magnetic bead. In some embodiments, for any of the methods described herein, the substrate does not comprise an immunoglobulin or binding fragment thereof. In some embodiments, for any of the methods described herein, the crosslinking agent or force comprises ultraviolet radiation, or an amine-to-amine crosslinker (such as disuccinimidyl suberate or disuccinimidyl tartrate), or a sulfhydryl-to-sulfhydryl crosslinker (such as bis-maleimidoethane or dithio-bis-maleimidoethane), or an aryl-azide (such as N-5-Azido-2-nitrobenzyloxysuccinimide or sulfosuccinimidyl 6-(4'-azido-2'-nitrophenylamino)hexanoate), or a diazirine (such as succinimidyl 4,4'-azipentanoate). In some embodiments, for any of the methods described herein, the crosslinking agent comprises an agent selected from the group consisting of an NHS ester, an imidoester, a difluoro group, an NHS-haloacetyl group, an NHS-maleimide group, an NHS-pyridyldithiol group, a carbodiimide ester and NHS ester, a malemide and a hydrazine group, a pyridyldithiol and a hydrazine group, a NHS ester and an aryl azide, a NHS ester and a diazirine, a NHS ester and an aryl azide, an NHS ester and a diazirine. In some embodiments, for any of the methods described herein, the denaturing conditions comprise a presence of a denaturants, a detergent, and/or a chaotropic salt, or temperatures of at least 60° C., 70° C., 80° C., 90° C., 100° C., 110° C., or 120° C. In some embodiments, for any of the methods described herein, the washing is for no more than 60, 50, 40, 30, 20, or 10 minutes. In some embodiments, for any of the methods described herein, covalently binding the tag to the substrate and washing are performed in a single container, such as a microcentrifuge tube, or well of a multi-well plate.

In some embodiments, a composition is described. The composition can comprise a query protein comprising a tag. The composition can comprise a substrate, in which the tag is covalently bound to the substrate. The composition can comprise a target moiety crosslinked to the query protein. In some embodiments, the composition is under denaturing conditions. In some embodiments, for any of the compositions described herein, the query protein further comprises a barcode comprising an polynucleotide comprising a coding sequence of the query protein. For example, the barcode can comprises a covalent polypeptide tag fused to the polynucleotide, and wherein said covalent polypeptide tag is covalently bound to a counterpart polypeptide sequence on the query protein. By way of example, the counterpart polypeptide sequence can be disposed at an N terminus of the query protein. In some embodiments, for any of the compositions described herein, the tag comprises a haloalkane dehalogenase (such as a HaloTag tag) and the substrate comprises a haloalkane resin; or the tag comprises a DNA methyltransferase (such as a SNAP-tag) and the substrate comprises a benzylguanine resin; or the tag comprises a DNA methyltransferase (such as a CLIP-tag) and the substrate comprises a benzylcytosine resin; or the tag comprises an isopeptag (such as TDKDMTITFTNKKDAE—SEQ ID NO: 1) and the substrate comprises a pilin-C protein; or the tag comprises a SpyTag (such as AHIVMVDAYKPTK—SEQ ID NO: 2), and the substrate comprises a SpyCatcher protein; or the tag comprises SnoopTag (such as KLGDIEFIKVNK—SEQ ID NO: 3) and the substrate comprises a SnoopCatcher protein; or the tag comprises DogTag (such as DIPATYEFTDGKHYITNEPIPPK—SEQ ID NO: 4) and the substrate comprises SnoopTagJr; or the tag comprises SdyTag (such as DPIVMIDNDKPIT—SEQ ID NO: 5) and the substrate comprises SdyCatcher; or the tag comprises Cpe0147$_{565-587}$ and the substrate comprises Cpe0147$_{439-563}$. In some embodiments, for any of the compositions described herein, the substrate comprises a magnetic bead. In some embodiments, for any of the compositions described herein, the substrate does not comprise an immunoglobulin or binding fragment thereof. In some embodiments, for any of the compositions described herein, the crosslinking agent comprises an amine-to-amine crosslinker (such as disuccinimidyl suberate or disuccinimidyl tartrate), or a sulfhydryl-to-sulfhydryl crosslinker (such as bis-maleimidoethane or dithio-bis-maleimidoethane), or an aryl-azide (such as N-5-Azido-2-nitrobenzyloxysuccinimide or sulfosuccinimidyl 6-(4'-azido-2'-nitrophenylamino)hexanoate), or a diazirine (such as succinimidyl 4,4'-azipentanoate). In some embodiments, for any of the compositions described herein, the crosslinking agent comprises an agent selected from the group consisting of an NHS ester, an imidoester, a difluoro group, an NHS-haloacetyl group, an NHS-maleimide group, an NHS-pyridyldithiol group, a carbodiimide ester and NHS ester, a malemide and a hydrazine group, a pyridyldithiol and a hydrazine group, a NHS ester and an aryl azide, a NHS ester and a diazirine, a NHS ester and an aryl azide, and a diazirine.

In some embodiments, a kit is described. The kit can comprise a vector comprising an insertion site and a tag coding sequence, wherein the insertion site is arranged to place a query protein coding sequence in frame with the tag without any intervening stop codon, upon the insertion of the query protein coding sequence in the insertion site. The kit can comprise a substrate configured to specifically bind covalently to the tag. The kit can comprise a crosslinking agent. In some embodiments, the kit further comprises a covalent polypeptide tag. The vector can further comprise a counterpart polypeptide coding sequence, arranged to dispose the counterpart polypeptide sequence at an N-terminal region of the query protein, upon the insertion of the query protein coding sequence in the insertion site. The covalent polypeptide tag and the counterpart polypeptide sequence can be configured to specifically covalently bind to each other. In some embodiments, the kit comprises a nucleic acid encoding the covalent polypeptide tag. In some embodiments, the kit further comprises a denaturing agent. In some embodiments, for any of the kits described herein, the covalent polypeptide tag and counterpart polypeptide sequence comprise a Spytag and SpyCatcher; or Isopeptag and pilin-C; or SnoopTag and SnoopCatcher; or DogTag and SnoopTagJr; or a SdyTag and SdyCatcher. In some embodiments, for any of the kits described herein, the tag comprises a haloalkane dehalogenase (such as a HaloTag tag) and the substrate comprises a haloalkane resin; or the tag comprises a DNA methyltransferase (such as a SNAP-tag) and the substrate comprises a benzylguanine resin; or the tag comprises a DNA methyltransferase (such as a CLIP-tag) and the substrate comprises a benzylcytosine resin; or the tag comprises an isopeptag (such as TDKDMTITFTNKKDAE—SEQ ID NO: 1) and the substrate comprises a pilin-C protein; or the tag comprises a SpyTag (such as AHIVMVDAYKPTK—SEQ ID NO: 2), and the substrate comprises a SpyCatcher protein; or the tag comprises SnoopTag (such as KLGDIEFIKVNK—SEQ ID NO: 3) and the substrate comprises a SnoopCatcher protein; or the tag comprises DogTag (such as DIPATYEFTDGKHYITNEPIPPK—SEQ ID NO: 4) and the substrate comprises SnoopTagJr; or the tag comprises SdyTag (such as DPIVMIDNDKPIT—SEQ ID NO: 5) and the substrate comprises SdyCatcher; or the tag comprises $Cpe0147_{565-587}$ and the substrate comprises $Cpe0147_{439-563}$. In some embodiments, for any of the kits described herein, the substrate comprises a magnetic bead. In some embodiments, for any of the kits described herein, the substrate does not comprise an immunoglobulin or binding fragment thereof. In some embodiments, for any of the kits described herein, the crosslinking agent comprises an amine-to-amine crosslinker (such as disuccinimidyl suberate or disuccinimidyl tartrate), or a sulfhydryl-to-sulfhydryl crosslinker (such as bis-maleimidoethane or dithio-bis-maleimidoethane), or an aryl-azide (such as N-5-Azido-2-nitrobenzyloxysuccinimide or sulfosuccinimidyl 6-(4'-azido-2'-nitrophenylamino)hexanoate), or a diazirine (such as succinimidyl 4,4'-azipentanoate). In some embodiments, for any of the kits described herein, the crosslinking agent comprises an agent selected from the group consisting of an NHS ester, an imidoester, a difluoro group, an NHS-haloacetyl group, an NHS-maleimide group, an NHS-pyridyldithiol group, a carbodiimide ester and NHS ester, a malemide and a hydrazine group, a pyridyldithiol and a hydrazine group, a NHS ester and an aryl azide, a NHS ester and a diazirine, a NHS ester and an aryl azide, and a diazirine.

BRIEF DESCRIPTION OF THE DRAWINGS

FIGS. 1A-1E are a series of schematic diagrams and graphs showing a human and mouse mixing experiment that defines RNA-protein interactions that occur in solution after cell lysis. The experiment utilized a conventional CLIP protocol. FIG. 1A shows a schematic overview of the human and mouse mixing experiment. An epitope-tagged protein is expressed in human cells (+tag) and UV-crosslinked, lysed, and mixed with UV-crosslinked cell lysate from mouse cells not expressing the tagged protein (−tag). The tagged protein is specifically enriched using an antibody against the epitope tag and its associated RNAs are sequenced and aligned to the human and mouse transcriptomes to quantify the amount of signal associated with human RNAs and mouse RNAs, respectively. FIGS. 1B-C show a scatter plots of RNA abundance (log scale, x-axis) compared to CLIP enrichment (log scale, y-axis) for the SUZ12-V5 protein across all 100-nucleotide windows of all annotated human RNAs (+tag, FIG. 1B) and mouse RNAs (−tag, FIC. 1C). Windows with significant enrichment (binomial $p<10^{-6}$) are shown in red. FIGS. 1D-1E show examples of CLIP enrichment (CLIP signal relative to input RNA levels) are plotted for the 3 PRC2 components—EED, EZH2, and SUZ12—across several human lncRNAs (+tag)(FIG. 1D) and mouse lncRNAs (−tag)(FIG. 1E).

FIG. 2A provides a schematic overview comparing the CLIP (left) and CLAP (right) methods. A protein is tagged with both a V5 and HaloTag epitope and expressed in human cells (+tag) and mixed with mouse cells not expressing the tagged protein (−tag). After the human and mouse lysates are mixed, the sample is split into two and CLIP and CLAP are performed on each. CLIP uses an antibody against the V5 epitope followed by standard washes, gel electrophoresis, transfer to a nitrocellulose membrane, and size excision prior to RNA sequencing. CLAP covalently binds the protein to a Halo capture resin and washes in fully denaturing conditions prior to RNA sequencing. FIGS. 2B-C are scatter plots of RNA abundance compared to the CLIP enrichment (FIGS. 2B, 2D, 2F) or CLAP enrichment (FIGS. 2C, 2E, 2G) for SUZ12 (FIGS. 2B-C), EED (FIGS. 2D-E), or EZH2 (FIGS. 2F-G) across all 100-nucleotide windows of annotated mouse RNAs (−tag). Windows with significant enrichment (binomial $p<10^{-6}$) are shown. FIGS. 2H-2J are graphs of examples of CLAP enrichments are plotted for the 3 PRC2 components over mouse lncRNAs that were significantly enriched by CLIP. For comparison purposes, the lncRNA examples are the same as used in FIG. 1D (CLIP −tag). The dashed line indicates an enrichment level of 1.

FIG. 3A shows examples of CLIP (top) and CLAP (bottom) enrichments, plotted for PTBP1 over intronic regions of human mRNAs (+tag). The locations of the corresponding PTBP1 recognition motif (blue boxes) are shown. FIG. 3B shows examples of CLIP (top) and CLAP (bottom) enrichments, plotted for SAF-A over nascent pre-mRNA transcripts. Exons are denoted by boxes and introns by connecting lines in the schematic. FIG. 3C is a density scatter plot of the enrichment levels of PTBP1 over human RNA regions (+tag) as measured by CLIP (x-axis) compared to the enrichment levels as measured by CLAP (y-axis) for all RNAs identified as significantly enriched by CLIP. FIG. 3D is a density scatter plot of the enrichment levels of SAF-A over human RNA regions (+tag) as measured by CLIP (x-axis) compared to the enrichment levels as measured by CLAP (y-axis) for all RNAs identified as significantly enriched by CLIP. FIG. 3E is a cumulative distribution of CLAP enrichment levels for PTBP1 and SAF-A for human RNAs (+tag) or mouse RNAs (−tag) that were significantly enriched in their respective CLIP samples.

FIGS. 4A-B are schematics of the mixing experiment used to compare signal directly on human XIST. The tagged proteins are either transfected into human cells and mixed with untransfected mouse cells (+tag$^{[Human]}$, left) or transfected into mouse cells and mixed with untransfected human cells (−tag$^{[Human]}$, right). FIG. 4C is a graph showing CLIP enrichments for each protein in the +tag$^{[Human]}$ (red) or −tag$^{[Human]}$ (blue) samples are overlaid and plotted over each nucleotide of the human XIST RNA.

FIGS. 5A-D show examples of CLIP (gray, top three rows of each figure) and CLAP (black, bottom three rows of each figure) enrichments for each of the three PRC2 components (EED, EZH2, and SUZ12) are plotted over the human NORAD, KCNQ1ot1, HOTAIR, and TUG1 lncRNAs (+tag). The dashed line indicates an enrichment level of 1. FIGS. 5E-G are scatter plots of RNA abundance compared to CLAP enrichment for EED (FIG. 5E), EZH2 (FIG. 5F), or SUZ12 (FIG. 5G) across all 100-nucleotide windows of all human lncRNAs annotated by Gencode (+tag). Windows with significant enrichment (binomial $p<10^{-6}$) are shown. FIG. 5H is a graph of the cumulative distribution of protein enrichment levels for PRC2 components (EZH2, EED, and SUZ12) and SAF-A defined by CLAP for all RNA regions that were enriched by CLIP for the respective protein. For comparison, the cumulative distribution of CLAP enrichment levels for GFP-XN (black) across all human RNAs are plotted. (d) Density scatter plot of the enrichment levels of EED, EZH2, and SUZ12 as measured by CLIP (x-axis) compared to the enrichment levels as measured by CLAP (y-axis) for all human RNAs (+tag) identified as significantly enriched by CLIP.

FIG. 7A is a schematic diagram of an overview of the Biacore method used to measure the affinity of HaloTag fusion proteins for RNA. In this method, amine groups on HaloTag ligands were first reacted with NHS activated Biacore chip surfaces to covalently immobilize the ligand on the chip surface. Lysate containing HaloTag fusion proteins was then injected onto the chip surface, to allow HaloTag fusion proteins to react with the HaloTag ligand, which covalently links the fusion proteins to the chip surface. Following brief pulses of NaOH to remove non-specifically bound RNA and proteins from the immobilized HaloTag fusion proteins, RNA was injected and the affinity of RNA for HaloTag fusion proteins was measured. FIGS. 7B-G are graphs showing affinity determinations of HaloTag-GFP and HaloTag-GFP-3×LamdaN for MBP-BoxB RNA; HaloTag-PTBP1 for Xist E-repeat RNA; and HaloTag-EED, HaloTag-EZH2 and HaloTag-SUZ12 for Xist A-repeat RNA. The top panels show one data set (colored lines) fit globally to a 1:1 Langmuir binding interaction model (Black lines). The residual plot below the data set shows the distance of each data point from the curve fit. Horizontal lines 71 and 72 in the residual plot show the acceptable and unacceptable, respectively, ranges of residuals reported in the Biacore Evaluation Software. Kinetic constants from all data sets are listed in Table 1.

FIG. 10A is a schematic illustrating several potential ways in which RNA-protein interactions that form in solution may still be detected by CLIP.

FIG. 10B is a an image showing HaloTag-PTBP1 protein was captured on Halo resin and washed with either CLIP wash buffers or CLAP buffers and the remaining associated proteins were boiled off and detected using SyproRuby total protein stain. After boiling associated proteins, PTBP1 was released from the Halo resin by TEV proteolysis and detected using Western blotting with an anti-V5 tag antibody. Black and white triangles indicate eluted PTBP1 and TEV protease, respectively. PTBP1 dimers and trimers are present in TEV elutions and appear at ~110 and ~165 kDa, respectively. FIG. 10C is an image of the same experiment as FIG. 10B, but for EZH2 protein. EZH2 dimers, trimers and tetramers appear at ~160, ~240 and ~320 kDa, respectively, in TEV elutions. FIG. 10D is a graph showing the amount of RNA that was retained after gel electrophoresis, transfer to nitrocellulose and elution was measured from crosslinked (UV+) or non-crosslinked (UV-) lysates. The amount of RNA and its sizes were quantified on an Agilent Bioanalyzer. (FIGS. 10E-F) We coupled crosslinked (UV+) and non-crosslinked (UV-) lysates to amine-reactive beads and washed them with either CLIP buffers (FIG. 10E) or with CLAP wash buffers (FIG. 10F). We measured the amount of RNA that was retained in the crosslinked versus non-crosslinked samples in both cases.

FIGS. 16A-B are a series of graphs showing that GFP-λN has similar binding profile as PRC2 components when measured with CLAP. Cumulative frequency distribution of CLAP enrichment levels for GFP-λN fusion protein across all human RNAs. The enrichment levels for GFP-λN is similar to the CLAP enrichment levels observed for the three PRC2 components across all RNA regions. A scatter plot for all 100 nucleotide windows from the GFP-λN CLAP experiment show that most windows are depleted, except for a few significant windows 161 that correspond to a co-expressed MBP-BoxB RNA control for which λN has known binding affinity.

DETAILED DESCRIPTION

Figure 1A:
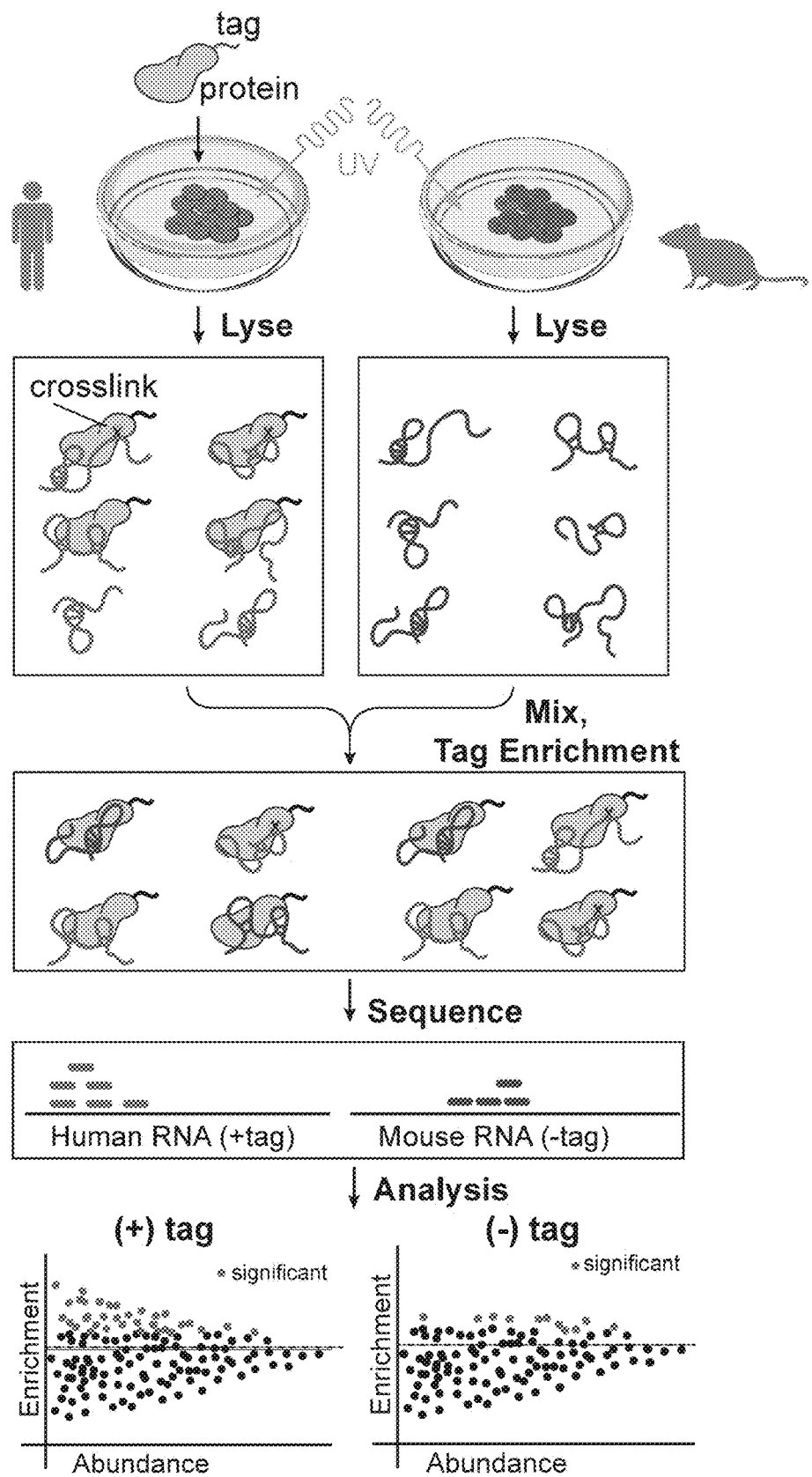

Conventionally, identifying bona fide intramolecular interactions can be challenging. For example, identifying RNA-protein interactions has conventionally been challenging because RNA can form high affinity interactions with proteins in solution (even when they do not occur in vivo), leading to false positive assignments. These conventional challenges can be exacerbated when studying RNA binding proteins that bind few RNA targets in vivo (e.g. PRC2 and SHARP) or where the target RNA is expressed at low levels (e.g. long non-coding RNAs)(lncRNAs). Indeed, conventional protein-centric mapping methods (e.g. RIP and CLIP) may not have sufficient specificity to differentiate bona fide RNA-protein interactions that occur in vivo from those that associate in solution. Due to non-specific associations between proteins and RNA, several proposed lncRNA mechanisms—including for Xist and Hotair—that were based on conventional identification of specific chromatin regulators (e.g. PRC2) and RNA are now known to be incorrect. For example, it is reported herein that conventional methods such as RIP and CLIP identify many strong PRC2-RNA interactions (including with Xist and Hotair) that could not have occurred in vivo because the protein and RNA were not even expressed within the same cell (See Example 1). Without being limited by theory, it is contemplated that one of the conventional biochemical challenges for detecting RNA-protein interactions is that RNA is extremely "sticky" (prone to strongly associating with other proteins and RNAs in cell lysate). Accordingly, promiscuous RNA-protein interactions can form in vitro that do not occur in vivo.

Described herein are methods for detecting an association between a query protein (such as a candidate RNA binding protein) and a target moiety (such as an RNA or another protein). The method can comprise providing a query protein comprising a tag. The tag can be configured to specifically bind covalently to a substrate (for example, a HaloTag tag and a Halo resin substrate). The method can comprise contacting the query protein with a composition comprising the target moiety. The query protein can associate with the target moiety, and then be crosslinked to the target moiety. The tag of the query protein can be bound covalently to the substrate. Thus, the query protein crosslinked to the target moiety can be covalently bound to the substrate. The query protein, target moiety, and substrate can then be washed under denaturing conditions. Without being limited by theory, molecules that non-specifically interact with the query protein can be washed away under denaturing conditions, while the query protein remains crosslinked to the target moiety and bound to the substrate. Thus, target moieties that remain associated with the query protein after the washing can be detected. These target moieties are likely to represent bona fide interactors with the query protein.

Also described are compositions such as intermediates of methods for detecting an association between a query protein (such as a candidate RNA binding protein) and a target moiety (such as RNA) as described herein. Also described herein are kits for performing methods for detecting an association between a query protein as described herein.

Methods, compositions, and kits as described herein address challenges of conventional techniques by describing a framework for RNA-protein biochemistry, which may be generally referred to as Covalent Capture methods. For example, described in accordance with some embodiments herein is are a class of methods, which may be referred to as Covalent Linkage and Affinity Purification (CLAP), that make use of covalent protein capture to permit purification in denaturing conditions, and permit highly specific purification and mapping of individual protein binding sites on any RNA (or other candidate binding moiety, such as a DNA or another protein). The methods can involve genetic tagging of a protein with covalent epitope tags, which can then be specifically and covalently captured through an intramolecular protein ligation reaction with an affinity resin. By covalently linking the captured protein on magnetic beads, covalent links are formed from the bead to the target protein to interacting RNAs (via UV crosslinks), permitting wash stringencies that are fully denaturing, thereby disrupting all interactions that are not covalently linked. As shown herein, CLAP removes RNA-protein interactions that occur in solution (Example 2) while retaining in vivo RNA-protein interactions detected by CLIP for a wide range of well-characterized RNA binding proteins (Examples 3-4). Together, these results provide a framework for studying bona fide RNA-protein interactions that occur in cells. These methods are also amenable to multiplexed proteome-wide mapping of all protein binding sites on RNA in a single pooled experiment (which may be also referred to as method called High-throughput CLAP (Hi-CLAP)).

Query Proteins and Target Moieties

As used herein "query protein" has its customary and ordinary meaning as would be understood by one of ordinary skill in the art in view of this disclosure. It refers to a polypeptide that can be used to detect interactions with that polypeptide. For example, the query protein can comprise, consist essentially of, or consist of an RNA binding protein, a member of an RNA binding protein complex, or a chromatin protein. In methods, compositions, and kits of some embodiments herein, the query protein comprises a tag (as described in more detail herein). The tag may specifically covalently bind to a substrate material as described herein. The tag may be disposed on the query protein such that it is accessible to covalently bind to a substrate. For example, the tag may be disposed at an N terminus or C terminus of the query protein, or on an exposed surface or loop of the query protein.

As used herein "target moiety" has its customary and ordinary meaning as would be understood by one of ordinary skill in the art in view of this disclosure. It refers to a moiety (such as a molecule or complex of molecules) with which a query protein may associate. It will be understood that association is a type of interaction, and accordingly, wherever an "association" (or variation of this root term) is mentioned herein, an "interaction" (or suitable variation of this root term) will also be understood to take place. Example target moieties include proteins, nucleic acids, protein-nucleic acid and/or complexes. For example, the target moiety can comprise, consist essentially of, or consists of RNA.

In methods, compositions, and kits of some embodiments, the query protein comprises, consists essentially of, or consists of an RNA binding protein, and the target moiety comprises, consists essentially of, or consists of an RNA, DNA, protein, and/or small molecule, or a combination of two or more of any of the listed items.

Vectors

As described in more detail herein, in methods of some embodiments herein, query proteins can be provided by expressing the query protein in vivo. For example, a nucleic acid encoding the query protein can be expressed in a cell. The nucleic acid can be provided to the cell in a suitable expression vector. Additionally, in kits of some embodiments, a vector may be provided for the expression of a query protein.

As used herein "vector" has its customary and ordinary meaning as would be understood by one of ordinary skill in the art in view of this disclosure. It refers to a construct configured to contain a nucleic acid (such as a nucleic acid encoding a query protein), and provide that nucleic acid to a host cell. Examples of suitable vectors for methods, kits, and compositions of some embodiments include, but are not limited to a plasmids and viral vectors, for example, an adenoviral vector or adeno associated viral vector. Vectors can include, for example, plasmids such as pSVL and pKSV-10 available from Pharmacia, pBPV-1/pML2d (International Biotechnologies, Inc.), and pCDNA and pTDT1 (ATCC, #31255); viral vectors such based on vaccinia virus, poliovirus, adenovirus, herpes simplex virus, a lentivirus; vectors derived from retroviruses such as Rous Sarcoma Virus, Harvey Sarcoma Virus, avian leukosis virus, human immunodeficiency virus, myeloproliferative sarcoma virus, and mammary tumor virus); adeno-associated virus vectors, and the like. Additional examples of suitable eukaryotic vectors include bovine papilloma virus-based vectors, Epstein-Barr virus-based vectors, SV40, 2-micron circle, pcDNA3.1, pcDNA3.1/GS, pYES2/GS, pMT, p IND, pIND (Sp1), pVgRXR (Invitrogen), and the like. Derivatives and variants of any of the listed vectors are also contemplated in some embodiments.

Generation of a vector comprising the nucleic acid encoding the query protein can be accomplished using any suitable genetic engineering techniques well known in the art, including, without limitation, the techniques such as restriction endonuclease digestion, ligation, transformation, plasmid purification, and DNA sequencing, for example as described in Green and Sambrook (Molecular Cloning: A Laboratory Manual. 4th Edition. Cold Spring Harbor Laboratory Press, N.Y. (2012)), which is incorporated by reference in its entirety herein.

In some embodiments, any vector as described herein comprises an insertion site. By way of example, the insertion site may comprise one or more restriction endonuclease sites, a multiple cloning site (MCS), or a GATEWAY destination site. The insertion site can be disposed for the insertion of a nucleic acid encoding a query protein in a desired location on the vector. For example, the vector can comprise a promoter, and the insertion site may be positioned 3' to the promoter, for example within 10 bp, 20, 30, 40, 50, 100, 150, 200, 250, 300, 400, 500, 600, 700, 800, 900, 1000, 1100, 1200, 1500, or 2000 bp 3' to the promoter. Suitable promoters can be selected for the desired expression environment. For example, the promoter may comprise a robust promoter such as the cytomegalovirus (CMV) promoter.

Tags and Substrates

As used herein "tag" has its customary and ordinary meaning as would be understood by one of ordinary skill in the art in view of this disclosure. It refers to motif or domain on a polypeptide that specifically covalently binds to a "substrate material" (which for conciseness, may be referred to as a "substrate," though it will be a appreciated that a substrate may also comprise other substances in addition to the noted substrate material). A substrate tag that "specifically" (or variations of this root term) covalently binds to a substrate material does not necessitate that a tag only interacts with or binds to one material at the absolute exclusion of all others. "Specifically" or "specific" covalent binding also includes tags that preferentially covalently bind to the substrate material compared to other substances that are present, though insubstantial or trivial interactions with other substances may still occur under some circumstances.

As described herein, it is contemplated that a query protein, through its tag can be immobilized on a substrate by way of a covalent bond between the tag and the substrate. As such, the query protein (and any target moieties crosslinked thereto) can remain associated with the protein even under denaturing conditions, while non-covalently bound substances (such as moieties that interact non-specifically with the query protein) are washed way under denaturing conditions.

It is contemplated that any tag that specifically forms a covalent bond to a substrate material can be used with query proteins as described herein. Examples of suitable tags (and corresponding substrate materials) for methods, compositions, and kits of embodiments described herein are shown in Table 0.1. In some embodiments, a tag comprises, consists essentially of, or consists of a tag shown in Table 0.1. In some embodiments, a substrate material (or "substrate") comprises, consists essentially of, or consists of a substrate material shown in Table 0.1. In some embodiments, a tag comprises, consists essentially of, or consists of a tag shown in Table 0.1, and a substrate material (or "substrate") comprises, consists essentially of, or consists of a substrate material that corresponds to the tag as shown in Table 0.1.

TABLE 0.1

Example tags and substrate

| Example Tag | Example Substrate Material |
| --- | --- |
| haloalkane dehalogenase (such as a HaloTag tag) | haloalkane resin such as Haloresin |
| DNA methyltransferase (such as a SNAP-tag) | benzylguanine resin |
| DNA methyltransferase (such as a CLIP-tag) | benzylcytosine resin |
| isopeptag (such as TDKDMTITFTNKKDAE - SEQ ID NO: 1) | pilin-C protein |
| SpyTag (such as AHIVMVDAYKPTK - SEQ ID NO: 2) | SpyCatcher protein |
| SnoopTag (such as KLGDIEFIKVNK - SEQ ID NO: 3) | SnoopCatcher protein |
| DogTag (such as DIPATYEFTDGKHYITNEPIPPK - SEQ ID NO: 4) | SnoopTagJr |
| SdyTag (such as DPIVMIDNDKPIT - SEQ ID NO: 5) | SdyCatcher |
| Cpe0147$_{565-587}$ | Cpe0147$_{439-563}$ |

Suitable substrate may comprise surfaces (such as surface of wells or test tubes), as well as plates, and beads. By way of example, a substrate may comprise magnetic beads such as magnetic agarose beads. For example, the substrate may comprise, consist essentially of, or consist of a bead, and the surface of the bead may comprise, consist essentially of, or consist of a substrate material as described herein. In some embodiments, the tag comprises haloalkane dehalogenase (such as a HaloTag tag), and the substrate is a magnetic bead comprising haloalkane resin such as Haloresin on its surface.

Crosslinking Force Sand Agents

As used herein "crosslinking forces" and "crosslinking agents" have their customary and ordinary meaning as would be understood by one of ordinary skill in the art in view of this disclosure. These terms refer to forces and agents that can induce the formation of covalent bonds between substances that are in proximity each other, for example, a query protein associated with target moiety as described herein. Advantageously, the crosslinking forces and agents of some embodiments may be used in vivo, so that a query protein and associated target moiety in vivo may be covalently bound together, and remain covalently bound together after they are recovered from the in vivo environment. It is contemplated that by crosslinking query proteins and target moieties in vivo, bona fide associations between the query proteins and target moieties can be detected. Subsequent non-covalently interacting-substances (such as artifacts of contact with other substances or sample materials or contaminants) can be removed under denaturing conditions as described herein. In contrast, and without being limited by theory, in vitro methods to identify intermolecular interactions (for example performed in cell extracts) may identify artifactual associations, for example between molecules that are expressed in different cell types or different cellular compartments, or at different times, and are unlikely to actually associate in vivo.

In methods, compositions, and kits of some embodiments, the crosslinking agent or force comprises ultraviolet radiation, or an amine-to-amine crosslinker (such as disuccinimidyl suberate or disuccinimidyl tartrate), or a sulfhydryl-to-sulfhydryl crosslinker (such as bis-maleimidoethane or dithio-bis-maleimidoethane), or an aryl-azide (such as N-5-Azido-2-nitrobenzyloxysuccinimide or sulfosuccinimidyl 6-(4'-azido-2'-nitrophenylamino)hexanoate), or a diazirine (such as succinimidyl 4,4'-azipentanoate). By way of example, a crosslinking agent may comprise an agent selected from the group consisting of an NHS ester, an imidoester, a difluoro group, an NHS-haloacetyl group, an NHS-maleimide group, an NHS-pyridyldithiol group, a carbodiimide ester and NHS ester, a malemide and a hydrazine group, a pyridyldithiol and a hydrazine group, a NHS ester and an aryl azide, a NHS ester and a diazirine, a NHS ester and an aryl azide, and a diazirine, or a combination of two or more of any of the listed items. In methods, compositions, and kits of some embodiments, the crosslinking agent or force comprises ultraviolet radiation, or an amine-to-amine crosslinker (such as disuccinimidyl suberate or disuccinimidyl tartrate), or a sulfhydryl-to-sulfhydryl crosslinker (such as bis-maleimidoethane or dithio-bis-maleimidoethane), or an aryl-azide (such as N-5-Azido-2-nitrobenzyloxysuccinimide or sulfosuccinimidyl 6-(4'-azido-2'-nitrophenylamino)hexanoate), or a diazirine (such as succinimidyl 4,4'-azipentanoate), or an NHS ester, an imidoester, a difluoro group, an NHS-haloacetyl group, an NHS-maleimide group, an NHS-pyridyldithiol group, a carbodiimide ester and NHS ester, a malemide and a hydrazine group, a pyridyldithiol and a hydrazine group, a NHS ester and an aryl azide, a NHS ester and a diazirine, a NHS ester and an aryl azide, and a diazirine, or a combination of two or more of any of the listed items.

Denaturing Conditions and Washes

As used herein "denaturing conditions" has it ordinary and customary meaning as would be understood by one of ordinary skill in the art in view of this disclosure. It refers to conditions that disrupt non-covalent intermolecular interactions, thus permitting removal of non-covalent intermolecular interactions by washing. "Denaturing conditions" may also be referred to herein as "stringent" conditions. Examples of denaturing conditions suitable for methods, compositions, and kits of some embodiments include the presence of a denaturant, for example a detergent (such as sodium dodecyl sulfate, ethyl trimethyl ammonium bromide and/or deoxycholate), and/or a chaotropic agent (such as n-butanol, ethanol, guanidinium chloride, lithium perchlorate, lithium acetate, magnesium chloride, phenol, 2-propanol, thiourea, and/or urea). Denaturing conditions may also comprise two or more of the listed items. Denaturing conditions may also comprise heat. For example, a temperature higher than typical human body heat may denature human proteins, and thus may represent denaturing conditions, for example at least 41° C., 45° C., 50° C., 55° C., 60° C., 65° C., 70° C., 75° C., 80° C., 85° C., 90° C., 95° C., 100° C., 105° C., 110° C., 115° C., or 120° C., including ranges between two or more of the listed values, such as 41° C.-120° C., or 41° C.-100° C., or 41° C.-90° C., or 50° C.-120° C., or 50° C.-100° C., or 50° C.-90° C.

Methods of Detecting an Association Between a Query Protein and a Target Moiety

In some embodiments, methods of detecting an association between a query protein and a target moiety are described. The method can comprise providing a query protein comprising a tag as described herein. The query protein can be contacted with a composition comprising or suspected of comprising a target moiety. For example, the contacting can comprise adding or mixing. For example, the query protein can be contacted with the composition (such as a cell or the contents of a cell) in vivo. The query protein can associate with the target moiety. The method can further comprise detecting an association between the query protein and the target moiety. The method can further comprise applying a crosslinking agent or force to the query protein and the composition, thus crosslinking the query protein to the associated target moiety. The method can further comprise covalently binding the tag to a substrate, thus covalently immobilizing the query protein and crosslinked target moiety on the substrate. The method can further comprise washing the immobilized query protein and crosslinked target moiety under denaturing conditions, in which the query protein remains immobilized on the substrate. It is contemplated that at this stage, non-specifically-interacting moieties have been substantially washed away from the query protein under denaturing conditions, while the crosslinked target moiety remains. As such, the method can comprise detecting the target moiety associated with the query protein after the washing, for example by sequencing (of the target moiety, and/or a barcode on the target moiety), or mass spectrometry. By way of example, the method of some embodiments may be referred to herein as "CLAP." Optionally, any of the methods described herein may be repeated.

In some embodiments, the method of detecting an association between a query protein and a target moiety is performed in multiplex (such methods may also be referred to as "multiplex" methods). The multiplex method can comprise two or more different query proteins, each of which comprises a different barcode. The different query proteins may each comprise the same tag, so that they may be covalently bonded to the same substrate. By way of example, the multiplex method (which may also be referred to herein as "High-throughput CLAP" or "Hi-CLAP"). In the multiplex method of some embodiments, each query protein may be barcoded with a nucleic acid comprising a coding sequence of the query protein, such as an mRNA. For example, the query proteins can be made by fusing a polypeptide tag to polynucleotide encoding the query protein. The query protein can be translated from the polynucleotide. The polynucleotide can further encode a counterpart polypeptide sequence that that is part of the query protein, and that specifically covalently binds to the polypeptide tag. The counterpart polypeptide sequence can be disposed in an N-terminal region of the query protein, so that the polypeptide tag can co-translationally (or immediately following translation) form a covalent bond with the counterpart polypeptide sequence. Accordingly, the query protein can be barcoded with the polynucleotide comprising the coding sequence of the query protein. Optionally, the polynucleotide may further comprise a random oligonucleotide barcode, for example a random oligonucleotide barcode of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides, including ranges between any two of the listed values, for example, 3-10, 3-20, 3-30, 3-50, 6-10, 6-20, 6-30, 6-50, 10-20, 10-30, 10-50, 20-30, or 20-50 nucleotides. Examples of suitable covalent polypeptide tag and counterpart polypeptide sequences include, but are not limited to, a Spytag and SpyCatcher; or Isopeptag and pilin-C; or SnoopTag and SnoopCatcher; or DogTag and SnoopTagJr; or SdyTag and SdyCatcher.

In the multiplex method of some embodiments, the method comprises fusing a covalent polypeptide tag to the polynucleotide encoding the query protein. By way of example, the fusing can comprise forming a covalent linkage with the polynucleotide, for example a phosphodiester linkage, or another suitable linkage, for example, if the polynucleotide comprises a modified base. In some embodiments, the fusing comprises crosslinking the polypeptide tag to the polynucleotide encoding the query protein. The crosslinking may comprise a crosslinking agent or force as described herein. In the multiplex method of some embodiments, the counterpart polypeptide sequence is disposed at an N terminus of the query protein.

As such, in some embodiments, providing the query protein in the multiplex method comprises fusing the covalent polypeptide tag to the polynucleotide encoding the query protein (so that the counterpart polypeptide sequence is disposed at an N-terminal portion of the query protein), and transcribing the polynucleotide in vitro, thus producing the query protein comprising the counterpart polypeptide sequence disposed at the N-terminal portion and further comprising the tag. The method can further comprise covalently binding the polypeptide tag to the counterpart polypeptide sequence, thus making the query protein comprising the tag and the barcode.

The methods of detecting an association between a query protein and a target moiety as described herein can be performed in vivo. By way of example, the crosslinking agent or force as described can be applied to the query protein and composition in vivo. By way of example, the query protein can be contacted with a composition comprising the target moiety (for example, a cell, or portion of a cell) in vivo. For example, providing the query protein comprising the tag can comprise expressing a nucleic acid encoding the query protein comprising the tag in vivo. In some embodiments, the query protein is expressed by a vector comprising a nucleic acid encoding the query protein comprising the tag as described herein. The method can further comprise administering the vector comprising the nucleic acid encoding the query protein comprising the tag to a cell, prior to expressing the query protein in the cell. The vector can be a vector as described herein.

In the method of detecting an association between a query protein and a target moiety of some embodiments, the tag and substrate are configured to specifically covalently bind to each other. In the method of detecting an association between a query protein and a target moiety of some embodiments, the tag comprises a haloalkane dehalogenase (such as a HaloTag tag) and the substrate comprises a haloalkane resin; and/or the tag comprises a DNA methyltransferase (such as a SNAP-tag) and the substrate comprises a benzylguanine resin; and/or the tag comprises a DNA methyltransferase (such as a CLIP-tag) and the substrate comprises a benzylcytosine resin; and/or the tag comprises an isopeptag (such as TDKDMTITFTNKK-DAE—SEQ ID NO: 1) and the substrate comprises a pilin-C protein; and/or the tag comprises a SpyTag (such as AHIVMVDAYKPTK—SEQ ID NO: 2), and the substrate comprises a SpyCatcher protein; and/or the tag comprises SnoopTag (such as KLGDIEFIKVNK—SEQ ID NO: 3) and the substrate comprises a SnoopCatcher protein; and/or the tag comprises DogTag (such as DIPATYEFTDGKHYIT-NEPIPPK—SEQ ID NO: 4) and the substrate comprises SnoopTagJr; and/or the tag comprises SdyTag (such as DPIVMIDNDKPIT—SEQ ID NO: 5) and the substrate comprises SdyCatcher; and/or the tag comprises Cpe0147$_{565-587}$ and the substrate comprises Cpe0147$_{439-563}$.

In the method of detecting an association between a query protein and a target moiety, of some embodiments, the substrate comprises, consists essentially of or consists of a bead. For example, the substrate can comprise a magnetic bead. The substrate can further comprise a substrate material that is covalently bound by the tag, for example on the surface of the magnetic bead.

Without being limited by theory, it contemplated that methods described herein detect associations between query proteins and target moieties with superior specificity to immunoprecipitation methods (which can involve retaining a complex through antibody binding to a molecule of interest, and thus, in contrast to the covalent bonds described herein, cannot wash away non-specific non-covalent interactions under denaturing conditions without also interfering with antibody binding). Accordingly, in some embodiments, the substrate does not comprise an immunoglobulin or binding fragment thereof. An antibody is an example of an immunoglobulin. As used herein "antibody" encompasses full-length antibodies, in addition to binding fragments thereof.

In the method of detecting an association between a query protein and a target moiety of some embodiments, the target moiety comprises, consists essentially of or consists of a protein or a nucleic acid or a protein-nucleic acid complex. Example nucleic acids include RNAs and/or DNAs. Example proteins include RNA binding proteins. Example protein-nucleic acid complexes include chromatin. In the method of detecting an association between a query protein and a target moiety of some embodiments the target moiety comprises, consists essentially of or consists of a protein or a protein-nucleic acid complex. In the method of detecting an association between a query protein and a target moiety of some embodiments the target moiety comprises, consists essentially of or consists of a nucleic acid or a protein-nucleic acid complex. In the method of detecting an association between a query protein and a target moiety of some embodiments the target moiety comprises, consists essentially of or consists of a protein. In the method of detecting an association between a query protein and a target moiety, of some embodiments the target moiety comprises, consists essentially of, or consists of a nucleic acid. In the method of detecting an association between a query protein and a target moiety, of some embodiments, the target moiety comprises, consists essentially of or consists of an RNA. It has been observed that methods described herein can identify low-copy-number rare RNAs (See, e.g., FIGS. 17A-B and Note 2). For example, the methods can detect a target moiety that is a rare RNA, such as an RNA present in 200 or fewer copies per composition, for example no more than 200, 100, 75, 50, or 25 copies. It is further noted that the methods described herein can detect protein-RNA interactions de novo. As such, in the method of some embodiments, the query protein is of unknown RNA binding specificity. In some embodiments, the target moiety is a protein or protein-nucleic acid complex such as an RNA binding protein or complex. Thus, the crosslinking agent can comprise a protein-protein crosslinker.

A number of suitable denaturing conditions can be used for the washing in the method of detecting an association between a query protein and a target moiety, of some embodiments. For example, the wash can comprise a denaturing conditions as described herein. In some embodiments, the wash comprises a denaturing agent such as a detergent and/or a chaotropic agent as described herein. For any of the washes described herein, the denaturing conditions can also comprise a temperature that is greater than the body temperature of a human. Additionally, it is contemplated that these higher temperatures can fragment RNA. Without being limited by theory, heat fragmentation of RNA can advantageously avoid structural biases that may be associated with enzymatic RNA digestion, while achieving suitably sized RNA fragments. Accordingly, in some embodiments, the washing is at a temperature effective to fragment RNA, thus fragmenting a target moiety that comprises, consists essentially of, or consists of RNA. By way of example, the wash can be at a temperature of at least 41° C., 45° C., 50° C., 55° C., 60° C., 65° C., 70° C., 75° C., 80° C., 85° C., 90° C., 95° C., 100° C., 105° C., 110° C., 115° C., or 120° C., including ranges between two or more of the listed values, such as 41° C.-120° C., or 41° C.-100° C., or 41° C.-90° C., or 50° C.-120° C., or 50° C.-100° C., or 50° C.-90° C. In the method of some embodiments, the denaturing conditions comprise a presence of a denaturants, a detergent, and/or a chaotropic salt, or temperatures of at least 60° C., 70° C., 80° C., 90° C., 100° C., 110° C., or 120° C.

Advantageously, the methods of detecting an association between a query protein and a target moiety described herein can wash the query protein crosslinked to the target moiety (or moieties) without gel extraction, and thus can be faster than conventional approaches which may involve gel extraction. In the method of some embodiments, the washing is for no more than 60, 50, 40, 30, 20, or 10 minutes. In the method of some embodiments, the method does not comprise gel extraction. As an additional advantage, the methods of some embodiments can be performed in a single container, for example a well of a multi-well plate (such as a 96-well plate, though any number of wells can be suitable), or test tube such as a microcentrifigure tube. The use of a single container can expedite the method, while minimizing resource usage.

In the method of some embodiments, a number of approaches can be used to detect the target moiety associated with the query protein after washing. For example, the target moiety or a barcode associated with the target moiety (such as an oligonucleotide barcode) can be sequenced by nucleic acid sequencing, or can be characterized by mass spectrometry. Optionally, after washing, the target moiety can be eluted prior to subsequent analysis, for example, nucleic acid sequencing and/or mass spectrometry.

A number of nucleic acid sequencing techniques are suitable for use in accordance with methods, compositions, and kits described herein. In some embodiments, droplet-based high throughput sequencing of these conjugate pairs reveals paired information about the receptor proteins and the antigenic proteins they respond to and/or are capable of responding to. In some embodiments, any next-generation/high-throughput sequencing technology currently known and/or in development can be used to perform the sequence analyses disclosed herein. Non-limiting examples include massively parallel signature sequencing (MPSS), polony sequencing, single-molecule real-time sequencing (Pacific Biosciences) Illumina (Solexa) sequencing, Roche 454 sequencing, ion torrent semiconductor sequencing, sequencing by ligation (SOLiD) sequencing, pyrosequencing, shotgun sequencing, nanopore sequencing, chain termination (Sanger) sequencing), DNA nanoball sequencing, heliscope single molecule sequencing, and single molecule real time (SMRT) sequencing.

A number of suitable mass spectrometry methods can be used to detect a target moiety that has been associated with a query protein, for example, mass spectrometry/mass spectrometry (MS/MS), matrix-assisted laser desorption/ionization (MALDI), and liquid chromatography mass spectrometry such as electrospray ionization liquid chromatography mass spectrometry (ESI-LC-MS).

By way of example, in MS/MS a particular characteristic peak of a mass spec profile is further analyzed (e.g. sequenced). This is also known as Triple Quadruple Mass Spectrometry. By way of example, in ESI-LC-MS, molecular ions, as well as structural information of the molecules can be observed, and the solution-phase information can also be retained into the gas-phase if needed. By way of example, in MALDI, a soft ionization technique is used in mass spectrometry, and may permit the analysis of even relatively fragile moieties, which may be fragmented when ionized by more conventional ionization methods.

In the method of detecting an association between a query protein and a target moiety of some embodiments, the composition comprises a sample, for example a biological sample such as a cell (for example an isolated cell or cell culture), a supernatant, a tissue (for example a tissue biopsy or tissue culture or blood), or a combination or fraction of any of the listed items. In the method of some embodiments, the composition comprises a cell or cellular compartment in vivo.

As described herein, methods of detecting an association between a query protein and a target moiety of some embodiments can identify bona fide intermolecular interactions with minimal or no contamination from artifactual molecules, for example molecules of a different species (See, e.g., Example 1). Accordingly, in the method of some embodiments, the composition further comprises a moiety from a different taxonomic species than the target moiety. Without being limited by theory, it is contemplated that the method preferentially detects bona fide interactions between molecules, such as between RNA binding proteins and RNAs, and as such, moieties from a different species may not interfere with the detecting.

In the method of detecting an association between a query protein and a target moiety of some embodiments, the crosslinking agent or force comprises ultraviolet radiation, or an amine-to-amine crosslinker (such as disuccinimidyl suberate or disuccinimidyl tartrate), or a sulfhydryl-to-sulfhydryl crosslinker (such as bis-maleimidoethane or dithiobis-maleimidoethane), or an aryl-azide (such as N-5-Azido-2-nitrobenzyloxysuccinimide or sulfosuccinimidyl 6-(4'-azido-2'-nitrophenylamino)hexanoate), or a diazirine (such as succinimidyl 4,4'-azipentanoate). In the method of some embodiments, the crosslinking agent comprises an agent selected from the group consisting of an NHS ester, an imidoester, a difluoro group, an NHS-haloacetyl group, an NHS-maleimide group, an NHS-pyridyldithiol group, a carbodiimide ester and NHS ester, a malemide and a hydrazine group, a pyridyldithiol and a hydrazine group, a NHS ester and an aryl azide, a NHS ester and a diazirine, a NHS ester and an aryl azide, and a diazirine.

Compositions

In some embodiments, compositions are described. The composition can be an intermediate of a method of detecting an association between a query protein and a target moiety as described herein. In some embodiments, the composition comprises a query protein comprising a tag as described herein. The composition can further comprise a substrate, in which the substrate is covalently bound to the substrate. The composition can further comprise a target moiety crosslinked to the query protein. The composition can be under denaturing conditions as described herein. By way of example, the target moiety can comprise, consists essentially of, or consist of a nucleic acid such as an RNA, a protein, or a protein-nucleic acid complex.

In the composition of some embodiments, the query protein further comprises a barcode comprising a polynucleotide comprising a coding sequence of the query protein, such as an mRNA. By way of example, the barcode can comprise a covalent polypeptide tag fused to the polynucleotide. The covalent polypeptide tag can be covalently bound to a counterpart polypeptide sequence on the query protein. Examples of suitable covalent polypeptide tags and counterpart polypeptide sequence are described herein. For example, the covalent polypeptide tag and counterpart polypeptide sequence comprise a Spytag and SpyCatcher; or Isopeptag and pilin-C; or SnoopTag and SnoopCatcher; or DogTag and SnoopTagJr; or SdyTag and SdyCatcher. In some embodiments, the counterpart polypeptide sequence is disposed at an N terminus of the query protein. As described herein, the N-terminal placement of the counterpart polypeptide sequence can facilitate co-translational bonding between the covalent polypeptide tag fused to the polynucleotide and the counterpart polypeptide sequence, so as to increase the fidelity by which the query protein is tagged with it coding sequence.

In the composition of some embodiments, the tag and substrate are as described in Table 0.1. In some embodiments, the tag comprises a haloalkane dehalogenase (such as a HaloTag tag) and the substrate comprises a haloalkane resin; and/or the tag comprises a DNA methyltransferase (such as a SNAP-tag) and the substrate comprises a benzylguanine resin; and/or the tag comprises a DNA methyltransferase (such as a CLIP-tag) and the substrate comprises a benzylcytosine resin; and/or the tag comprises an isopeptag (such as TDKDMTITFTNKKDAE—SEQ ID NO: 1) and the substrate comprises a pilin-C protein; and/or the tag comprises a SpyTag (such as AHIVMVDAYKPTK—SEQ ID NO: 2), and the substrate comprises a SpyCatcher protein; and/or the tag comprises SnoopTag (such as KLGDIEFIKVNK—SEQ ID NO: 3) and the substrate comprises a SnoopCatcher protein; and/or the tag comprises DogTag (such as DIPATYEFTDGKHYITNEPIPPK—SEQ ID NO: 4) and the substrate comprises SnoopTagJr; and/or the tag comprises SdyTag (such as DPIVMIDNDKPIT—SEQ ID NO: 5) and the substrate comprises SdyCatcher; and/or the tag comprises $Cpe0147_{565-587}$ and the substrate comprises $Cpe0147_{439-563}$. In the composition of some embodiments, the substrate comprises, consists essentially of, or consists of a bead. For example, the substrate can comprise a magnetic bead. The substrate can further comprise a substrate material that is covalently bound by the tag, for example on the surface of the magnetic bead.

Kits

In some embodiments, kits are described. The kits can be useful for performing a method of detecting an association between a query protein and a target moiety as described herein. The kit can comprise a vector, for example a vector as described herein. The vector can be a nucleic acid vector. The vector can comprise an insertion site and a tag coding sequence. The insertion site can be arranged to place a query protein coding sequence in frame with the tag without any intervening stop codon, upon the insertion of the query protein coding sequence in the insertion site. As such, the insertion site can be arranged so that upon inserting a query protein coding sequence into the vector, the vector encodes the tagged query protein. The kit can further comprise a substrate configured to specifically bind covalently to the tag. The kit can further comprise a crosslinking agent. The crosslinking agent can be selected to associate a query protein with a target moiety (for example, protein-protein, or protein-nucleic acid).

The kit can further comprise a reagents for a multiplex method of detecting an association between a query protein and a target moiety as described herein. For example, the kit can comprise a covalent polypeptide tag, or a coding sequence therefor. The vector can further comprise a counterpart polypeptide coding sequence, arranged to dispose the counterpart polypeptide sequence at an N-terminal region of the query protein, upon the insertion of the query protein coding sequence in the insertion site. The covalent polypeptide tag and the counterpart polypeptide sequence can specifically covalently bind to each other. For example, the covalent polypeptide tag and counterpart polypeptide sequence can comprise a Spytag and SpyCatcher; or Isopeptag and pilin-C; or SnoopTag and SnoopCatcher; or DogTag and SnoopTagJr; or SdyTag and SdyCatcher.

In some embodiments, the kit further comprises a denaturing agent as described herein.

In the kit of some embodiments, the tag and substrate are as described in Table 0.1. In some embodiments, the tag comprises a haloalkane dehalogenase (such as a HaloTag tag) and the substrate comprises a haloalkane resin; and/or the tag comprises a DNA methyltransferase (such as a SNAP-tag) and the substrate comprises a benzylguanine resin; and/or the tag comprises a DNA methyltransferase (such as a CLIP-tag) and the substrate comprises a benzylcytosine resin; and/or the tag comprises an isopeptag (such as TDKDMTITFTNKKDAE—SEQ ID NO: 1) and the substrate comprises a pilin-C protein; and/or the tag comprises a SpyTag (such as AHIVMVDAYKPTK—SEQ ID NO: 2), and the substrate comprises a SpyCatcher protein; and/or the tag comprises SnoopTag (such as KLGDIEFIKVNK—SEQ ID NO: 3) and the substrate comprises a SnoopCatcher protein; and/or the tag comprises DogTag (such as DIPATYEFTDGKHYITNEPIPPK—SEQ ID NO: 4) and the substrate comprises SnoopTagJr; and/or the tag comprises SdyTag (such as DPIVMIDNDKPIT—SEQ ID NO: 5) and the substrate comprises SdyCatcher; and/or the tag comprises Cpe0147565-587 and the substrate comprises Cpe0147439-563. In the kit of some embodiments, the substrate comprises, consists essentially of, or consists of a bead. For example, the substrate can comprise a magnetic bead. The substrate can further comprise a substrate material that is covalently bound by the tag, for example on the surface of the magnetic bead. In some embodiments, the substrate does not comprise an immunoglobulin (such as an antibody) or binding fragment thereof.

In the kit of some embodiments, the crosslinking agent comprises an amine-to-amine crosslinker (such as disuccinimidyl suberate or disuccinimidyl tartrate), or a sulfhydryl-to-sulfhydryl crosslinker (such as bis-maleimidoethane or dithio-bis-maleimidoethane), or an aryl-azide (such as N-5-Azido-2-nitrobenzyloxysuccinimide or sulfosuccinimidyl 6-(4'-azido-2'-nitrophenylamino)hexanoate), or a diazirine (such as succinimidyl 4,4'-azipentanoate). In the kit of some embodiments, the crosslinking agent comprises an agent selected from the group consisting of an NHS ester, an imidoester, a difluoro group, an NHS-haloacetyl group, an NHS-maleimide group, an NHS-pyridyldithiol group, a carbodiimide ester and NHS ester, a malemide and a hydrazine group, a pyridyldithiol and a hydrazine group, a NHS ester and an aryl azide, a NHS ester and a diazirine, a NHS ester and an aryl azide, and a diazirine.

Additional Embodiments

The Polycomb Repressive Complex 2 (PRC2) has been reported to bind to many RNAs and has emerged as a central player in reports describing the mechanisms of how long non-coding RNAs (lncRNAs) regulate gene expression. Yet, there is a growing discrepancy between the biochemical evidence supporting specific lncRNA-PRC2 interactions and functional evidence demonstrating that PRC2 is often dispensable for lncRNA function. Here we revisit the evidence supporting broad RNA binding by PRC2 components and show that many previously reported PRC2-RNA interactions do not represent in vivo interactions but occur in solution after lysis. We develop a method called Covalent Linkage and Affinity Purification (CLAP) that enables denaturing purification of in vivo crosslinked RNA-protein complexes and show that it removes RNA-protein interactions that occur in solution while accurately retaining in vivo crosslinked RNA-protein interactions. Using CLAP, we confirm the known RNA binding profiles of several well-characterized RNA binding proteins. In contrast, we find that RNA binding of the PRC2 components is abolished, with virtually no mRNAs or lncRNAs showing significant enrichment for any of the PRC2 components. Our results demonstrate that PRC2 components do not bind directly to many RNAs in vivo and provides a new tool for defining bona fide lncRNA-protein interactions that occur in cells.

RNA-protein interactions are involved in many aspects of RNA biogenesis, processing, and function. Recent attempts to define RNA-protein interactions have led to the discovery of many novel RNA binding proteins (RBPs) that do not contain canonical RNA binding domains, including chromatin regulators, transcriptional regulators, and metabolic proteins. These discoveries have led to widespread interest in defining what role RNA-protein interactions might play in chromatin biology, gene regulation, and metabolic control.

Yet, without being limited by theory, defining RNA-protein interactions have been challenging conventionally because RNA can form high affinity interactions with proteins in solution—even when they do not occur in vivo leading to false positive assignments. This issue has conventionally been even more challenging when studying RNA binding proteins that bind few RNA targets in vivo (e.g. PRC2 and SHARP) or where the target RNA is expressed at low levels (e.g. lncRNAs). Indeed, convectional protein-centric mapping methods (e.g. RIP and CLIP) do not have the specificity required to separate bona fide RNA-protein interactions that occur in vivo from those that associate in solution. Because of this issue, several proposed lncRNA mechanisms—including for Xist and Hotair—that were based on the identification of specific chromatin regulators (e.g. PRC2) and RNA are now known to be incorrect. For example, we found that current methods such as RIP and CLIP identify many strong PRC2-RNA interactions (including with Xist and Hotair) that could not have occurred in vivo because the protein and RNA were not even expressed within the same cell. These results highlight a biochemical challenge for defining RNA-protein interactions—because RNA is extremely "sticky" (prone to strongly associating with other proteins and RNAs in cell lysate) promiscuous RNA-protein interactions can form in vitro that do not occur in vivo.

The Polycomb Repressive Complex 2 (PRC2), a chromatin regulatory complex that deposits the repressive H3K27me3 histone modification[1,2], has emerged as a central player in reports describing the mechanisms of how long non-coding RNAs (lncRNAs) regulate gene expression[3-10]. To date, hundreds of lncRNAs have been reported to bind PRC2[3-5,7,9-12] and recent studies have found that PRC2 components bind broadly to many RNAs, including lncRNAs and mRNAs[13-15], leading to the proposal that PRC2 has a widespread functional role through its interactions with RNA. These proposed functional roles include that lncRNAs can act to guide PRC2 to specific genomic DNA sites[8,16-19], tether protein components of the PRC2 complex[15], activate PRC2 enzymatic function[20], and that PRC2 can act as a nuclease to degrade specific RNAs[21]. In addition, nascent mRNAs have been proposed to bind PRC2 to preclude binding to DNA at active genes[13,14,22].

One of the first reported PRC2-RNA interactions and the paradigm example for the functional relevance of these interactions is the Xist lncRNA[5,23]. Xist orchestrates X chromosome inactivation (XCI) by localizing across the inactive X chromosome, recruiting numerous chromatin modifying complexes, including PRC2 and its associated H3K27me3 mark[24,25], and mediating chromosome-wide transcriptional silencing[24,25]. PRC2 has been reported to bind to the A-repeat region of Xist[5,26], the same RNA region that is required for Xist-mediated transcriptional silencing[27]. These observations led to a model whereby Xist directly binds to PRC2 and recruits this repressive chromatin complex to the X chromosome in order to mediate transcriptional silencing[5,23,28].

Yet, deletion of PRC2 components that prevent its recruitment to the X chromosome have no impact on Xist-mediated transcriptional silencing[29,30] and deletion of the A-repeat does not preclude PRC2 recruitment to the X chromosome[31-34]. In addition, the distance between Xist and PRC2 on the inactive X chromosome as measured by super-resolution microcopy appears to be incompatible with direct binding[35]. Recently, we and others purified Xist using denaturing conditions and failed to identify an interaction between Xist and any of the PRC2 components in vivo[33,36,37]. Instead, we identified several other direct Xist interacting proteins that are required for Xist-mediated transcriptional silencing and PRC2 recruitment[33,36,38,39]. It is now clear that PRC2 is also dispensable for the functions of several other lncRNAs, including HOTAIR, which it has been previously reported to bind[31,40,41]. Accordingly, there is a discrepancy between the biochemical evidence supporting lncRNA-PRC2 interactions and functional evidence demonstrating that PRC2 is often dispensable for lncRNA function.

The evidence for widespread PRC2-RNA interactions in vivo is based on two general approaches-RNA Immunoprecipitation (RIP) and Crosslinking and Immunoprecipitation (CLIP). RIP utilizes native purification conditions in crosslinked or non-crosslinked cells to immunoprecipitate proteins and measure their associated RNAs[42-44]. In contrast, CLIP utilizes UV crosslinking to form covalent interactions in cells between directly interacting RNA and protein followed by purification in more stringent wash conditions (i.e. 1M salt) and subsequent separation through a denaturing gel and transfer to a nitrocellulose membrane in order to enrich for in vivo crosslinked RNA-protein interactions[45-49]. Because of this increased stringency, CLIP methods have emerged as the conventional standard for defining in vivo RNA-protein interactions and have been successfully used to define the precise RNA binding sites of numerous RNA binding proteins[45].

Without being limited by theory, a possible explanation for the discrepancies between the biochemical and functional data for PRC2-RNA interactions comes from several recent in vitro experiments showing that PRC2 components bind with high affinity to all RNAs, including bacterial RNAs[22,50,51]. In a classic experiment, Mili and Steitz showed that immunoprecipitation methods can identify RNA-protein interactions that do not occur in vivo, but rather form in solution after lysis[52]. Based on these observations, we considered the possibility that PRC2 components do not actually interact broadly with RNA in vivo, but instead that current methods do not fully exclude RNAs that bind to PRC2 in solution after cell lysis.

Here we develop a human and mouse mixing experiment that allows us to accurately identify RNA-protein interactions that occur in solution after lysis and find that CLIP identifies many strong PRC2-RNA interactions that do not occur in vivo. To address this issue, we develop a method called Covalent Linkage and Affinity Purification (CLAP) that enables covalent coupling of a protein of interest to a solid support followed by purification of its associated, in vivo crosslinked, RNAs using fully denaturing conditions. In accordance with methods, compositions, and kits of some embodiments, we show that CLAP removes RNA-protein interactions that occur in solution while retaining in vivo RNA-protein interactions detected by CLIP for well-characterized RNA binding proteins. Using CLAP, we did not detect an interaction between any of the PRC2 components and Xist. More generally, we find that the RNA binding profiles of the PRC2 components are dramatically reduced with virtually no RNAs, mRNAs or lncRNAs, showing enrichment for any of the PRC2 components. Together, our results indicate that PRC2 components do not directly bind to RNA broadly in vivo and provides a new tool for defining bona fide lncRNA-protein interactions that occur in cells.

Note 1: Possible Explanations for why CLIP May not Fully Exclude RNA-Protein Interactions that Form in Solution.

Without being limited by theory, we considered several possible explanations for why CLIP identifies RNA-protein interactions that do not occur in vivo.

The RNAs that are detected may be crosslinked to other non-specific proteins that may still be present after immunoprecipitation. Because CLIP utilizes immunoprecipitation, the stringency of purification is limited to native conditions that can maintain the antibody-protein interaction as well as the interaction between the Protein G resin and the antibody. These conditions have been shown to retain non-crosslinked protein-protein interactions in the case of PRC2 components[13] and may similarly retain other protein-protein interactions that form in solution. To determine whether other proteins may still be present after immunoprecipitation in CLIP conditions, we purified two different proteins (PTBP1 and EZH2) using CLIP conditions and visualized all of the proteins present after elution using a total protein stain and identified a large number of non-specific proteins (FIGS. 10A-F). Although CLIP employs gel separation and excision of RNA-protein complexes within a defined size range to further exclude non-specific proteins, many of the non-specific proteins that are identified in these gels are within the size range that is excised for each of these proteins and therefore would not be excluded by this step (FIGS. 10A-F). These results may explain why the level of background RNA binding is significantly lower when CLIP is performed in non-crosslinked lysates or in knockout cells that lack the target protein that is immunoprecipitated[13,15].

Figure 3A:
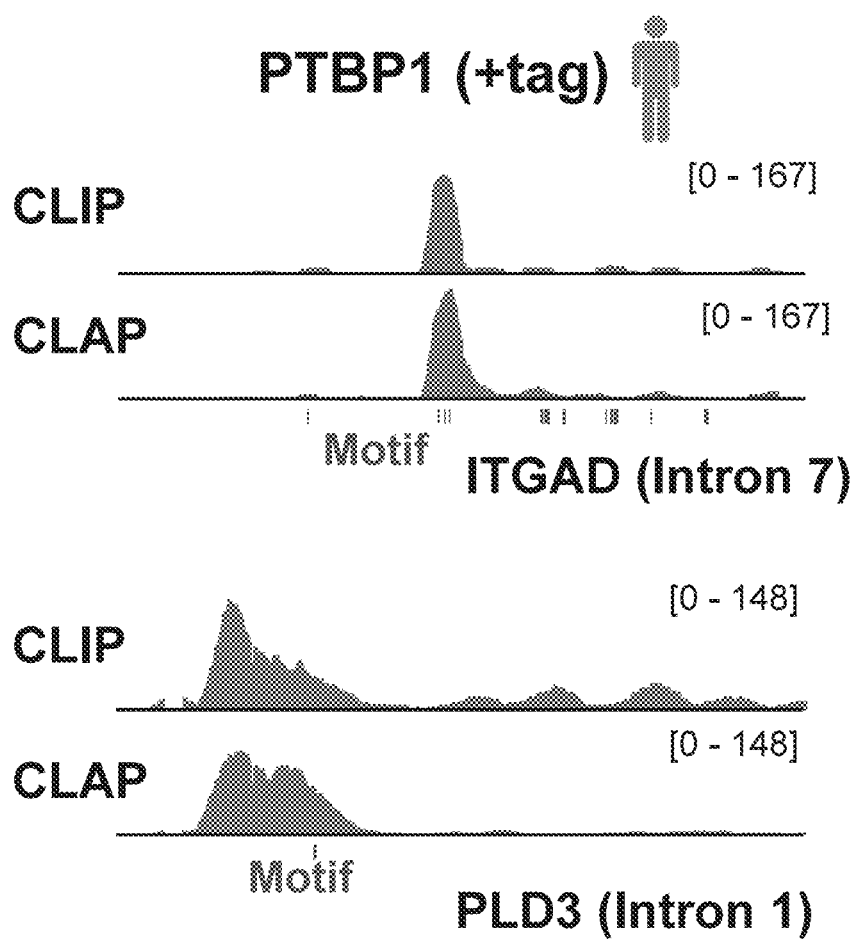
FIGS. 3A-E are a series of graphs showing that CLAP accurately identifies RNA-protein interactions that occur in vivo for well-defined RNA binding proteins in accordance with some embodiments.

Without being limited by theory, the specific protein that is purified may interact with RNAs in solution to form non-crosslinked RNA-protein complexes. To account for the limitations on wash stringency imposed by the use of antibodies, CLIP makes uses of denaturing gel electrophoresis and transfer to a nitrocellulose membrane to enrich for crosslinked RNA-protein interactions because nitrocellulose is expected to only bind to proteins, but not free RNA. We tested the amount of non-crosslinked RNA that is retained after CLIP washes and after gel separation and transfer to a nitrocellulose membrane by measuring the amount of RNA retrieved from UV-crosslinked cells and non-crosslinked cells (FIGS. 10A-F). Significantly, we recover a large amount of RNA from the non-crosslinked samples after CLIP washes and also after gel separation and transfer to nitrocellulose. In fact, each procedure results in only an ~4-fold depletion relative to the amount of RNA purified from UV-crosslinked samples (FIGS. 10A-F). Because of the low efficiency of RNA-protein crosslinking generated by UV light (~1-5%)[45], most RNA and protein in the sample are expected to be non-crosslinked and accordingly may lead to the detection of non-crosslinked RNA-protein interactions, such as those that form in solution. In addition, in solution association of a protein directly with an RNA may lead to enrichment of an RNA that is crosslinked to a distinct protein in vivo. This direct association of RNA and protein in solution may explain why we observe strong binding sites in the −tag samples that appear to reflect the known binding motif for the PTBP1 protein (FIG. 3F).

Without being limited by theory, it is contemplated that both of these issues may arise in the CLIP procedure because the protein purification and denaturation steps are decoupled due to the use of antibodies for protein purification. Despite these potential issues, we expect that the signal from in vivo crosslinked RNA-protein interactions will be strongly enriched by the CLIP procedure, yet in cases where a protein does not actually bind to RNA in vivo or where it binds to few, or low abundance, RNA targets, these issues may lead to detection of a large amount of RNA-protein interactions that form in solution after cellular lysis because in these cases the non-specific RNA targets may be present within the sample at a significantly higher abundance relative to bona fide targets.

Note 2: Additional Features of the CLAP Method

In addition to the increased stringency that can be achieved by CLAP, there are several features of the CLAP method in accordance with some embodiments herein.

Figure 17A:
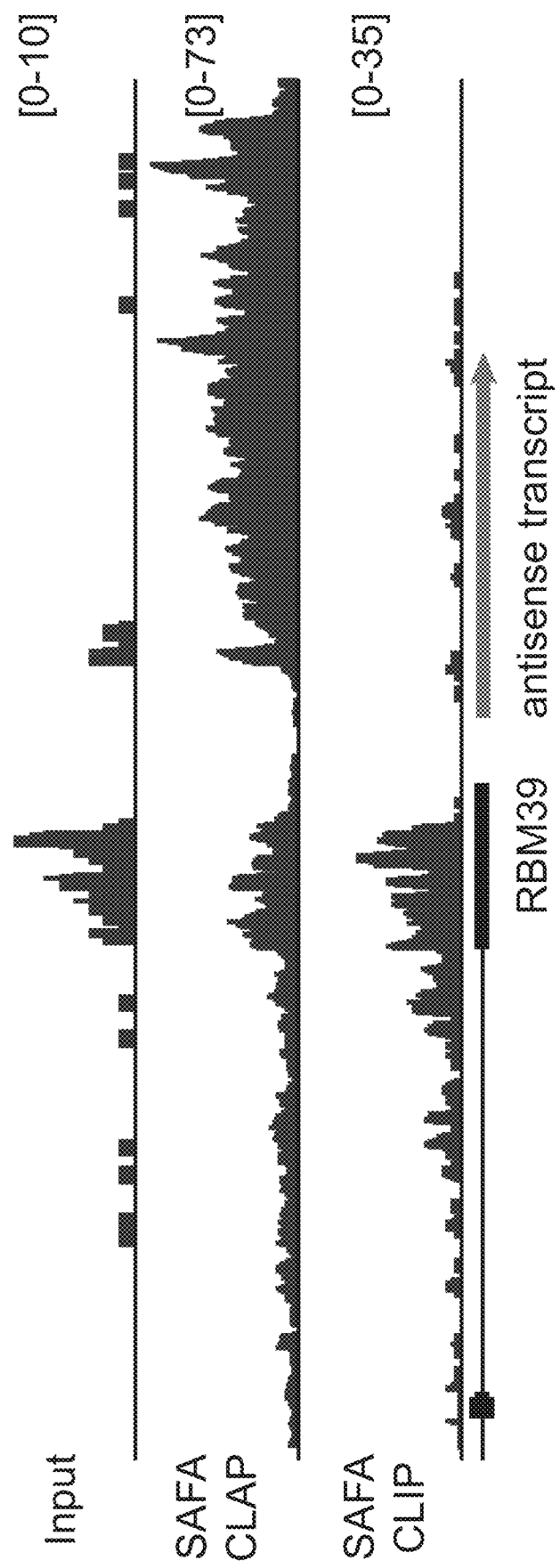
FIGS. 17A-B is a series of graphs showing that CLAP can achieve higher sensitivity for defining RNA-protein interactions that occur with rare RNA transcripts. Read counts for Input RNA (top panel), CLAP (middle panel), and CLIP (bottom panel) aligned to genomic DNA regions are shown in each figure. Arrow indicates a region that is transcribed antisense to the protein coding gene annotated (black). Scale range of read counts are shown in brackets.
Figure 17B:
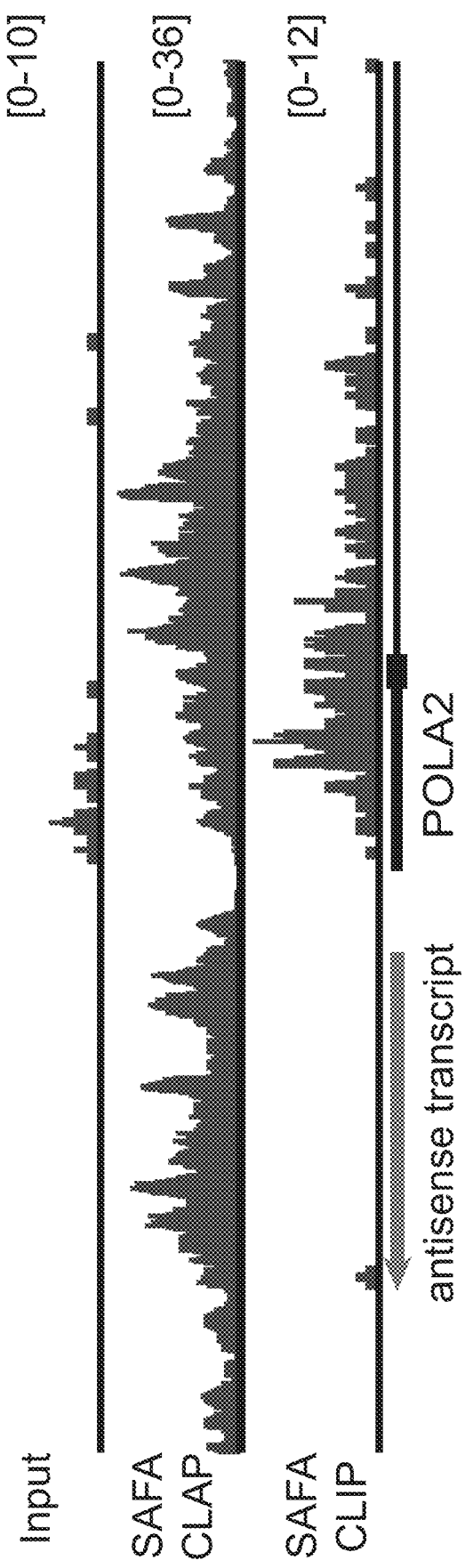

CLAP can provide increased sensitivity for identifying RNA-protein interactions that occur with rare RNA transcripts. Specifically, in exploring the SAF-A CLAP data, we identified numerous additional low abundance RNAs that are enriched in the SAF-A CLAP samples but were not detected by CLIP (FIGS. 17A-B). Consistent with the known binding profile of SAF-A, these RNAs also correspond to nascent transcripts that are present on chromatin but were present at very low overall expression levels. This suggests that by reducing the level of background binding, CLAP may also provide increased sensitivity for identifying interactions that occur with rare transcripts.

CLAP can take less time and require fewer cells to perform relative to CLIP. A key step in the CLIP procedure is gel electrophoresis, transfer to nitrocellulose, and extraction of RNA by proteolytic digestion. Because CLAP is a covalent purification procedure it allows for purification in fully denaturation conditions directly upon protein capture thereby eliminating the need for gel extraction. Accordingly, after protein capture, CLAP takes ~30 minutes for washes prior to RNA purification whereas CLIP takes several hours. In addition, because the material loss during the gel separation, transfer, and extraction steps are high, we find that we can perform CLAP from significantly fewer cells than is needed for CLIP. Finally, because CLAP does not require gel extraction, the entire procedure can be performed within a single microcentrifuge tube or 96-well plate thereby increasing the number of proteins that can be processed simultaneously.

An additional advantage of CLAP is that the fragmentation of the RNA to defined sizes can be accomplished using heat during the washes. This eliminates the need for RNase digestion during lysis. Notably, different RNases are well known to have different sequence and structural biases that can impact different RNAs. Because RNase digestion is known to be highly variable, CLIP generally requires extensive optimization of RNase concentration for each experiment and can also further vary based on the expected binding profile of the protein. In contrast, heat fragmentation does not have known sequence or structural biases and is highly reproducible from experiment to experiment thereby reducing variability and increasing robustness of the procedure.

CLAP can be used with different crosslinking reagents, including those that form protein-protein interactions as described herein, to enable exploration of indirect protein-RNA interactions. Because CLIP makes use of denaturation and size selection of crosslinked RNA-protein complexes, it requires use of UV crosslinking which only forms crosslinking between directly interaction RNA and protein. In contrast, because CLAP enables direct denaturation, it can be used with crosslinking reagents that form larger complexes. This would be highly valuable for exploring RNA interactions with protein complexes, such as chromatin regulatory complexes, where the exact RNA binding protein may not be well defined.

Additional Options

In addition to the items noted above, the following options are set forth:

1. A method of detecting an association between a query protein and a target moiety, the method comprising:
   providing a query protein comprising a tag;
   contacting the query protein with a composition comprising the target moiety, whereby the target moiety associates with the query protein;
   applying a crosslinking agent or force to the query protein and the composition, thereby crosslinking the query protein to the target moiety associated therewith;
   covalently binding the tag to a substrate, thereby covalently immobilizing the query protein and crosslinked target moiety on the substrate;
   washing the immobilized query protein and crosslinked target moiety under denaturing conditions, wherein the query protein remains immobilized on the substrate; and
   detecting the target moiety associated with the query protein after said washing.

2. The method of option 1, wherein the method is performed in multiplex, comprising two or more different query proteins, each comprising a different barcode.

3. The method of option 2, wherein the barcode comprises a polynucleotide comprising a coding sequence of the query protein.

4. The method of option 3, wherein the barcode comprises a covalent polypeptide tag fused to the polynucleotide, and wherein said covalent polypeptide tag is covalently bound to a counterpart polypeptide sequence on the query protein.

5. The method of option 4, wherein the counterpart polypeptide sequence is disposed at an N terminus of the query protein.

6. The method of any one of options 4-5, wherein the covalent polypeptide tag and counterpart polypeptide sequence comprise a Spytag and SpyCatcher; or Isopeptag and pilin-C; or SnoopTag and SnoopCatcher; or DogTag and SnoopTagJr; or SdyTag and SdyCatcher.

7. The method of any one of options 4-6, wherein providing the query protein comprises:
  fusing the covalent polypeptide tag to the polynucleotide encoding the query protein, wherein the counterpart polypeptide sequence is disposed at an N-terminal portion of the query protein;
  transcribing the polynucleotide in vitro, thereby producing the query protein comprising the counterpart polypeptide sequence disposed at the N-terminal portion and further comprising the tag; and
  covalently binding the polypeptide tag to the counterpart polypeptide sequence, thereby making the query protein comprising the tag and the barcode.

8. The method of any one of options 1-7, wherein the contacting and applying are in vivo.

9. The method of option 8, wherein providing the query protein comprising the tag comprises expressing a nucleic acid encoding the query protein comprising the tag in vivo.

10. The method of option 9, further comprising administering a vector comprising the nucleic acid encoding the query protein comprising the tag to a cell.

11. The method of any one of options 1-10, wherein:
  the tag comprises a haloalkane dehalogenase (such as a HaloTag tag) and the substrate comprises a haloalkane resin; or
  the tag comprises a DNA methyltransferase (such as a SNAP-tag) and the substrate comprises a benzylguanine resin; or
  the tag comprises a DNA methyltransferase (such as a CLIP-tag) and the substrate comprises a benzylcytosine resin; or
  the tag comprises an isopeptag (such as TDKDMTITFTNKKDAE—SEQ ID NO: 1) and the substrate comprises a pilin-C protein; or
  the tag comprises a SpyTag (such as AHIVMVDAYKPTK—SEQ ID NO: 2), and the substrate comprises a SpyCatcher protein; or
  the tag comprises SnoopTag (such as KLGDIEFIKVNK—SEQ ID NO: 3) and the substrate comprises a SnoopCatcher protein; or
  the tag comprises DogTag (such as DIPATYEFTDGKHYITNEPIPPK—SEQ ID NO: 4) and the substrate comprises SnoopTagJr; or
  the tag comprises SdyTag (such as DPIVMIDNDKPIT—SEQ ID NO: 5) and the substrate comprises SdyCatcher; or
  the tag comprises Cpe0147$_{565-587}$ and the substrate comprises Cpe0147$_{439-563}$.

12. The method of any one of options 1-11, wherein, the target moiety is a protein, a nucleic acid, or a protein-nucleic acid complex.

13. The method of any one of options 1-12, wherein the target moiety is an RNA.

14. The method of option 13, wherein the washing is at a temperature effective to fragment RNA, thereby fragmenting the target moiety.

15. The method of any one of options 13-14, wherein the target moiety is a rare RNA present in 200 or fewer copies per composition.

16. The method of any one of options 13-15, wherein the query protein is of unknown RNA binding specificity.

17. The method of any one of options 1-12, wherein the target moiety is a protein such as an RNA binding protein or complex, and the crosslinking agent comprises a protein-protein crosslinker 18. The method of any one of options 1-17, wherein detecting the target moiety comprises sequencing the target moiety or mass spectrometry.

19. The method of any one of options 1-18, wherein the composition comprises a sample.

20. The method of any one of options 1-19, wherein the composition further comprises a moiety from a different taxonomic species than the target moiety.

21. The method of any one of options 1-20, wherein the substrate comprises a magnetic bead 22. The method of any one of options 1-21, wherein the substrate does not comprise an immunoglobulin or binding fragment thereof.

23. The method of any one of options 1-22, wherein the crosslinking agent or force comprises ultraviolet radiation, or an amine-to-amine crosslinker (such as disuccinimidyl suberate or disuccinimidyl tartrate), or a sulfhydryl-to-sulfhydryl crosslinker (such as bis-maleimidoethane or dithiobis-maleimidoethane), or an aryl-azide (such as N-5-Azido-2-nitrobenzyloxysuccinimide or sulfosuccinimidyl 6-(4'-azido-2'-nitrophenylamino)hexanoate), or a diazirine (such as succinimidyl 4,4'-azipentanoate).

24. The method of any one of options 1-23, wherein the crosslinking agent comprises an agent selected from the group consisting of an NHS ester, an imidoester, a difluoro group, an NHS-haloacetyl group, an NHS-maleimide group, an NHS-pyridyldithiol group, a carbodiimide ester and NHS ester, a malemide and a hydrazine group, a pyridyldithiol and a hydrazine group, a NHS ester and an aryl azide, a NHS ester and a diazirine, a NHS ester and an aryl azide, an NHS ester and a diazirine.

25. The method of any one of options 1-24, wherein the denaturing conditions comprise a presence of a denaturants, a detergent, and/or a chaotropic salt, or temperatures of at least 60° C., 70° C., 80° C., 90° C., 100° C., 110° C., or 120° C.

26. The method of any one of options 1-25, wherein the washing is for no more than 60, 50, 40, 30, 20, or 10 minutes.

27. The method of any one of options 1-26, wherein covalently binding the tag to the substrate and washing are performed in a single container, such as a microcentrifuge tube, or well of a multi-well plate.

28. A composition comprising
  a query protein comprising a tag;
  a substrate, wherein the tag is covalently bound to the substrate;
  a target moiety crosslinked to the query protein;
  wherein the composition is under denaturing conditions.

29. The composition of option 28, the query protein further comprising a barcode comprising an polynucleotide comprising a coding sequence of the query protein.

30. The composition of option 29, wherein the barcode comprises a covalent polypeptide tag fused to the polynucleotide, and wherein said covalent polypeptide tag is covalently bound to a counterpart polypeptide sequence on the query protein.

31. The composition of option 30, wherein the counterpart polypeptide sequence is disposed at an N terminus of the query protein.

32. A kit comprising:
  a vector comprising an insertion site and a tag coding sequence, wherein the insertion site is arranged to place a query protein coding sequence in frame with the tag without any intervening stop codon, upon the insertion of the query protein coding sequence in the insertion site;

a substrate configured to specifically bind covalently to the tag; and a crosslinking agent.

33. The kit of option 32, further comprising a covalent polypeptide tag, wherein the vector further comprises a counterpart polypeptide coding sequence, arranged to dispose the counterpart polypeptide sequence at an N-terminal region of the query protein, upon the insertion of the query protein coding sequence in the insertion site, wherein the covalent polypeptide tag and the counterpart polypeptide sequence are configured to specifically covalently bind to each other.

34. The kit of any one of options 32-33, further comprising a denaturing agent.

35. The composition of any one of options 30-31, or the kit of any one of options 33-34, wherein the covalent polypeptide tag and counterpart polypeptide sequence comprise a Spytag and SpyCatcher; or Isopeptag and pilin-C; or SnoopTag and SnoopCatcher; or DogTag and SnoopTagJr; or SdyTag and SdyCatcher.

36. The composition of any one of options 28-31 or 35, or the kit of any one of options 32-35, wherein:

the tag comprises a haloalkane dehalogenase (such as a HaloTag tag) and the substrate comprises a haloalkane resin; or the tag comprises a DNA methyltransferase (such as a SNAP-tag) and the substrate comprises a benzylguanine resin; or the tag comprises a DNA methyltransferase (such as a CLIP-tag) and the substrate comprises a benzylcytosine resin; or the tag comprises an isopeptag (such as TDKDM-TITFTNKKDAE—SEQ ID NO: 1) and the substrate comprises a pilin-C protein; or the tag comprises a SpyTag (such as AHIVMV-DAYKPTK—SEQ ID NO: 2), and the substrate comprises a SpyCatcher protein; or the tag comprises SnoopTag (such as KLGDIEFIKVNK—SEQ ID NO: 3) and the substrate comprises a SnoopCatcher protein; or the tag comprises DogTag (such as DIPATYEFTDGKHYITNEPIPPK—SEQ ID NO: 4) and the substrate comprises SnoopTagJr; or the tag comprises SdyTag (such as DPIVMIDNDKPIT—SEQ ID NO: 5) and the substrate comprises SdyCatcher; or the tag comprises Cpe0147$_{565-587}$ and the substrate comprises Cpe0147$_{439-563}$.

37. The composition of any one of options 28-31 or 35-36, or the kit of any one of options 32-36, wherein the substrate comprises a magnetic bead.

38. The composition of any one of options 28-31 or 35-37, or the kit of any one of options 32-37, wherein the substrate does not comprise an immunoglobulin or binding fragment thereof.

39. The composition of any one of options 28-31 or 35-38, or the kit of any one of options 32-38, wherein the crosslinking agent comprises an amine-to-amine crosslinker (such as disuccinimidyl suberate or disuccinimidyl tartrate), or a sulfhydryl-to-sulfhydryl crosslinker (such as bis-maleimidoethane or dithio-bis-maleimidoethane), or an arylazide (such as N-5-Azido-2-nitrobenzyloxysuccinimide or sulfosuccinimidyl 6-(4'-azido-2'-nitrophenylamino)hexanoate), or a diazirine (such as succinimidyl 4,4'-azipentanoate).

40. The composition of any one of options 28-31 or 35-39, or the kit of any one of options 32-39, wherein the crosslinking agent comprises an agent selected from the group consisting of an NHS ester, an imidoester, a difluoro group, an NHS-haloacetyl group, an NHS-maleimide group, an NHS-pyridyldithiol group, a carbodiimide ester and NHS ester, a malemide and a hydrazine group, a pyridyldithiol and a hydrazine group, a NHS ester and an aryl azide, a NHS ester and a diazirine, a NHS ester and an aryl azide, and a diazirine.

EXAMPLES

Example 1: Human and Mouse Mixing Experiments Define PRC2-RNA Interactions that Occur in Solution after Cell Lysis To determine the level of PRC2-RNA interactions that are detected by CLIP that do not occur in vivo, we designed an experiment modeled after the classic Mili and Steitz experiment[52].

Specifically, we transfected individual V5 epitope tagged proteins into human cells and UV-crosslinked these cells to form covalent interactions between RNA and proteins that directly interact in vivo (+tag sample). We then lysed and mixed these human cells with lysate from UV-crosslinked mouse cells that did not contain the V5–tagged protein (–tag sample). In this mixed sample, we performed CLIP using an antibody against the V5–tagged protein and measured binding to human and mouse RNAs (FIG. 1A). We only analyzed sequencing reads that mapped uniquely and unambiguously to either the human or mouse genomes (See Material and Methods). In this system, any detected mouse RNA must represent an RNA-protein interaction that occurred after cell lysis because the immunoprecipitated V5–tagged protein is not present in these cells.

We focused on EZH2, SUZ12, and EED, 3 components of the PRC2 complex that have all been shown to bind directly and promiscuously to RNA by RIP[6,44,53-55], CLIP[13,14], and in vitro[22,26,51] experiments. We confirmed that these tagged proteins are properly incorporated into the endogenous PRC2 complex (FIG. 6) and that they still retain RNA binding activity in vitro (FIGS. 7A-G, Table 1).

TABLE 1

| Affinities of HaloTag-RNA Binding Proteins (RNPs) for RNA Determined by Biacore/SPR | | | | | | |
|---|---|---|---|---|---|---|
| HaloTag-GFP-V5 RNA | $k_a$ (1/Ms) | $k_d$ (1/s) | $K_D$ (M) | Rmax (RU) | Chi$^2$ (RU$^2$) | U-value |
| MBP | | | Binding Not Detectable | | | |
| MBP-BoxB | | | Binding Not Detectable | | | |
| HaloTag-GFP-3x LamdaN-V5 RNA | $k_a$ (1/Ms) | $k_d$ (1/s) | $K_D$ (M) | Rmax (RU) | Chi$^2$ (RU$^2$) | U-value |

TABLE 1-continued

Affinities of HaloTag-RNA Binding Proteins (RNPs) for RNA Determined by Biacore/SPR

| | $k_a$ (1/Ms) | $k_d$ (1/s) | $K_D$ (M) | Rmax (RU) | Chi$^2$ (RU$^2$) | U-value |
|---|---|---|---|---|---|---|
| MBP | Binding Not Detectable | | | | | |
| MBP-BoxB | 29700 ± 160 | 0.0012 ± 0.00003 | 3.93E−08 | 1.6 ± 0.005 | 0.0113 | 12 |
| HaloTag-PTBP1-V5 | | | | | | |
| RNA | $k_a$ (1/Ms) | $k_d$ (1/s) | $K_D$ (M) | Rmax (RU) | Chi$^2$ (RU$^2$) | U-value |
| MBP | 567 ± 42 | 0.0049 ± 0.0001 | 8.68E−06 | 9.5 ± 0.7 | 0.0049 | 20 |
| MBP-BoxB | 51900 ± 920 | 0.0054 ± 0.0001 | 1.04E−07 | 0.5 ± 0.005 | 0.0045 | 9 |
| Xist A-repeat | 26000 ± 330 | 0.0068 ± 0.00009 | 2.61E−07 | 1.0 ± 0.008 | 0.0045 | 5 |
| Xist E-repeat | 63600 ± 750 | 0.0038 ± 0.00007 | 5.96E−08 | 0.7 ± 0.004 | 0.0078 | 9 |
| HaloTag-EZH2-V5 | | | | | | |
| RNA | $k_a$ (1/Ms) | $k_d$ (1/s) | $K_D$ (M) | Rmax (RU) | Chi$^2$ (RU$^2$) | U-value |
| MBP | 1510 ± 48 | 0.088 ± 0.0009 | 5.81E−05 | 78 ± 2 | 0.0062 | 15 |
| MBP-BoxB | 468 ± 29 | 0.031 ± 0.0003 | 6.60E−05 | 79 ± 5 | 0.0081 | 15 |
| Xist A-repeat | 992 ± 62 | 0.056 ± 0.0006 | 5.60E−05 | 79 ± 5 | 0.0082 | 15 |
| Xist E-repeat | 1670 ± 420 | 0.022 ± 0.0002 | 1.32E−05 | 21 ± 5 | 0.0123 | 20 |
| HaloTag-EED-V5 | | | | | | |
| RNA | $k_a$ (1/Ms) | $k_d$ (1/s) | $K_D$ (M) | Rmax (RU) | Chi$^2$ (RU$^2$) | U-value |
| MBP | 19900 ± 580 | 0.033 ± 0.0003 | 1.63E−06 | 3.4 ± 0.07 | 0.0076 | 9 |
| MBP-BoxB | 12300 ± 490 | 0.036 ± 0.0003 | 2.94E−06 | 6.1 ± 0.2 | 0.0074 | 20 |
| Xist A-repeat | 25100 ± 440 | 0.0064 ± 0.00005 | 2.57E−07 | 2.2 ± 0.03 | 0.0076 | 5 |
| Xist E-repeat | 15800 ± 960 | 0.017 ± 0.00009 | 1.10E−06 | 3.6 ± 0.06 | 0.0157 | 7 |
| HaloTag-SUZ12-V5 | | | | | | |
| RNA | $k_a$ (1/Ms) | $k_d$ (1/s) | $K_D$ (M) | Rmax (RU) | Chi$^2$ (RU$^2$) | U-value |
| MBP | 47100 ± 2000 | 0.063 ± 0.0001 | 1.35E−06 | 4.2 ± 0.1 | 0.0192 | 7 |
| MBP-BoxB | 835 ± 64 | 0.081 ± 0.001 | 9.66E−05 | 290 ± 21 | 0.0083 | 15 |
| Xist A-repeat | 94100 ± 15000 | 0.17 ± 0.006 | 1.79E−06 | 11 ± 1.6 | 0.0333 | 26* |
| Xist E-repeat | 1850 ± 77 | 0.11 ± 0.002 | 6.06E−05 | 140 ± 5.3 | 0.0281 | 15 |

Figure 1D:
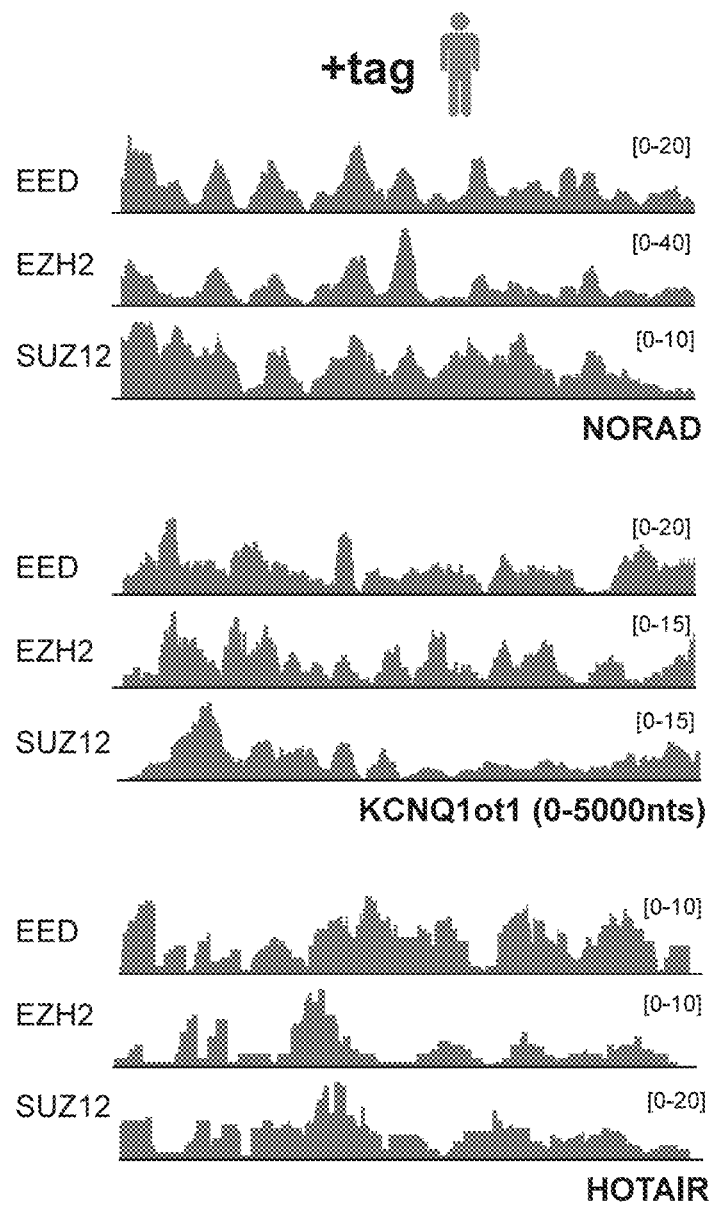

We performed CLIP in the mixed samples and observed that the majority of expressed RNAs are significantly enriched for binding of all 3 PRC2 components in the +tag samples relative to their expression levels in total RNA (~65%, p<10$^{-6}$, FIGS. 1B-C, FIGS. 8A-F). For example, we observe strong enrichment for all 3 PRC2 components across several lncRNAs that have previously been reported to bind to PRC2 including HOTAIR[3,7,10], KCNQ1ot1[9,56-58], and TUG1[3,54] (FIG. 1D). In addition, we observed strong binding across NORAD, a lncRNA that is predominantly localized in the cytoplasm[59,60] (FIG. 1D). To ensure that these broad RNA binding profiles are not merely caused by overexpression of the tagged PRC2 components, we performed CLIP in untransfected cells using antibodies that recognize the endogenous PRC2 components. We observe that the vast majority of the RNA regions identified in the V5 samples are also enriched in the endogenous samples (~85%, FIG. 9) and all 3 PRC2 components demonstrate a similar broad RNA binding profile (FIGS. 8A-F).

Figure 1E:
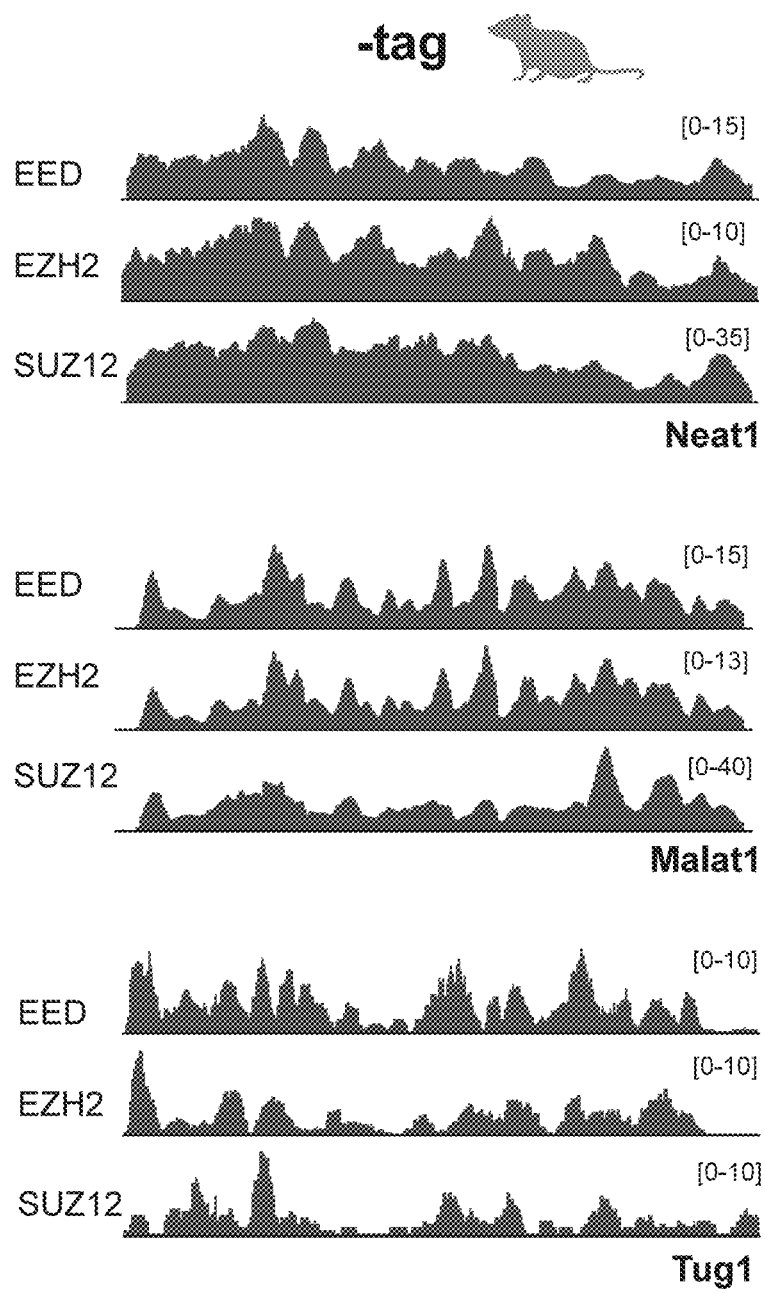

Surprisingly, we also consistently observed significant PRC2 binding in the −tag samples with >4,500 mouse RNAs identified as significantly enriched for at least one of the 3 PRC2 components (FIGS. 1B-C, FIGS. 2B-G). In fact, numerous lncRNAs that have been reported as in vivo interaction partners of PRC2 show significant binding for all 3 PRC2 components in the −tag samples, including Tug1, Meg3, Malat1, and Neat1[6,14,15,53,54] (FIG. 1E).

These results demonstrate that thousands of PRC2-RNA interactions can be detected by CLIP even when they do not actually occur in vivo. While the presence of strong PRC2-RNA binding in solution does not preclude the possibility that these PRC2 components also bind to RNA in vivo, it highlights the challenge in accurately determining which of the detected PRC2-RNA interactions may represent bona fide interactions that occur in vivo using conventional methods.

Figure 2A:
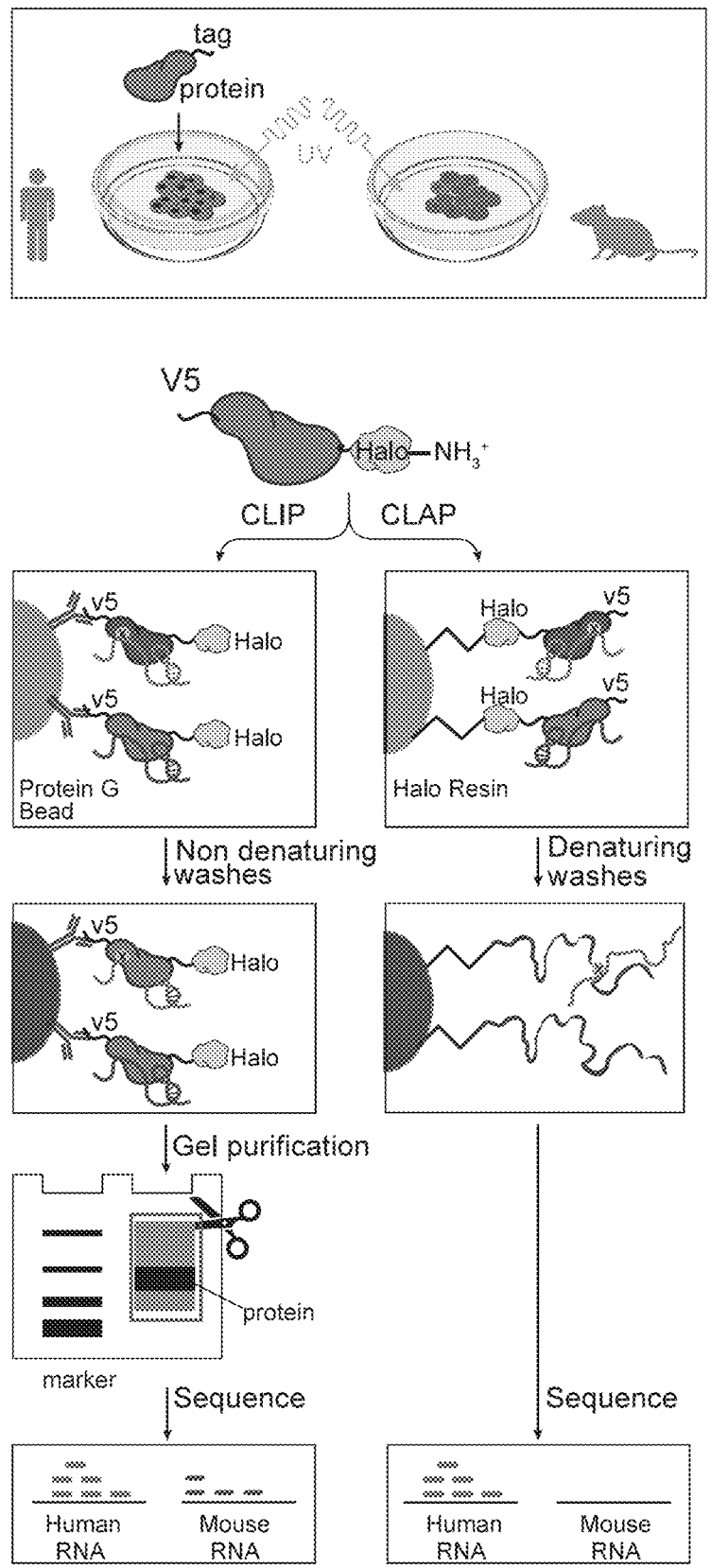
FIGS. 2A-2J are a series of graphs showing that CLAP removes RNA-protein interactions that do not occur in vivo, in accordance with some embodiments.
Figures 2B, 2C:
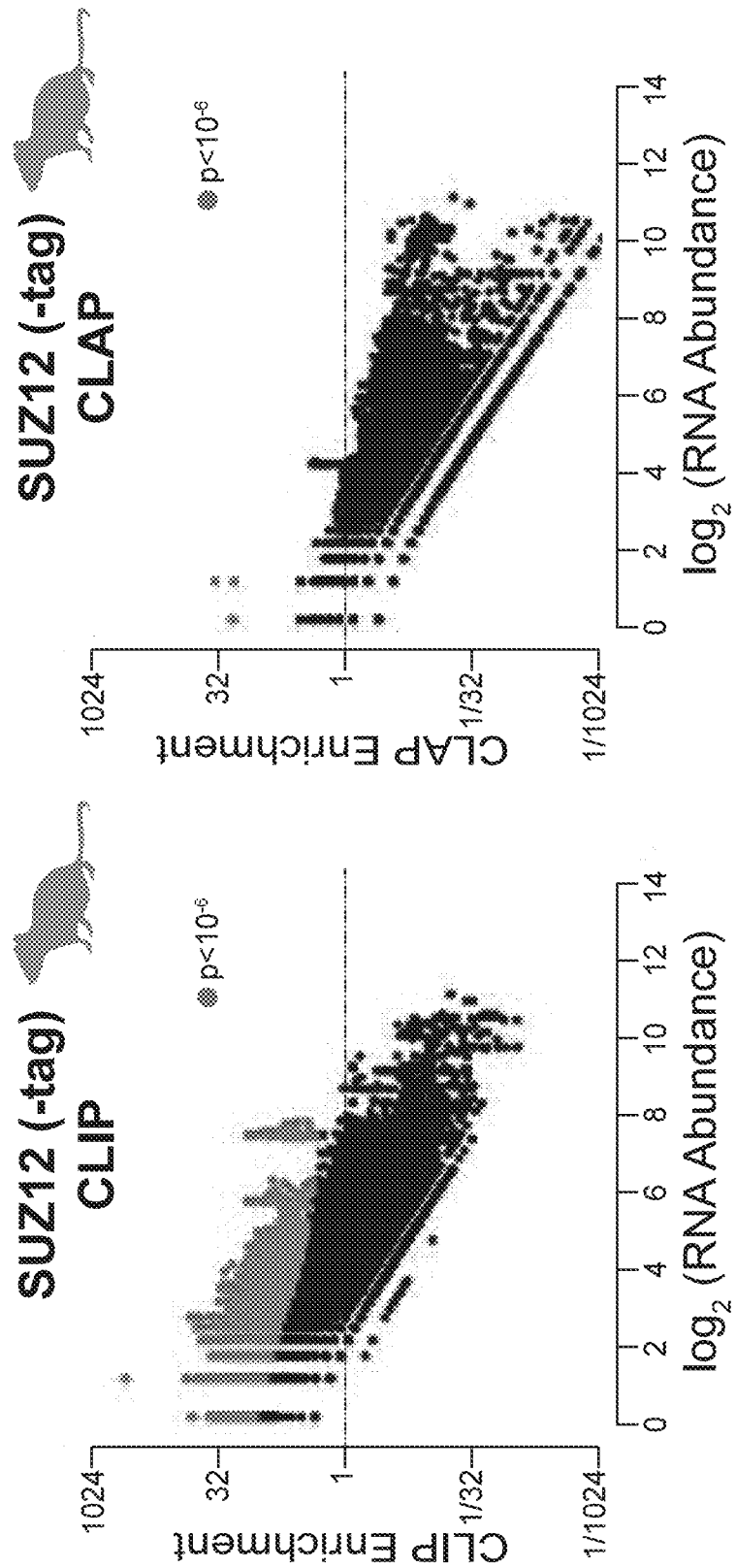
Figure 2E:
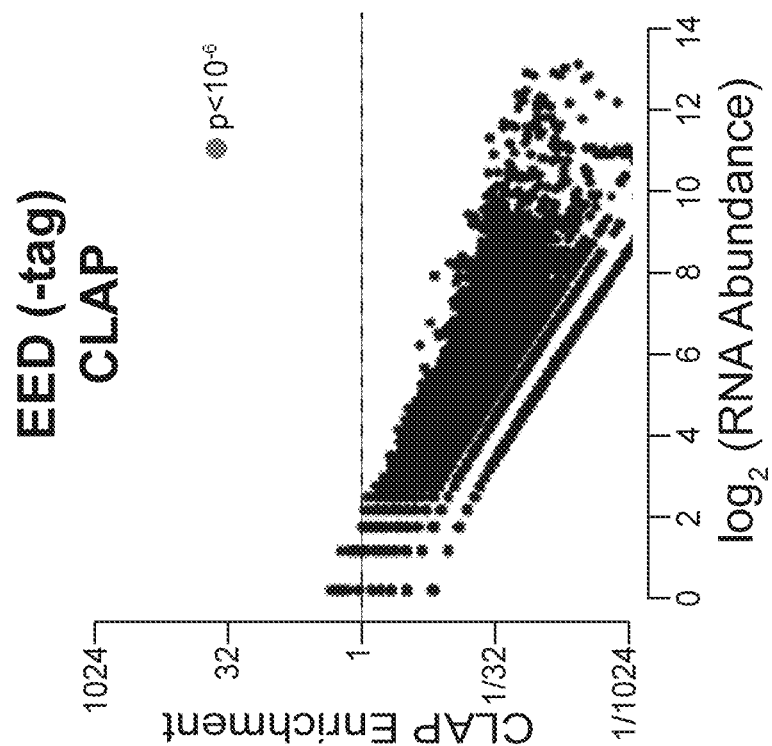
Figure 2D:
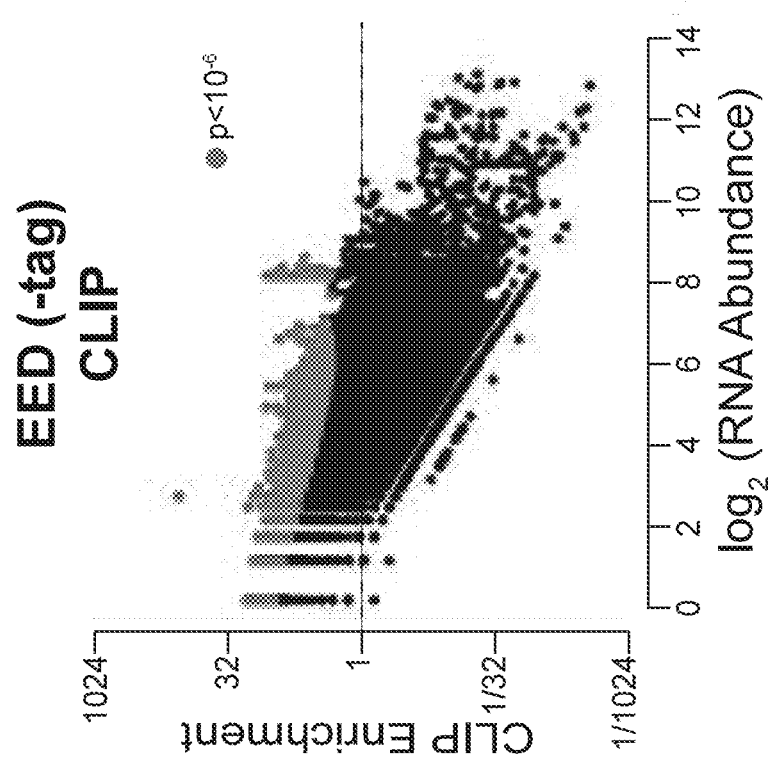
Figure 2G:
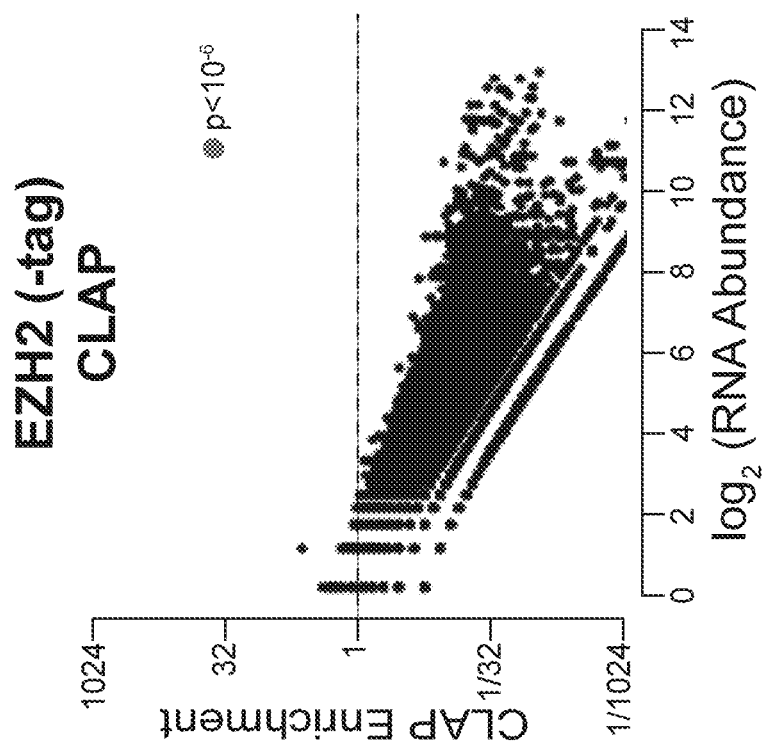
Figure 2F:
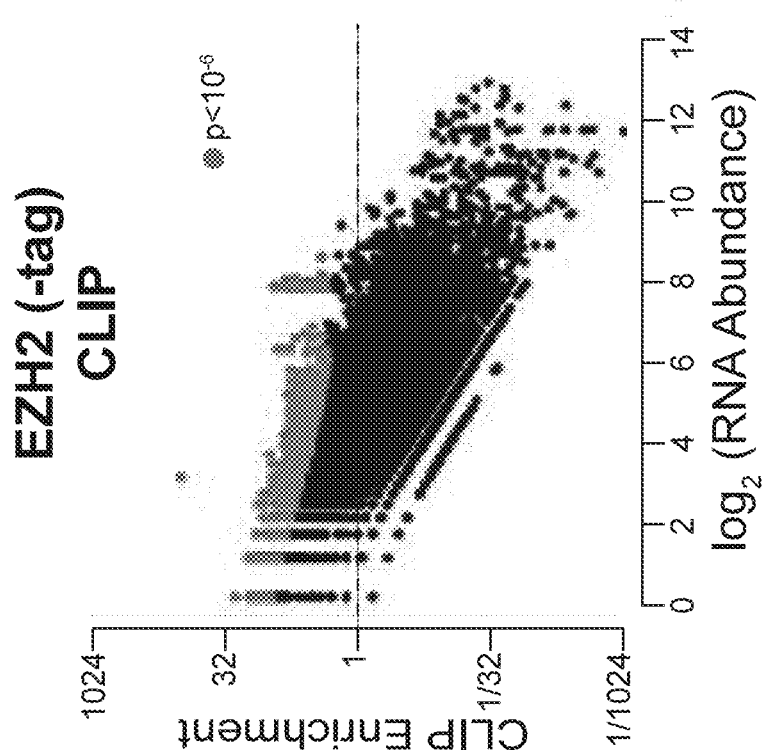

Example 2: Covalent Linkage and Affinity Purification (CLAP): A Denaturing Purification Method that Removes RNA-Protein Interactions that do not Occur In Vivo Without being limited by theory, we considered several scenarios that could lead to the detection of RNA-protein interactions that do not occur in vivo: (i) the captured protein may interact directly with RNA in solution and this RNA could even be crosslinked to a distinct protein, (ii) the captured protein may associate in solution with other proteins that are crosslinked to RNA, or (iii) other proteins that are crosslinked to RNA may still be retained after immunoprecipitation (FIGS. 10A-F). Any of these non-specific interactions that remain after immunoprecipitation would be detected because the protein purification (immunoprecipitation) and denaturation steps (gel electrophoresis) are decoupled in the CLIP procedure (FIG. 2A). While it is clear that in vivo crosslinked RNA-protein interactions are strongly enriched by CLIP[45-749,61-63], these sources of background binding may be especially problematic when a protein does not actually bind to RNA (or binds to rare RNA targets) in vivo because non-specific RNA targets will be present in vast excess relative to bonafide targets (See Note 1).

To address these issues, we developed a new method called Covalent Linkage and Affinity Purification (CLAP) that enables purification of RNA-protein interactions using fully-denaturing conditions (FIG. 2A). CLAP uses HaloTag fusion proteins that enable covalent coupling of the tagged protein to a resin. Because the tagged protein is covalently coupled to the resin, rather than captured through an antibody, we can use a purification procedure that employs fully denaturing conditions—including high temperatures, high concentrations of denaturants and detergents, and chaotropic salts—that disrupt protein folding and RNA folding (see Methods).

This procedure directly couples protein purification and denaturation and accordingly the only RNA-protein interactions that should remain are those that represent the protein of interest where the RNA is covalently crosslinked in vivo. Indeed, we find that CLAP increases the specificity of protein purification and dramatically increases the separation of crosslinked RNA-protein complexes from free RNA relative to CLIP conditions (See Note 1, FIGS. 10A-F).

To test whether CLAP reduces RNA-protein associations that occur in solution, we performed a mixing experiment where we expressed proteins fused to both Halo and V5 tags in human cells (+tag) and mixed them with untransfected mouse cells (-tag). We then split the lysate and performed CLIP and CLAP captures from the same mixture allowing us to directly compare the contribution of in solution associations in each experiment (FIG. 2A). For each protein, we performed at least 2 independent replicate experiments and observed virtually identical results for both replicates (FIGS. 11A-L).

Figure 2H:
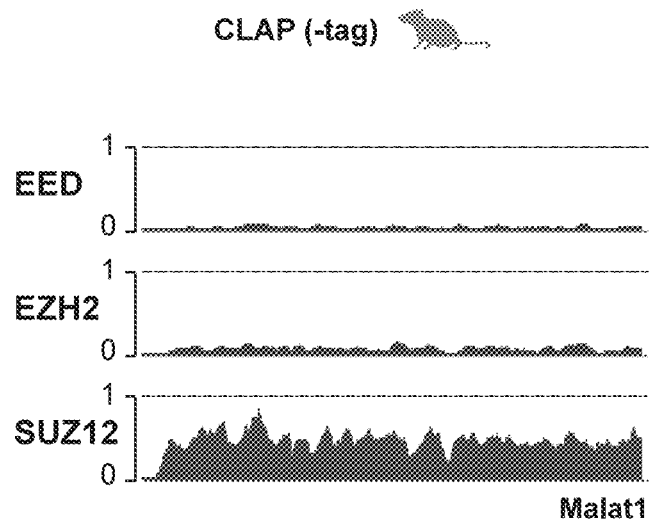
Figure 2I:
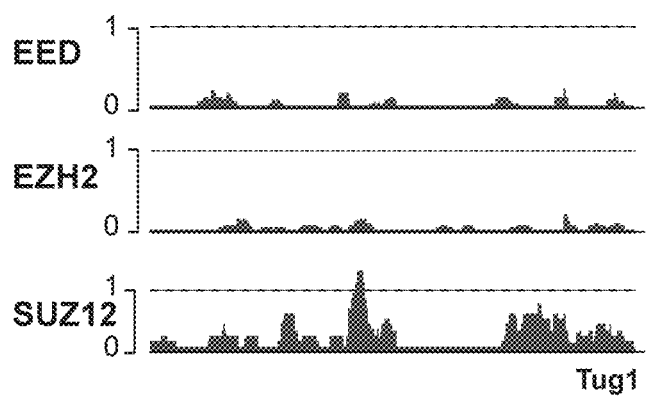
Figure 2J:
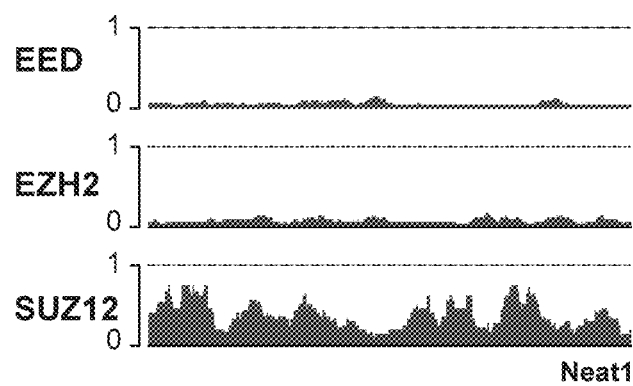

In the -tag samples, CLAP led to greatly reduced levels of background associated RNA for all 3 of the PRC2 proteins relative to V5 CLIP (FIGS. 2B-G). In fact, virtually all of the RNA regions that were significantly enriched in the -tag CLIP samples were depleted when measured by CLAP (>99.9%, FIGS. 2B-G). For example, the Tug1, Malat1, and Neat1 lncRNAs that were identified as enriched for PRC2 binding in the -tag samples using CLIP are depleted when measured by CLAP (FIGS. 2H-J). These results demonstrate that CLAP accurately removes RNA-protein interactions that do not occur in vivo.

Example 3: CLAP Accurately Identifies RNA-Protein Interactions that are Crosslinked In Vivo To ensure that CLAP can still identify bona fide RNA-protein interactions that occur in vivo, we focused on two well-defined RNA binding proteins (RBPs) that are known to interact with RNA through distinct binding modes: (i) PTBP1 is an RBP that contains multiple RNA Recognition Motif (RRM) domains, binds predominately within intronic regions, and has high selectivity towards a defined RNA sequence motif (HYUUUYU)[64] and (ii) SAF-A (also known as hnRNPU) is an RNA binding protein that contains tandem RGG motifs and binds to nascent pre-mRNA with broad affinity and a promiscuous binding profile[65]. For each protein, we performed CLIP and CLAP from the same mixed human and mouse samples.

Figure 3B:
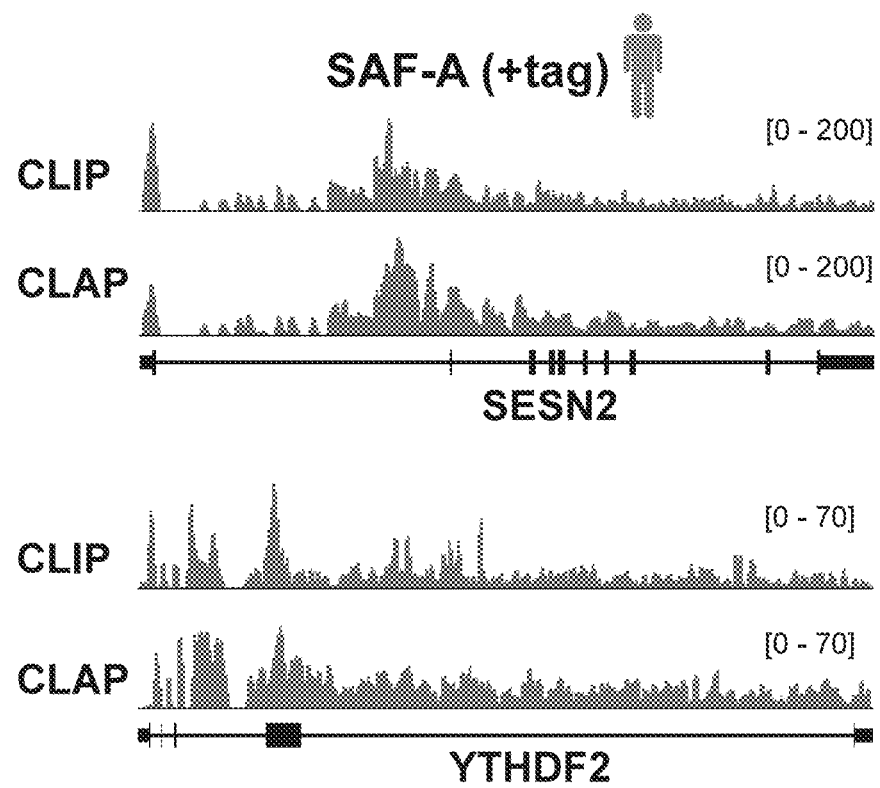
Figure 3C:
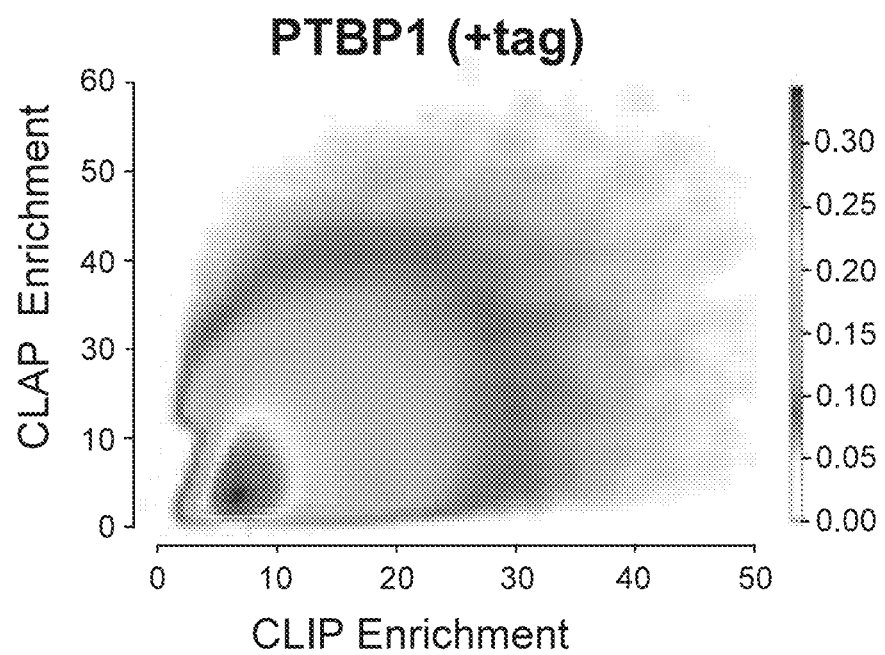
Figure 3D:
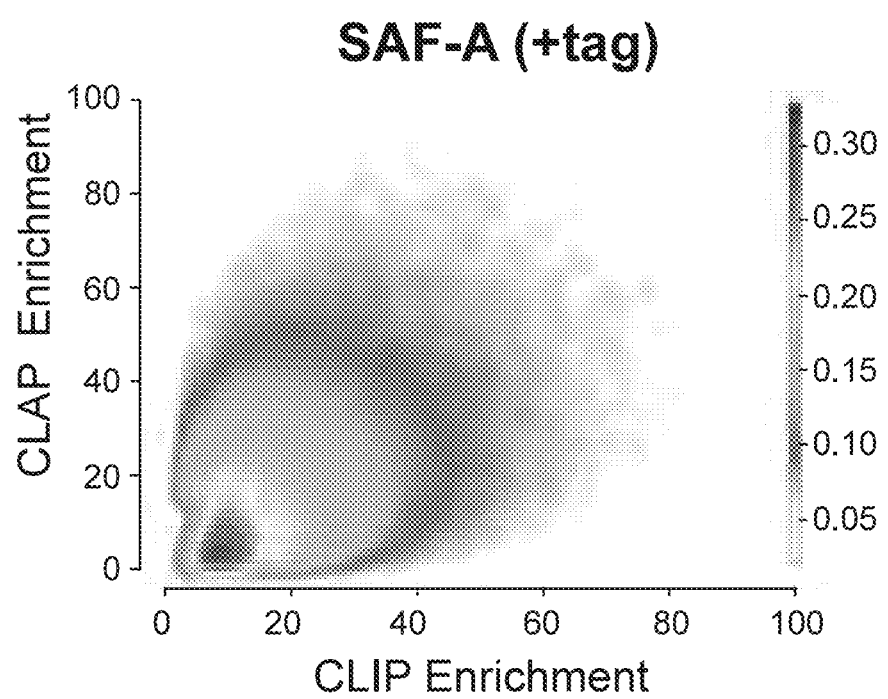
Figure 3E:
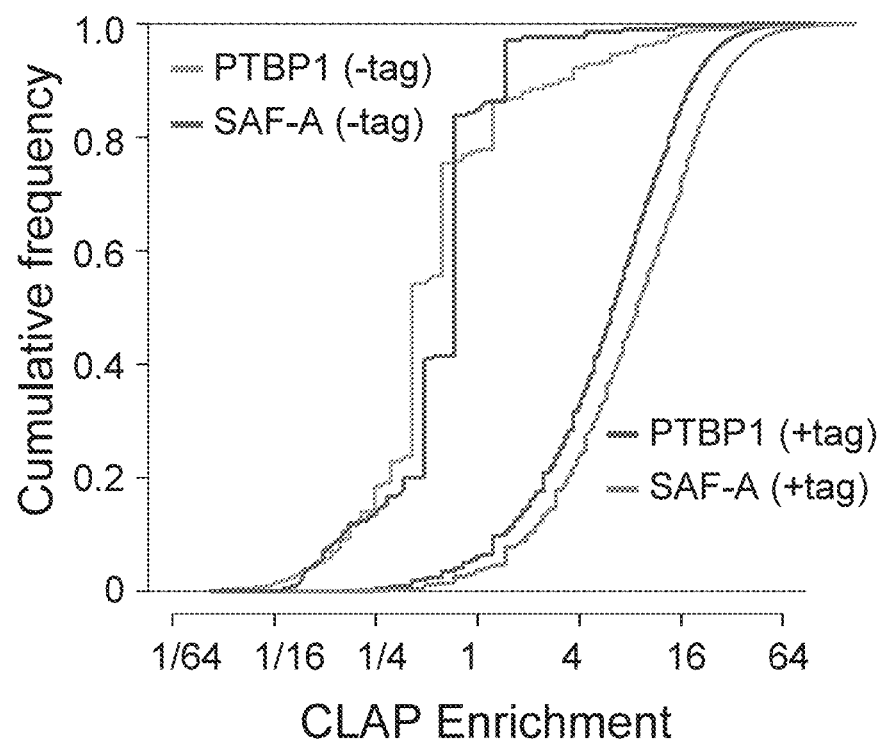
Figure 3F:
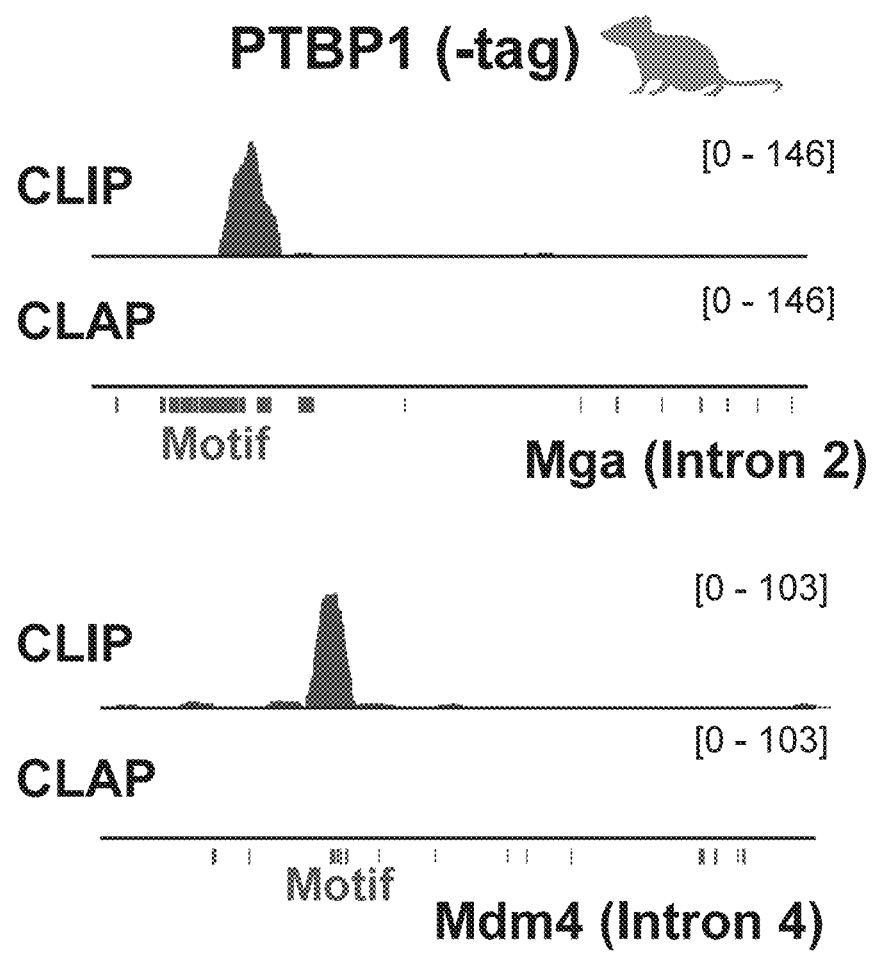
FIG. 3F is a graph showing examples of CLIP (top) and CLAP (bottom) enrichments are plotted for PTBP1 over intronic regions of mouse mRNAs (−tag). The locations of the corresponding PTBP1 recognition motif (blue boxes) are shown.

Using CLIP, we observed the expected profiles in the +tag samples with PTBP1 binding primarily at intronic regions containing the known PTBP1 sequence motifs (FIG. 3A) and SAF-A binding predominantly across nascent pre-mRNAs (FIG. 3B). In fact, virtually all of the identified RNA regions are also identified as enriched when we perform CLIP using antibodies recognizing the endogenous proteins (~99.8%, FIG. 9). When we perform CLAP, we observed comparable levels of enrichment for PTBP1 and SAF-A as observed by CLIP in the +tag samples (FIGS. 3C-D). In the case of PTBP1, we identified the well-defined RNA sequence motif within the RNA regions that were significantly enriched by CLIP or CLAP (see Methods). In fact, the vast majority of the RNA regions that were significantly enriched in the CLIP samples for PTBP1 and SAF-A are still enriched in the CLAP samples (~88%, FIG. 3E). While we observe similar binding profiles for CLIP and CLAP in the +tag samples, we observe a few RNA regions that are significantly enriched in the -tag samples by CLIP virtually all of which are removed by CLAP (FIGS. 3E-F, FIGS. 12A-D).

These results demonstrate that CLAP identifies RNA-protein interactions that are crosslinked in vivo and excludes interactions that occur in solution. While it is clear that CLIP accurately identifies RNA-protein interactions that occur in vivo for bona fide RNA binding proteins, CLAP may provide a more appropriate method when exploring proteins with unknown RNA binding specificity because it more robustly excludes interactions that do not occur in vivo. In addition, CLAP has several other features: it achieves increased sensitivity for detecting interactions that occur with rare transcripts because it reduces background binding, takes significantly less time to perform because it does not require gel extraction, allows for fragmentation of RNA using heat thereby eliminating structural biases associated with RNase digestion, and can be used with protein-protein crosslinking reagents to define protein complexes that interact with RNA (See Note 2).

Example 4: CLAP Distinguishes Bona Fide XIST Interacting Proteins from in Solution Associations Having developed a method that removes RNA-protein interactions that do not occur in vivo, we explored protein binding to the XIST lncRNA. We focused on SHARP (also called Spen), SAF-A, and PTBP1 because they have been identified by several independent groups as in vivo binding partners of XIST when purified under denaturing conditions[33,36,37], have well-established RNA binding domains, and display different binding patterns to the XIST RNA (structure dependent binding, promiscuous binding, and sequence specific binding, respectively)[36,66,67].

SHARP and SAF-A have been shown to be essential for XIST-mediated transcriptional silencing[33,36,38,39]. In addition, we explored 3 components of the PRC2 complex (EZH2, SUZ12, and EED), which have been shown to bind to XIST by RIP, CLIP, and in vitro experiments[5,6,26,55].

Figure 4B:
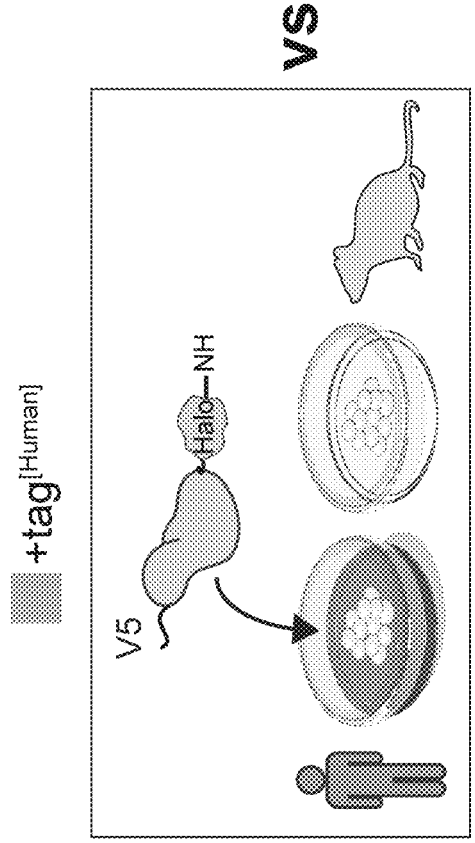
FIGS. 4A-C is a series of graphs showing that CLAP distinguishes bona fide XIST interacting proteins from associations that occur in solution after lysis.
Figure 4A:
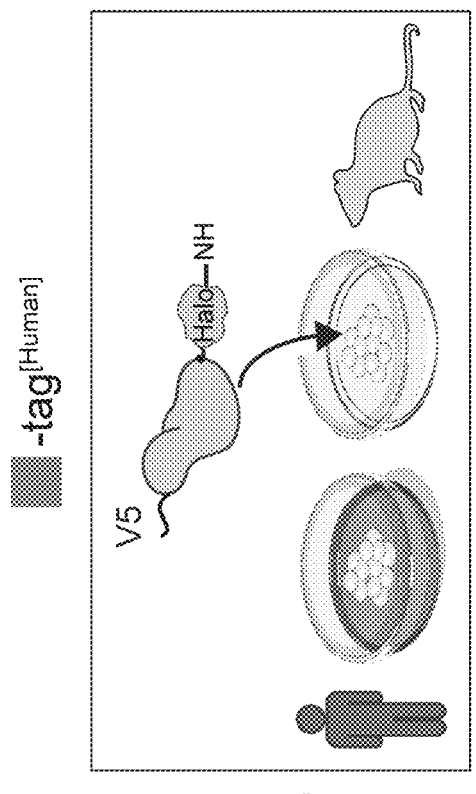

In order to directly compare the levels of specific and non-specific protein binding to the same RNA, we transfected each of these 6 tagged proteins into a female human cell line that expresses XIST (+tag$^{[Human]}$) and mixed them with untransfected mouse cells. In parallel, we transfected these proteins into a male mouse cell line and mixed them with untransfected human cells (-tag$^{[Human]}$). We then performed CLIP and CLAP in these two sets of mixed samples and directly compared protein binding on human XIST in the transfected (+tag$^{[Human]}$) and untransfected (-tag$^{[Human]}$) sets (FIGS. 4A-B).

Figure 4C:
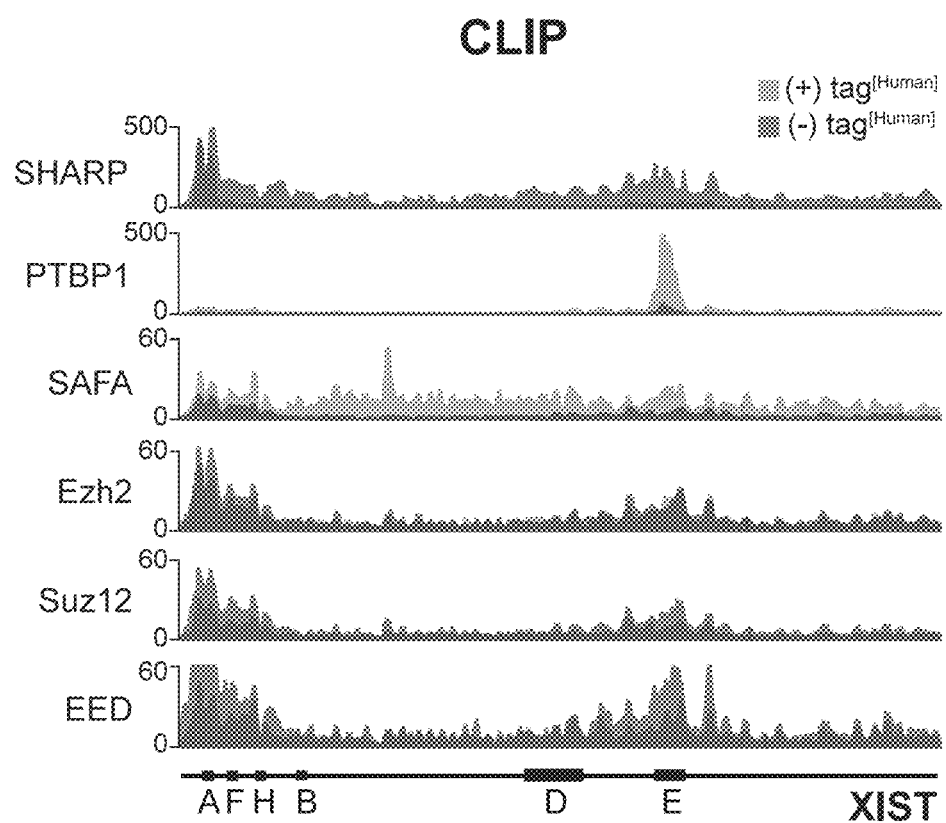
Figures 13A, 13B:
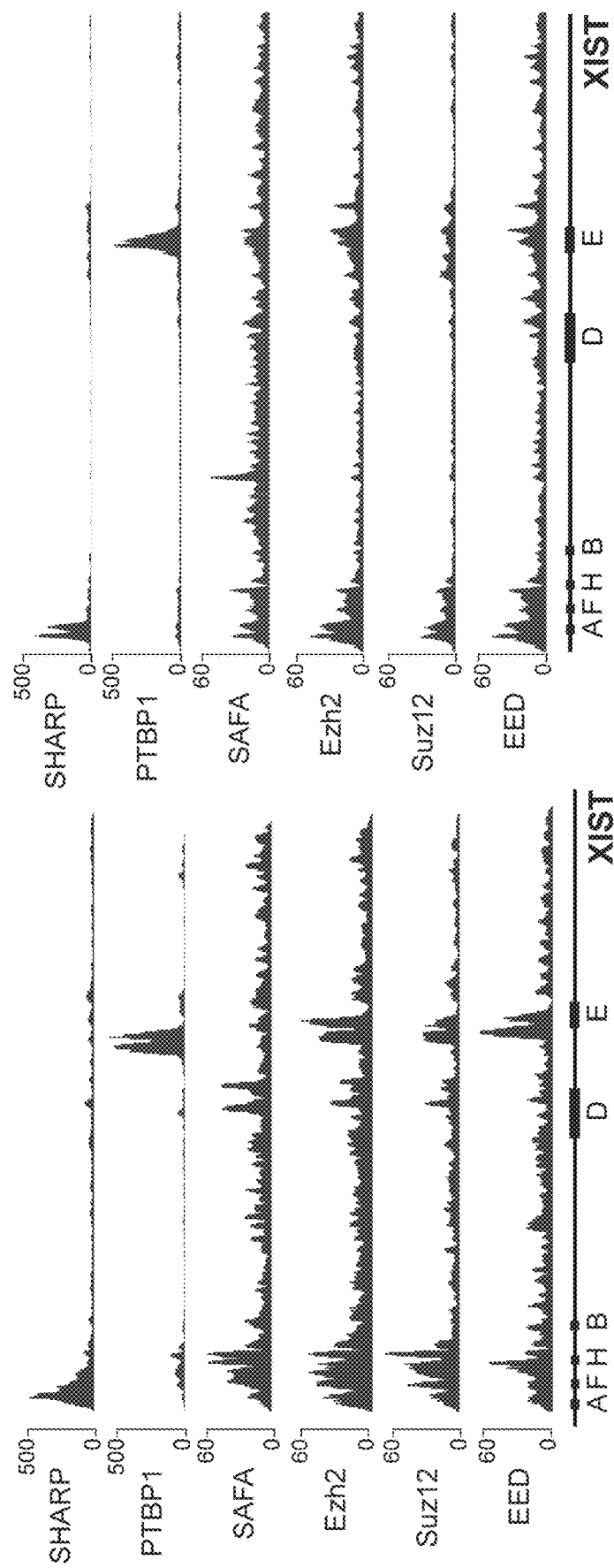
FIGS. 13A-B are a series of graphs showing that CLIP of endogenous proteins and V5 tagged proteins display similar binding profiles to XIST. CLIP enrichments for each protein mapped using an antibody raised against the endogenous (untransfected) protein are plotted over each nucleotide of the human Xist RNA (FIG. 13A) and compared to CLIP enrichments performed on V5-tagged proteins (FIG. 13B). The rows show CLIP enrichments for SHARP, PTBP1, SAF-A, EZH2, SUZ12, and EED proteins, respectively. The locations of the different Xist repeat annotations are shown (bottom).
Figure 14A:
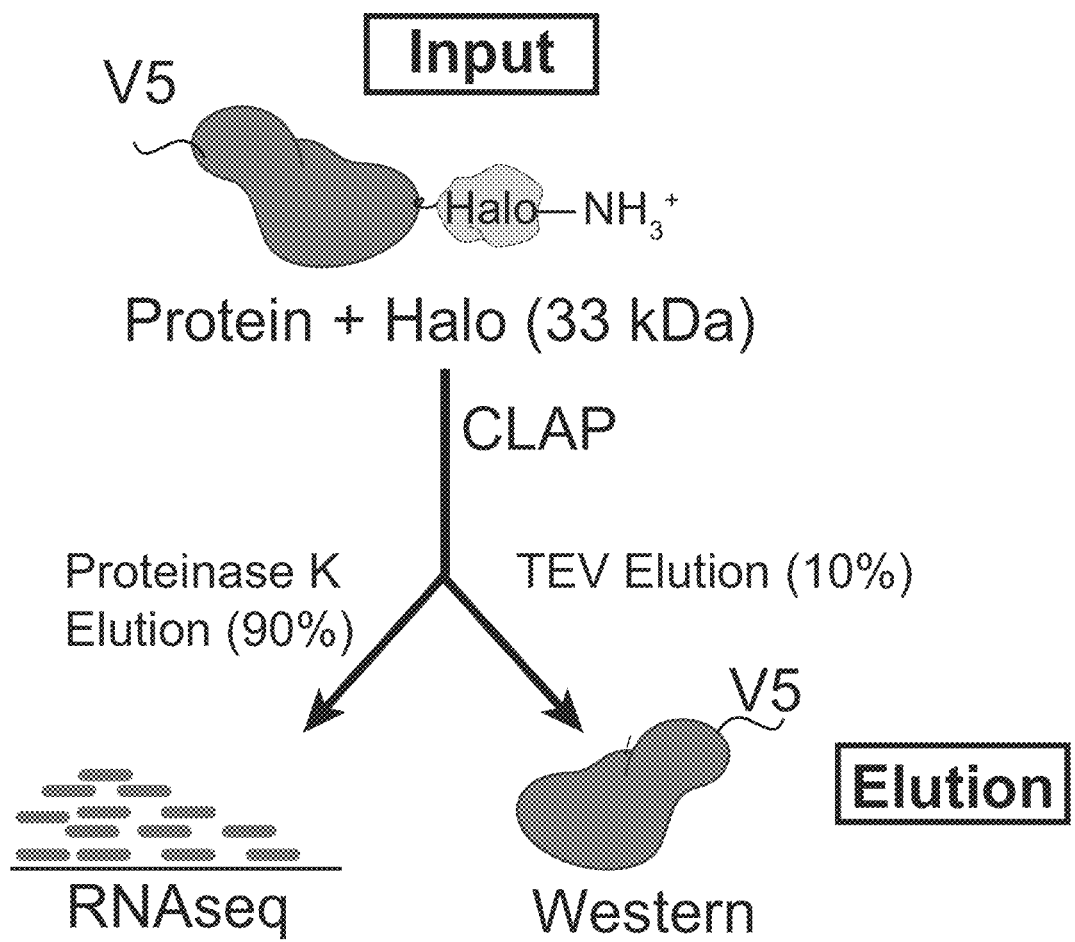
FIGS. 14A-D are a series of schematic diagrams and images showing that CLAP successfully captures the PRC2 components. A schematic of the CLAP procedure and elution of the tagged protein using TEV protease. A protein sample from the input prior to CLAP enrichment ("input") was saved and run alongside a protein sample that was taken after CLAP enrichment ("elution"). The input and elution samples were run alongside each other and quantified. In all cases, the protein was successfully captured with high efficiency. Note: The shift in band size from input to elution represent the TEV cleavage of the HaloTag protein (33 kDa).
Figures 14B, 14C, 14D:
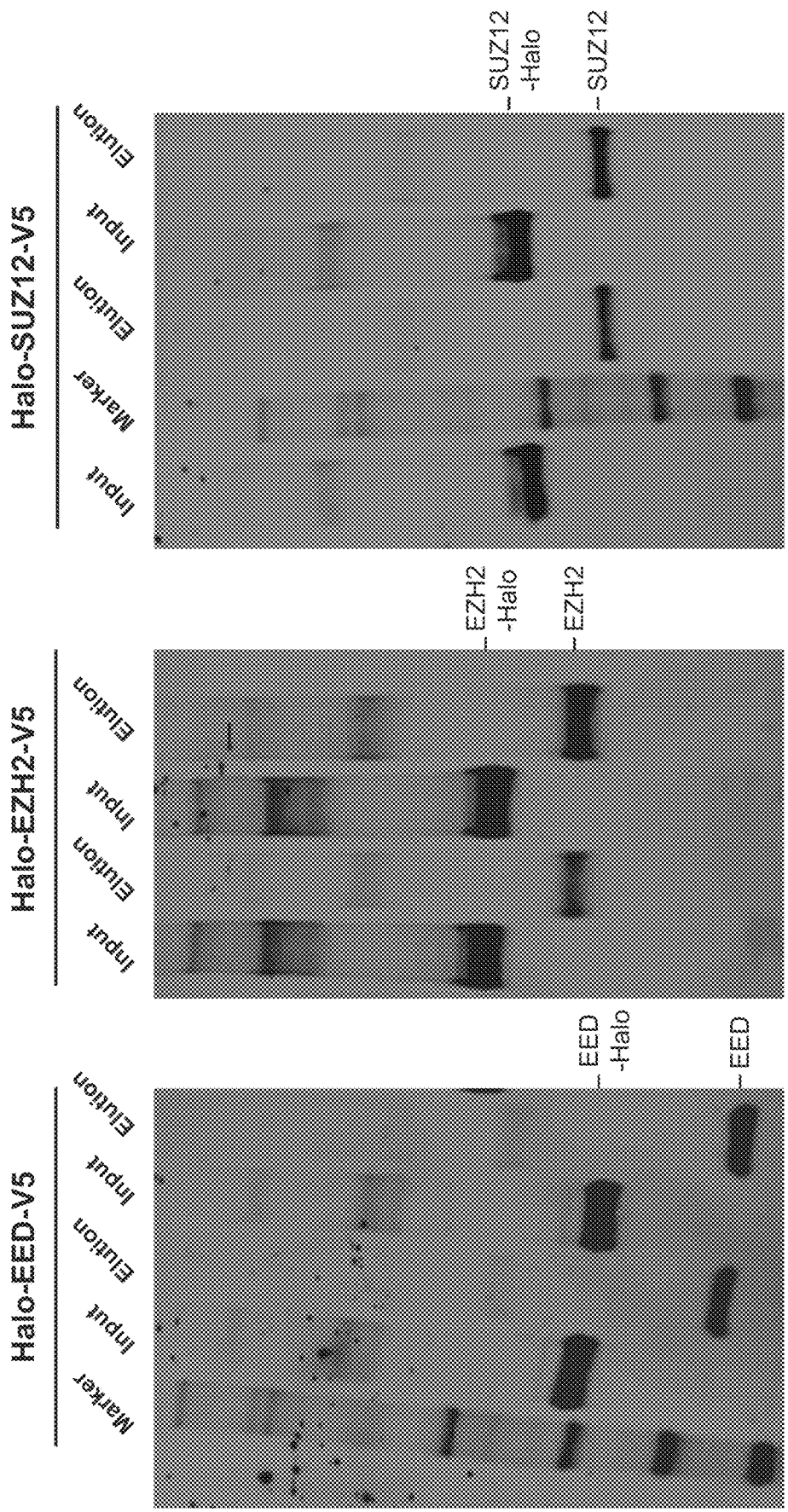
Figure 15B:
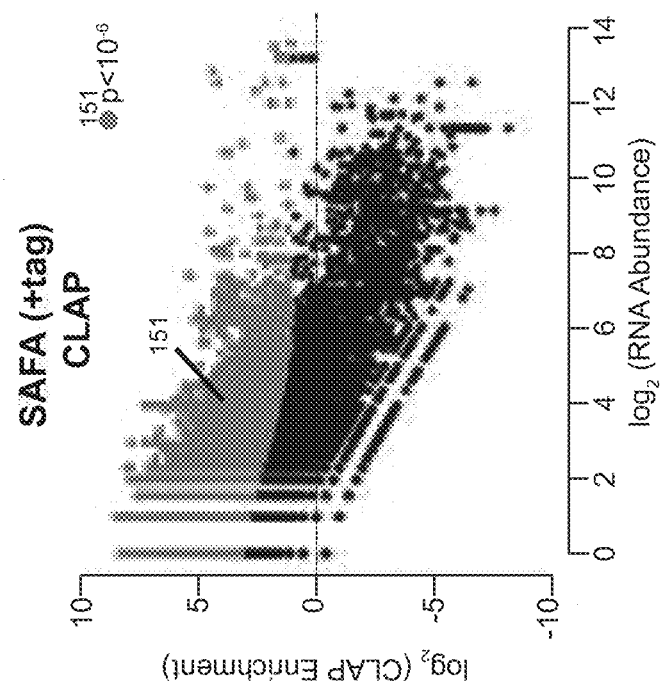
FIGS. 15A-B are a series of graphs showing that SAF-A demonstrates broad binding to many RNAs in CLIP and CLAP captures. Scatter plot of RNA abundance compared to the CLIP (FIG. 15A) or CLAP enrichment (FIG. 15B) for SAF-A across all 100-nucleotide windows of annotated human RNAs (+tag).
Figure 15A:
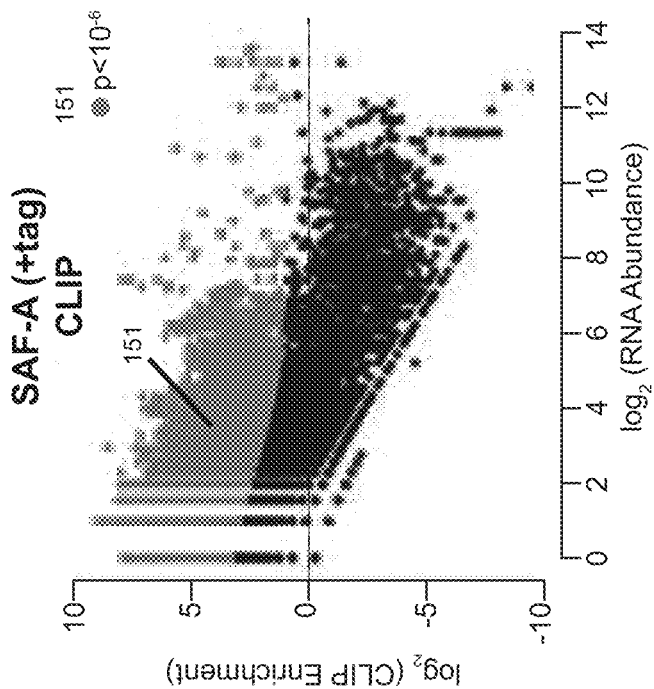

In the CLIP samples, we identified binding profiles in the +tag$^{[Human]}$ samples that were consistent with previous reports: SHARP was strongly enriched over the A-repeat region[36,66-68], PTBP1 was strongly enriched over the E-repeat region[67,68], and SAF-A bound broadly across XIST[68]. Furthermore, the 3 PRC2 components showed highly comparable profiles to each other, displaying broad enrichment across Xist with the strongest enrichment being over the A-repeat region as previously reported[5,6] (FIG. 4C). In all cases, the RNA binding profiles observed were highly comparable to the profiles obtained when performing CLIP with antibodies recognizing the endogenous proteins (FIGS. 13A-B). Interestingly, we also observed comparable binding profiles in the −tag$^{[Human]}$ samples (Pearson correlation >0.85, FIG. 4C). However, the level of enrichment varied dramatically relative to the +tag$^{[Human]}$ samples for the different proteins. For example, PTBP1 bound to the E-repeat region in both samples, but showed an ~10-fold increased enrichment in the +tag$^{[Human]}$ relative to the −tag$^{[Human]}$ samples. By comparison, SAF-A is enriched across most of the XIST RNA in the +tag$^{[Human]}$ samples, but shows comparably high enrichments only over a few specific regions in the −tag$^{[Human]}$ samples. In contrast, SHARP binds to the A-repeat of XIST with comparable enrichment in both the +tag$^{[Human]}$ and −tag$^{[Human]}$ samples (FIG. 4C). Similarly, the 3 PRC2 components bind with comparable enrichment to the A-repeat region and the remainder of XIST in both the +tag$^{[Human]}$ and −tag$^{[Human]}$ samples. The fact that SHARP and PRC2 bind to XIST with comparable enrichment in the +tag$^{[Human]}$ and −tag$^{[Human]}$ samples indicates that these associations can occur in solution after lysis, but it does not exclude the possibility that these interactions may also occur in vivo.

Figure 4D:
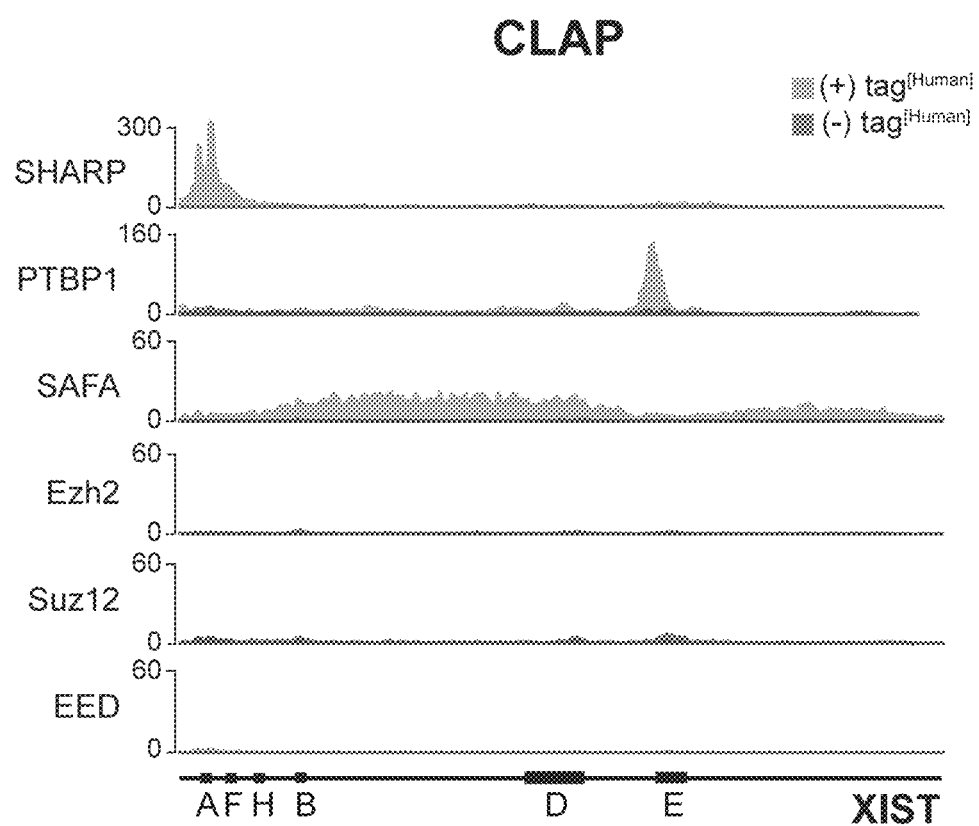
FIG. 4D is a graph showing CLAP enrichments for each protein in the +tag$^{[Human]}$ (red) or −tag$^{[Human]}$ (blue) samples are overlaid and plotted over each nucleotide of the human XIST RNA. The rows show CLIP enrichments for SHARP, PTBP1, SAF-A, EZH2, SUZ12, and EED proteins, respectively. The locations of the different XIST repeat annotations are shown (bottom).

In the CLAP samples, we observe negligible binding of all 6 proteins to XIST in the −tag$^{[Human]}$ samples (FIG. 4D). In contrast, in the +tag$^{[Human]}$ samples, we observed different binding patterns for each of the proteins. For SHARP and PTBP1, we observe a strong enrichment over XIST with binding patterns that closely resembled the profiles observed by CLIP (FIG. 4D). For SAF-A, we observed broad binding across Xist, but depletion over a region around the A-repeat and E-repeat of XIST. Interestingly, we observed no enrichment for any of the 3 PRC2 components over any region of XIST (FIG. 4c) even though the Halo-tagged proteins were successfully purified in each of these experiments (FIG. 14A-D), the number of sequencing reads generated were comparable across all experiments (CLIP and CLAP for all proteins) (Table 2), the Halo-tagged proteins were properly incorporated into the endogenous PRC2 complex (FIG. 6), and the tagged PRC2 proteins still retain RNA binding activity in vitro (FIGS. 7A-G, Table 1).

TABLE 2

Total number of reads that were sequenced for each sample. The number of reads here represent the sum of the two replicates merged into a single file.

|  | Input (reads) | CLIP (reads) | CLAP (reads) |
| --- | --- | --- | --- |
| Halo-PTBP1-V5 | 33,728,550 | 63,869,780 | 67,601,234 |
| Halo-SAFA-V5 | 32,867,652 | 55,471,650 | 68,236,384 |
| Halo-EZH2-V5 | 31,479,532 | 52,879,616 | 63,512,908 |
| Halo-SUZ12-V5 | 37,653,024 | 33,656,035 | 38,920,563 |
| Halo-EED-V5 | 35,222,788 | 66,686,040 | 64,359,468 |
| Halo-SPEN-V5 | 16,767,104 | 34,293,474 | 51,702,822 |

These results confirm the in vivo binding of SHARP, PTBP1, and SAF-A to the XIST RNA and demonstrate that PRC2 components do not directly bind to the XIST RNA in vivo. These results are consistent with previous biochemical studies that similarly failed to identify an Xist-PRC2 interaction when purified in denaturing conditions[33,36,37].

Example 5: PRC2 Components do not 'Promiscuously' Bind to RNA In Vivo

Figure 5A:
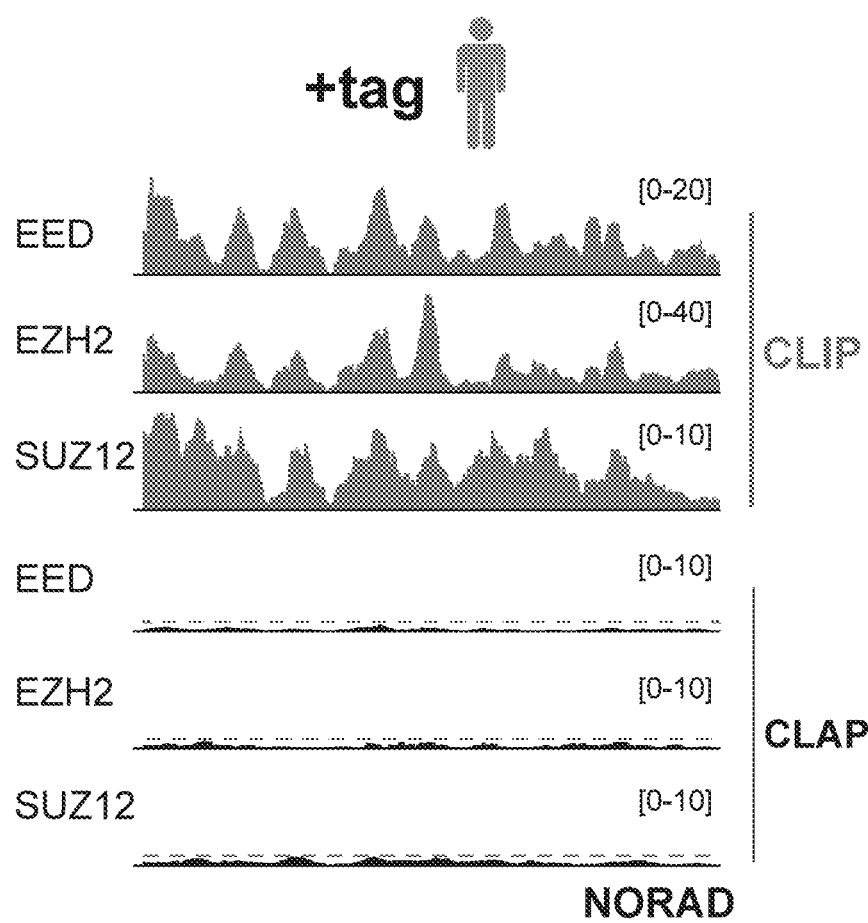
FIGS. 5A-K is a series of graphs showing that PRC2 binding to RNA is abolished using CLAP, in accordance with some embodiments.
Figure 5B:
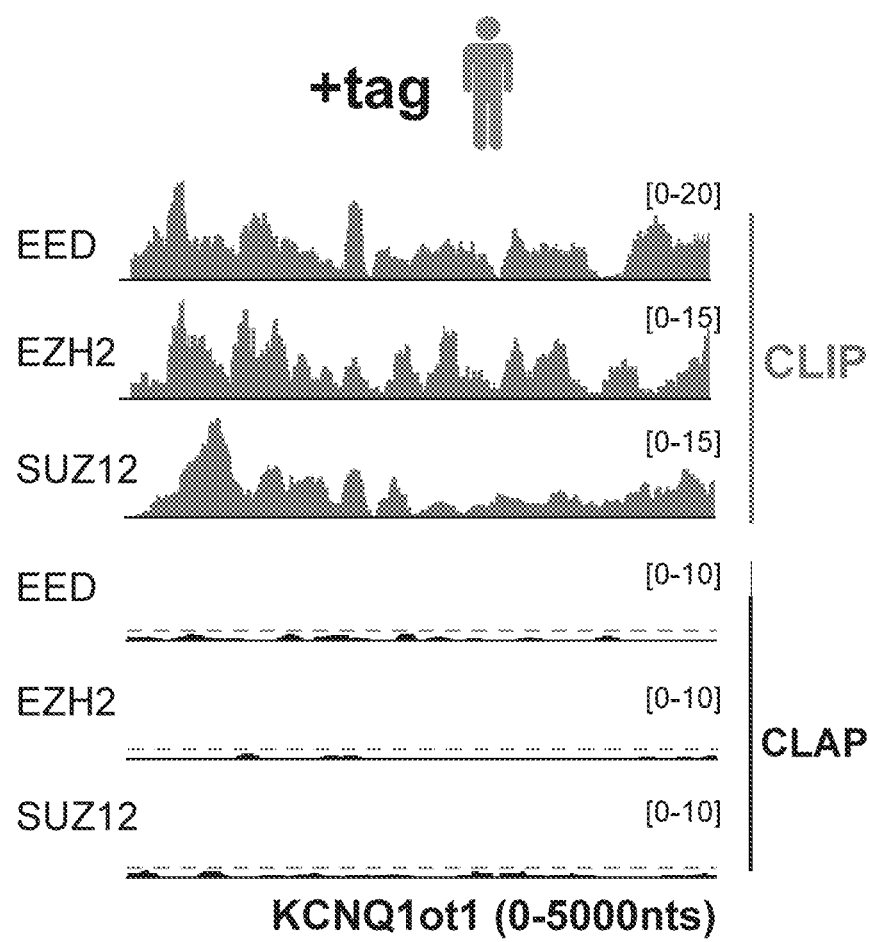
Figure 5C:
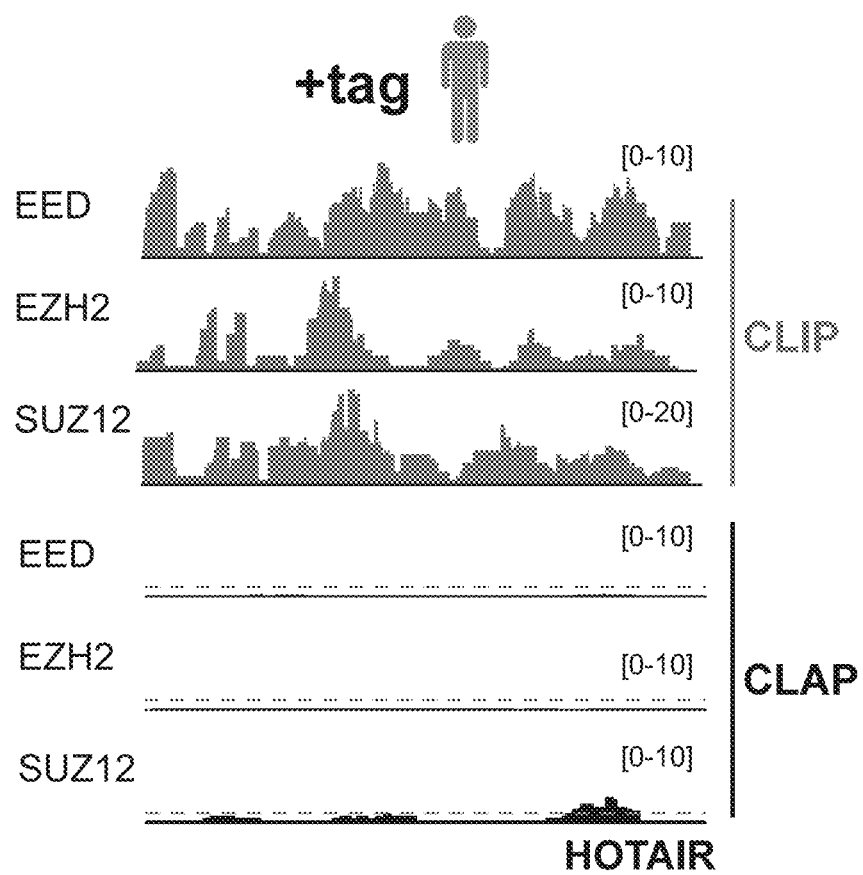
Figure 5D:
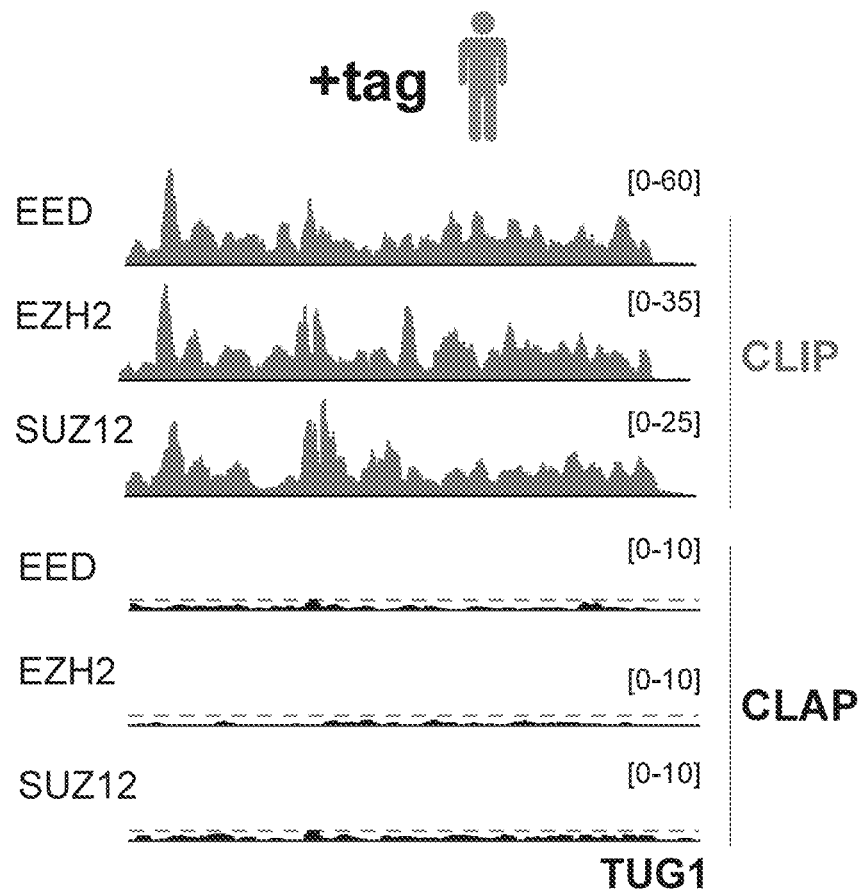
Figure 5E:
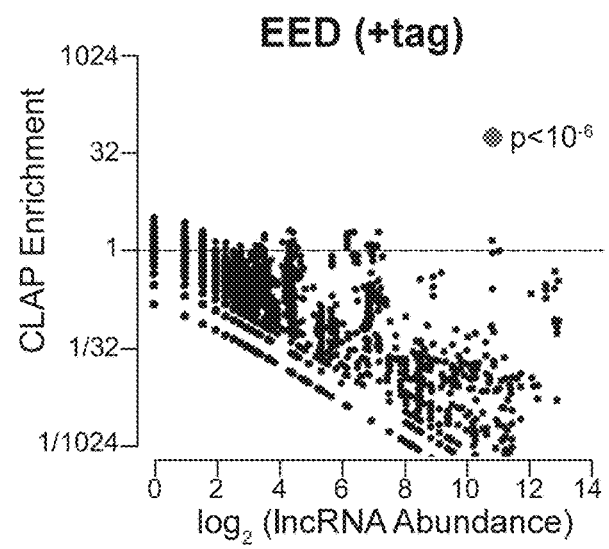
Figure 5F:
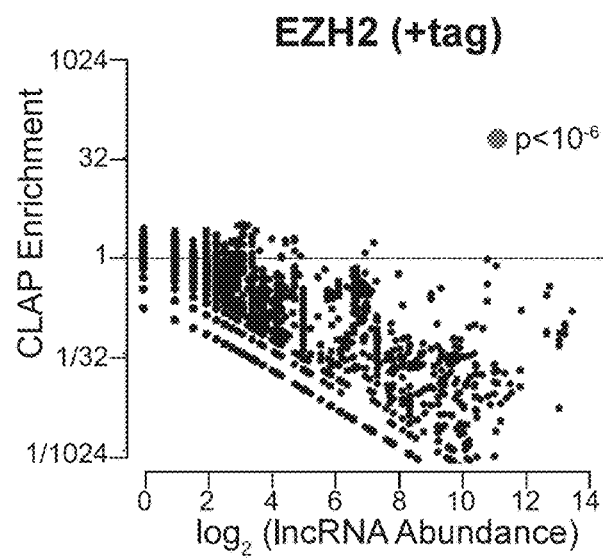
Figure 5G:
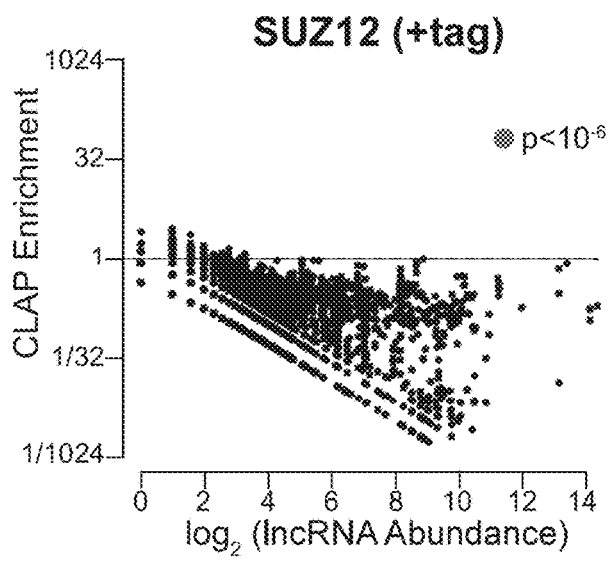

Beyond Xist, PRC2 components have been proposed to bind promiscuously to RNA in vivo based on the observations that most expressed RNAs, including mRNAs and lncRNAs, are enriched in CLIP experiments[13-15] (FIGS. 1B-C, FIGS. 8A-F). To explore whether these represent bona fide interactions that occur in vivo, we analyzed the CLAP data and observed a strong global reduction in binding of all 3 of the PRC2 components to RNA (FIGS. 5A-K) even though the CLIP and CLAP experiments were performed on the same tagged protein from the same lysate (FIG. 2A). For example, focusing on several lncRNAs that have been reported to bind to PRC2 (HOTAIR[3,7,10,69], KCNQ1ot1[9,57,58], and TUG1[3,12]), we observe strong enrichment for all 3 PRC2 components in the CLIP samples, but no enrichment in the CLAP samples (FIGS. 5A-D). Furthermore, when focusing on NORAD, a lncRNA that is predominately localized in the cytoplasm[59,60] and therefore should not bind PRC2, we no longer observe enrichment for any of the 3 PRC2 components by CLAP (FIGS. 5A-D). In fact, not even a single RNA region within a human lncRNA, out of >4,000 annotated and expressed examples[70], was significantly enriched for any of the 3 PRC2 components by CLAP (FIGS. 5E-G).

Figure 5H:
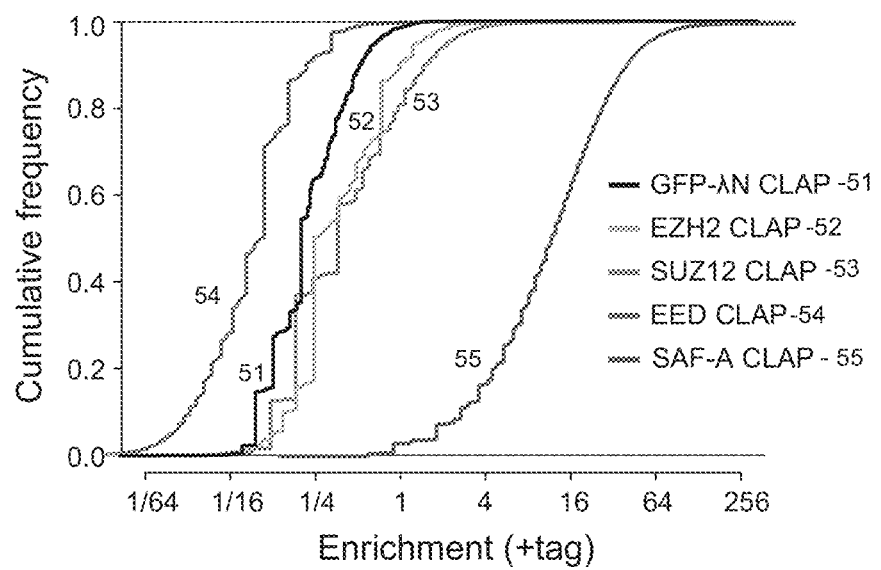
Figure 5I:
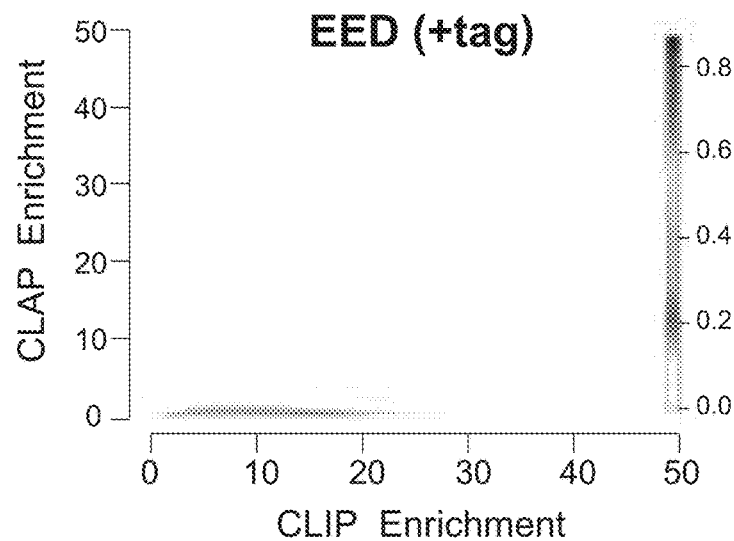
Figure 5J:
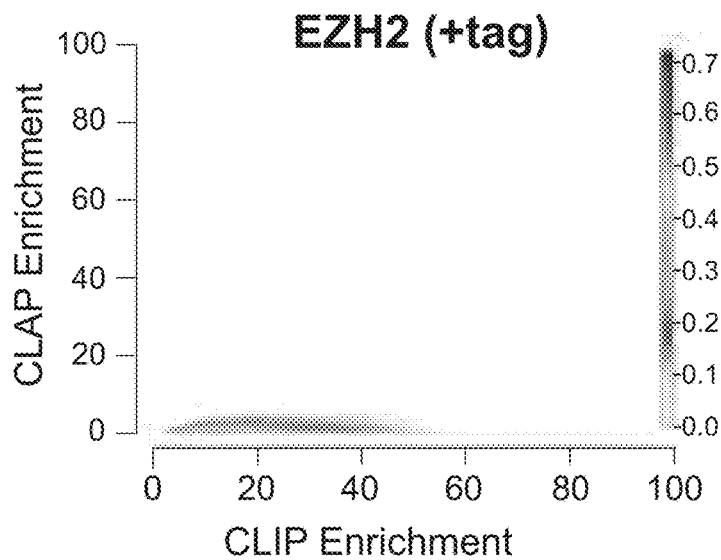
Figure 5K:
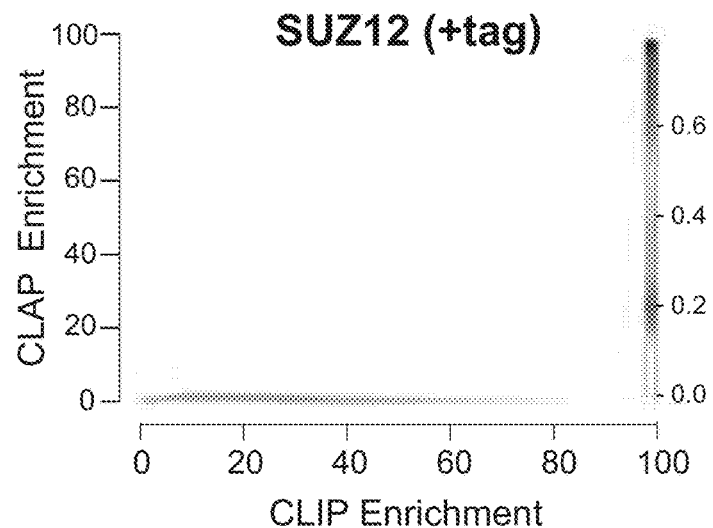

More broadly, we observe that >99.9% of the mRNA and lncRNA regions that were significantly enriched for any of the PRC2 components in the CLIP samples were depleted in the CLAP samples (FIGS. 5H-K). Importantly, these results are strikingly different from the RNA binding profile observed by CLAP for SAF-A (FIG. 5H), which binds to many RNAs with a promiscuous binding profile (FIG. 3C, FIG. 4D, FIGS. 15A-B). Instead, we find that the signal observed for each of the 3 PRC2 components is comparable to the level observed when we perform CLAP on a Halo-tagged GFP fused to a λN bacteriophage RNA binding protein, which does not have any endogenous targets in animal cells (FIG. 5H, FIGS. 16A-B).

Together, these results demonstrate that the PRC2 components do not directly bind to many RNAs in vivo.

CLIP has conventionally been used to accurately map the in vivo RNA binding sites of numerous RBPs and has provided essential insights into their mechanisms of RNA recognition and their functional roles in RNA processing and regulation[45-47,49,61-63]. Consistent with these results, the examples herein demonstrate that CLIP can quantitatively separate in vivo interactions from in vitro associations for the well-characterized RNA binding proteins, yet it can fail to do so in other cases. In fact, we find that background interactions often show discrete "peaks" that could easily be mistaken for legitimate binding sites using standard analytical methods. These results argue for extreme care when interpreting CLIP data when studying proteins that do not contain canonical RNA binding domains (i.e. chromatin proteins) or that interact primarily with lower abundance RNA targets (i.e. lncRNAs), which would be more sensitive to these issues. Beyond PRC2 components, many chromatin proteins have been reported to bind to lncRNAs[4,8,18,71,72] and many additional proteins that lack well-defined RNA binding domains, including metabolic enzymes, have recently been reported to bind to RNA[73-75]. It is contemplated that a careful evaluation of these interactions using denaturing purification methods can accurately separate in vivo interactions from in solution associations.

Our results raise the question about why PRC2 fails to bind to RNA in vivo if it binds promiscuously to RNA with high affinity in vitro. Without being limited by theory, one possible explanation is that PRC2 components are generally localized in a different nuclear compartment from actively transcribed genes and therefore the protein complex likely does not come into contact with most RNAs in vivo. For example, PRC2 proteins are generally enriched in silenced domains of the nucleus at so called "polycomb bodies"—regions that are depleted of actively transcribed genes[76-78]. In the case of RNAs, like Xist, which are present in regions of the nucleus that are enriched for PRC2, the failure of PRC2 to bind may simply reflect the fact that other RNA binding proteins have stronger binding affinity for these RNAs and therefore may outcompete PRC2 binding. For example, in the case of Xist, SHARP binds to the A-repeat of Xist with high affinity such that those sites are likely not accessible for binding by PRC2. Additionally, in vitro binding experiments are generally performed in purified components and fail to take into account the presence of other bona fide RNA binding proteins that interact with these RNAs.

Although our results make clear that PRC2 does not directly bind to RNA broadly in vivo, they do not formally exclude the possibilities that PRC2 may bind to specific RNAs in other contexts or that they may bind to RNA indirectly through protein adapters. In any case, the CLAP method represents a useful tool for addressing these questions and more generally understanding the role of RNA-chromatin interactions because it enables rigorous and specific identification of bona fide interactions between RNA and chromatin proteins. In addition, because CLAP does not require gel extraction, it can be used with protein-protein crosslinkers which can allow for measurements of protein-protein complexes that may interact with RNA, such as those that may occur with chromatin proteins.

Materials and Methods for Examples 1-5

Cell Culture

Human Embryonic Kidney Cells expressing T-antigen (HEK293T cell line) were cultured in HEK Media which consists of the following: 1×DMEM media (Gibco), 1 mM MEM non-essential amino acids (Gibco), 1 mM Sodium Pyruvate (Gibco), 2 mM L-Glutamine (Gibco), 1×FBS (Seradigm). Male mouse ES cells (pSM33 ES cell line) were cultured in serum-free 2i/LIF medium as previously described[79].

V5-Halo Expression Vectors

We constructed a mammalian expression vector as a Gateway compatible destination vector where the expression of the protein of interest (POI) is driven by the synthetic CAG promoter and creates an N-terminal Halo-FLAG (HF) fusion protein with an additional V5 epitope at the C-terminus (pCAG-HF-POI-V5). cDNA clones containing the open reading frames (ORFs) of SAF-A, PTBP1, SHARP, EZH2, EED, and SUZ12 were obtained from DNASU in Gateway entry vectors (pDNOR221). In addition, we purchased a cDNA containing DasherGFP (ATUM Biosciences, FPB-27-609) and also added 3 copies of the λN peptide (DasherGFP-3x-λN). These ORFs were cloned into pCAG-HF-POI-V5 using the Invitrogen Gateway LR Clonase II Enzyme Mix per the manufacturer's protocol.

Transfection of HEK293T Cells

We transfected each expression vector by mixing 25 µL of Fugene HD (Promega) with 475 µl of OPTI-MEM (Gibco). The 500 µL solution was mixed with 500 µL of OPTI-MEM containing 10 µg of pCAG-HF-POI-V5. 1 mL of Fugene/OPTI-MEM/pCAG-HF-POI-V5 complex was transferred to HEK293T plate containing 10 mL of HEK Media. Transfected plates were incubated for ≥16 hours.

Transfection of PSM33 Cells pSM33 cells were trypsinized using 0.025% trypsin (Gibco) and pelleted. Cells were transferred to tubes at a ratio of 2 million cells/transfection and pelleted by centrifugation. Cells were resuspended in resuspension buffer R (Invitrogen) and mixed with 12 µg of DNA. The mixture was transfected with the following settings on the Neon Transfection Device (Invitrogen): 1400 V, 3 pulses, and a 10 second pulse width. Transfected cells were pipetted directly to a 10 cm culture plate. After 24 hours, the media was changed on the samples and 1 µg/mL puromycin was added in order to select for cells that contained the transfected expression cassette.

UV Crosslinking

Cells were washed once with PBS and then crosslinked on ice using 0.25 J cm$^{-2}$ (UV2.5k) of UV at 254 nm in a Spectrolinker UV Crosslinker. Cells were then scraped from culture dishes, washed once with PBS, pelleted by centrifugation at 1,500 g for 4 min, and flash-frozen in liquid nitrogen for storage at −80° C.

Crosslinking and Immunoprecipitation (CLIP)

Cells were lysed in 1 ml lysis buffer (50 mM Tris pH 7.5, 100 mM NaCl, 1% NP-40, 0.5% Sodium Deoxycholate, 1×Promega protease inhibitor cocktail). RNA was digested with Ambion RNase I (1:3000 dilution) to achieve a size range of 100-500 nucleotides in length. Lysate preparations were precleared by mixing with Protein G beads for 30 min at 4° C. Target proteins were immunoprecipitated from 5 million cells with 10 µg of antibody and 75 µl of Protein G beads in 100 µL lysis buffer. The antibodies were pre-coupled to the beads for 1 hr at room temperature with mixing and unbound antibodies removed with 3 washes of lysis buffer. The precleared lysate was added to the Protein G coupled antibody beads overnight at 4 C. After the immunoprecipitation, the beads were washed four times with High salt wash buffer (50 mM TrisHCl pH 7.4, 1 M NaCl, 1 mM EDTA, 1% NP-40, 0.1% SDS, 0.5% sodium deoxycholate) and four times with Wash buffer (20 mM Tris-HCl pH 7.4, 10 mM MgCl2, 0.2% Tween-20).

RNA and protein were eluted by incubating at 50 C in NLS elution buffer (20 mM Tris-HCl pH 7.5, 10 mM EDTA, 2% N-lauroylsarcosine, 2.5 mM TCEP) supplemented with 100 mM DTT for 20 minutes. Samples were then run through an SDS-PAGE gel and transferred to a nitrocellulose membrane using the iBLOT transfer system, and a region 70 kDa above the molecular size of the protein of interest was isolated and treated with Proteinase K (NEB) followed by buffer exchange and concentration with RNA Clean & Concentrator™-5 (Zymo). RNA sequencing libraries from these samples were constructed as previously described[67, 68,80,81]. We used the following antibodies: V5 antibody (Bethyl, A190-120A), EZH2 (Active Motif, 39933), EED (Santa Cruz, SC-293203), SUZ12 (Active Motif, 39357), SHARP (Bethyl, A301-119A), PTBP1 (Abcam, ab5642), SAF-A/hnRNPU (Santa Cruz, SC-32315).

CLIP Library Construction

CLIP samples were treated as previously described[68,80]. Briefly, after immunoprecipitation and wash steps, the RNA was dephosphorylated (Fast AP) and cyclic phosphates removed (T4 PNK) and then ligated on Protein G beads with an RNA adapter containing a RT primer binding site.

The ligated protein-bound RNA was then run through a denaturing PAGE gel and transferred to nitrocellulose membrane (as described above). The RNA was then extracted by proteinase K and purified using a spin column (Zymo). The RNA was reverse transcribed into single stranded cDNA. After RT, the RNA was degraded and a second adapter was ligated to the single stranded DNA. PCR amplification is achieved using primers that target the 3' and 5' adapters.

Input total RNA libraries were constructed using the same steps as outlined above except that the dephosphorylation, cyclic phosphate removal, and ligation were performed in solution rather than on Protein-G beads.

Covalent Linkage and Affinity Purification (CLAP)

Total Cell Lysate Preparation.

We lysed batches of 5 million cells by completely resuspending frozen cell pellets in 1 mL of ice cold iCLIP lysis buffer (50 mM Hepes, pH 7.4, 100 mM NaCl, 1% NP-40, 0.1% SDS, 0.5% Sodium Deoxycholate) supplemented with 1× Protease Inhibitor Cocktail (Promega), 200 U of Murine RNase Inhibitor (New England Biolabs), 20 U Turbo DNase (Ambion), and 1× Manganese/Calcium Mix (0.5 mM $CaCl_2$, 2.5 mM $MnCl_2$). Samples were incubated on ice for 10 minutes to allow lysis to proceed. The lysates were then incubated at 37° C. for 10 minutes at 1150 rpm shaking on a Thermomixer (Eppendorf). Lysates were cleared by centrifugation at 15,000 g for 2 minutes. The supernatant was collected and kept on ice until bound to the HaloLink Resin.

Preparation of HaloLink Resin.

We used 200 μL of 25% HaloLink Resin (50 μL of HaloLink Resin total) per 5 million cells.

Resin was washed three times with 2 mL of 1×TBS (50 mM Tris pH 7.5, 150 mM NaCl) and incubated in 1× Blocking Buffer (50 mM HEPES, pH 7.5, 10 μg/mL Random 9-mer, 100 μg/mL BSA) for 20 minutes at room temperature with continuous rotation. After the incubation, resin was washed three times with 1×TBS.

Purification and Washes of Halo-Tagged Protein.

The cleared lysate was mixed with 50 μl of HaloLink Resin and incubated at 4° C. for 3-16 hrs with continuous rotation. The captured protein bound to resin was washed three times with iCLIP lysis buffer at room temperature and then washed three times at 90° C. for 2 minutes while shaking at 1200 rpm with each of the following buffers: 1× ProK/NLS buffer (50 mM HEPES, pH 7.5, 2% NLS, 10 mM EDTA, 0.1% NP-40, 10 mM DTT), High Salt Buffer (50 mM HEPES, pH 7.5, 10 mM EDTA, 0.1% NP-40, 1M NaCl), 8M Urea Buffer (50 mM HEPES, pH 7.5, 10 mM EDTA, 0.1% NP-40, 8 M Urea), and Tween buffer (50 mM HEPES, pH 7.5, 0.1% Tween 20, 10 mM EDTA). Finally, we adjusted the buffer by washing with Elution Buffer (50 mM HEPES, pH 7.5, 0.5 mM EDTA, 0.1% NP-40) three times at 30° C.

Elution of Purified Protein and RNA Purification.

The resin was resuspended in 83 μL of Elution Buffer and split into a 75 μL (ProK elution) and 8 μL (TEV elution) reaction. 25 μL of 4× ProK/NLS Buffer and 10 μL of ProK were added to the ProK elution tube and the sample was incubated at 50° C. for 30 minutes while shaking at 1200 rpm. 2.3 μL of ProTEV Plus Protease (Promega) was added to the TEV Elution and the sample was incubated at 30° C. for 30 minutes while shaking at 1200 rpm.

Visualization of Purified Protein

For each experiment, we ensured that we successfully purified the Halo-tagged protein. To do this, the TEV elution sample was mixed with 1×LDS Sample Buffer (Invitrogen) and 1× Reducing Agent (Invitrogen) and heated for 6 minutes at 70° C. The sample was run on a 3-8% Tris Acetate Gel (Invitrogen) for 1 hour at 150 V. The gel was transferred to a nitrocellulose membrane using an iBlot Transfer Device (Invitrogen). The nitrocellulose membrane was blocked with Odyssey Blocking Buffer (LI-COR) for 30 minutes. We incubated the membrane in Anti-FLAG mouse monoclonal Antibody (Sigma, F3166) and V5 rabbit polyclonal antibody (Santa Cruz, sc-83849-R) at a 1:2500 dilution for 2 hours at room temperature to detect the protein.

We visualized the protein by incubating the membrane in 1:17,500 dilution of both IRDye 800CW Goat anti-Rabbit IgG (LI-COR, 925-32210) and IRDYE 680DR Goat anti-Mouse IgG (LI-COR, 925-68070) for 1 hour at room temperature followed by imaging on a LICOR Odyssey.

Preparation of RNA for NextGen Sequencing Libraries.

RNA was purified from the ProK elution sample and an RNA-Seq library was constructed as previously described[80, 81]. Briefly, after proK elution, the RNA was dephosphorylated (Fast AP) and cyclic phosphates removed (T4 PNK) and then cleaned up on Silane beads as previously described. The RNA was then ligated to an RNA adapter containing a RT primer binding site. The ligated RNA was reverse transcribed (RT) into cDNA, the RNA was degraded using NaOH, and a second adapter was ligated to the single stranded cDNA. The DNA was amplified and Illumina sequencing adaptors were added by PCR using primers that are complementary to the 3' and 5' adapters[81].

Sample pooling and Sequencing

The molarity of PCR amplified libraries were measured by Agilent Tapestation High Sensitivity DNA screentapes and all samples were pooled at equal molarity. The pool was then purified and size selected on a 2% agarose gel and cut between 150-700 nts. The final libraries were measured by Agilent Bioanalyzer and Qubit high sensitivity DNA to determine the loading density of the final pooled sample. Pooled samples were paired-end sequenced on an Illumina HiSeq 2500 with read length ≥35×35 nts.

Read Processing and Alignment

Sequencing reads were trimmed to remove adaptor sequences and any bases containing a quality scores <10 using Trimmomatic[82]. We filtered out all read-pairs where either read was trimmed to <25 nucleotides. We excluded PCR duplicates using the FastUniq tool[83]. The remaining reads were then aligned to Ribosomal RNAs (rRNAs) using the Tagdust program[84] with a database of 18S, 28S, 45S, 5S, 5.8S sequences. TagDust was chosen because it allowed more permissive alignments to rRNA reads that contained mismatches and indels due to RT errors induced by rRNA post-transcriptional modifications. The remaining reads were then aligned to a combined genome reference containing the mouse (mm9) and human (hg19) genomes using STAR aligner[85]. Only reads that mapped uniquely in the genome and unambiguously to the human or mouse genomes were kept for further analysis.

Gene Window Enrichment Calculations

All human (hg19) and mouse (mm9) annotated genes (RefSeq, downloaded from UCSC Hg19 and MM9, respectively) were used as a reference set except for the genes encoding the 6 transfected proteins. In addition, we added all human lncRNAs as annotated by Genecode (release 26). For each gene, we enumerated 100 nucleotide windows that span across the exons and introns of each gene. For each window, we calculated the enrichment by computing the number of reads overlapping the window in the protein elution sample divided by the number of reads in the input sample. Because all windows overlapping a gene should have the same expression level in the input sample, we estimated the number of reads in the input as the maximum of either (i) the number of reads over the window or (ii) the median read count over all windows within the gene. This approach provides a conservative estimation of enrichment because it prevents windows from being scored as enriched if the input values over a given window are artificially low, while at the same time accounting for any non-random issues that lead to increases in read counts over a given window (i.e. alignment artifacts leading to non-random assignment or pileups).

We normalized this observed ratio by the expected number of reads in a window defined as the total number of reads in the protein elution sample divided by the number of windows covered in the sample. This normalization estimates the expected read coverage for each window and accounts for the redistribution of reads that occur because of the fixed sequencing depth used and possible "drop out" of specific RNA regions during the enrichment process. The total number of reads in the protein elution or input samples was calculated by adding the total number of human-specific reads, mouse-specific reads, and ribosomal RNA reads. Nominal p-values were calculated for each window using a binomial test where k (number of successes) is defined as the number of reads in the protein elution samples within the window, N (number of trials) is the sum of the number of reads in the protein elution and input samples, and p (probability of success) is the expected number of reads per window in the elution divided by the sum of the expected number of reads per window in elution and input samples. (The expected number of reads is defined as the total number of reads divided by the number of windows). For plotting and reporting purposes, we considered all regions with a nominal binomial p-value<$10^{-6}$ as significant. However, the overall results reported are robust to the precise p-value cutoff used.

Motif Analysis

Peaks were called on PTBP1 CLIP and CLAP samples using the MACS2 program with options (--broad-peak, and -q 0.01) and input RNA levels as a control sample. The sequence corresponding to each peak was extracted using bedtools (getfasta) and subsequently analyzed using the MEME motif calling software (parameters: -dna -mod zoops -nmotifs 5 -minsites 50 - minw 5 -maxw 9). In both the CLIP and CLAP samples, the CU rich motifs matching the expected PTBP1 motif was identified and had the greatest number of sites of any of the identified motif matches.

Plotting and Visualization

IGV plots for specific RNAs were generated by computing enrichments (as described above) across 100 nucleotide windows and the enrichment value was plotted at the midpoint of each window.

Epitope Tags Controls

Figure 6:
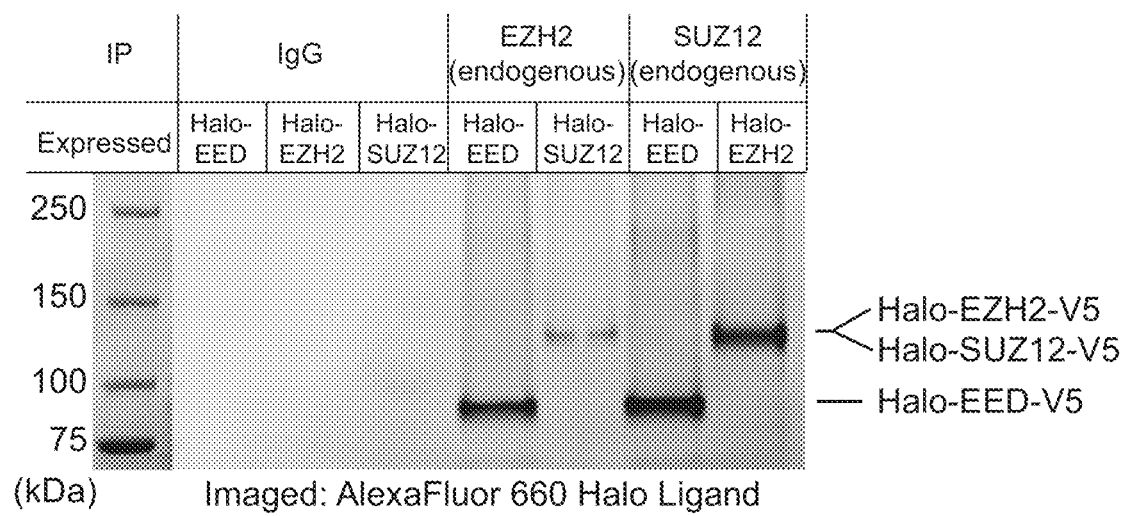
FIG. 6 is an image of a gel, showing that PRC2 components tagged with V5-Halo interact with endogenous PRC2 components. Endogenous PRC2 components (EZH2 or SUZ12) were immunoprecipitated from cell lysates expressing Halo-EED-V5, Halo-EZH2-V5, or Halo-SUZ12-V5 protein. The amount of tagged protein that was associated with the endogenous protein was visualized using a fluorescently labeled Halo-ligand (AlexFluor 660) on a gel.
Figure 7A:
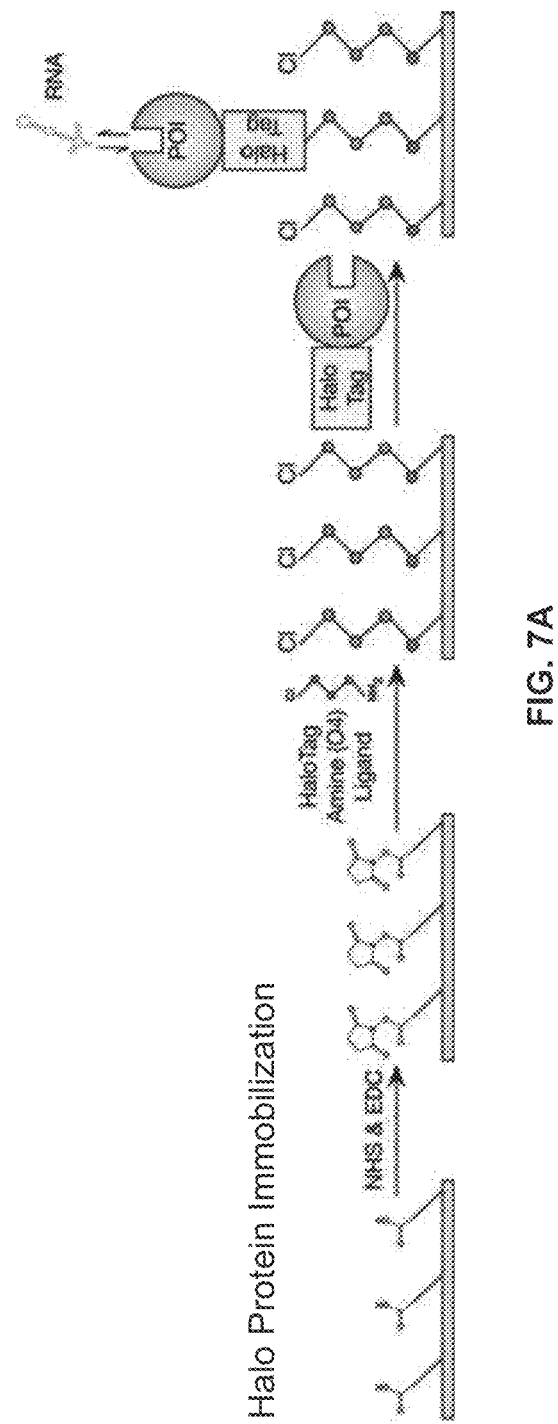
FIGS. 7A-G are a series of schematic diagrams and graphs showing that V5 and Halo-tagged PRC2 components retain their RNA binding activity in vitro.
Figure 7B:
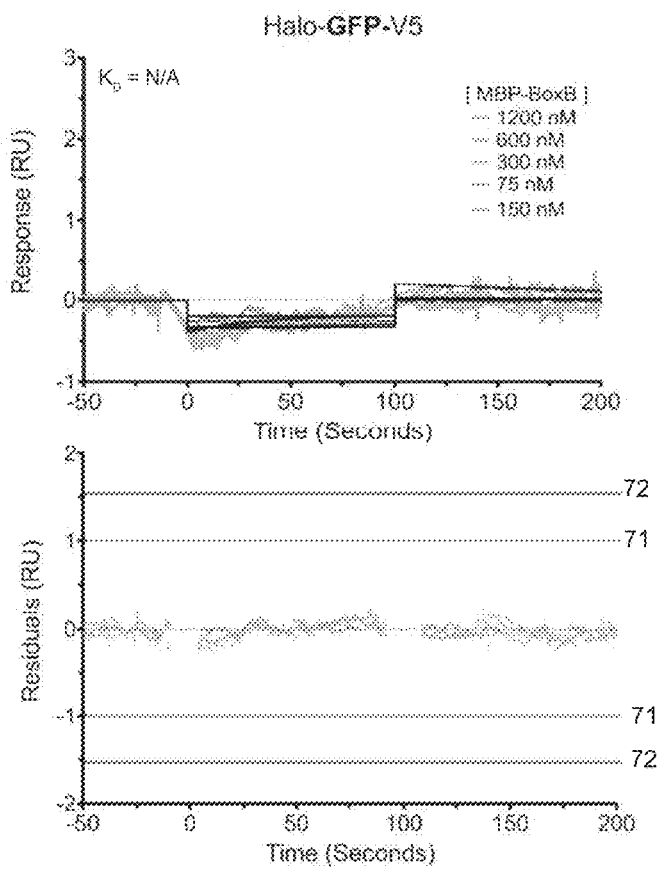
Figure 7C:
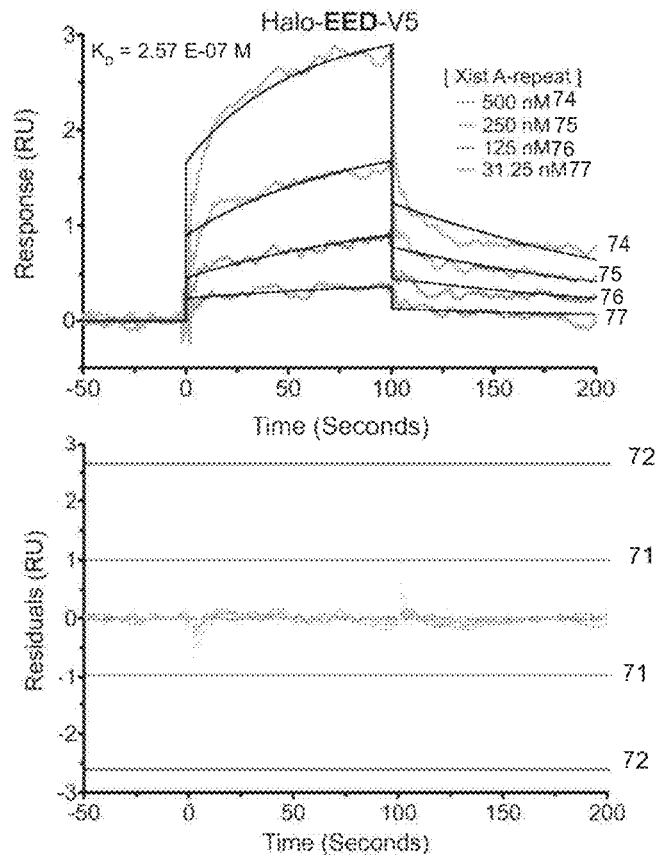
Figure 7D:
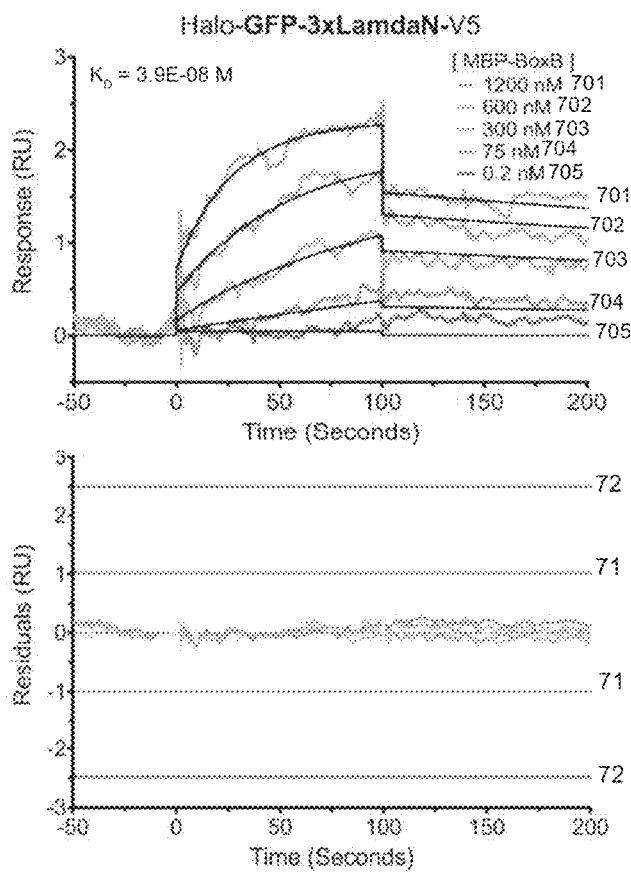
Figure 7E:
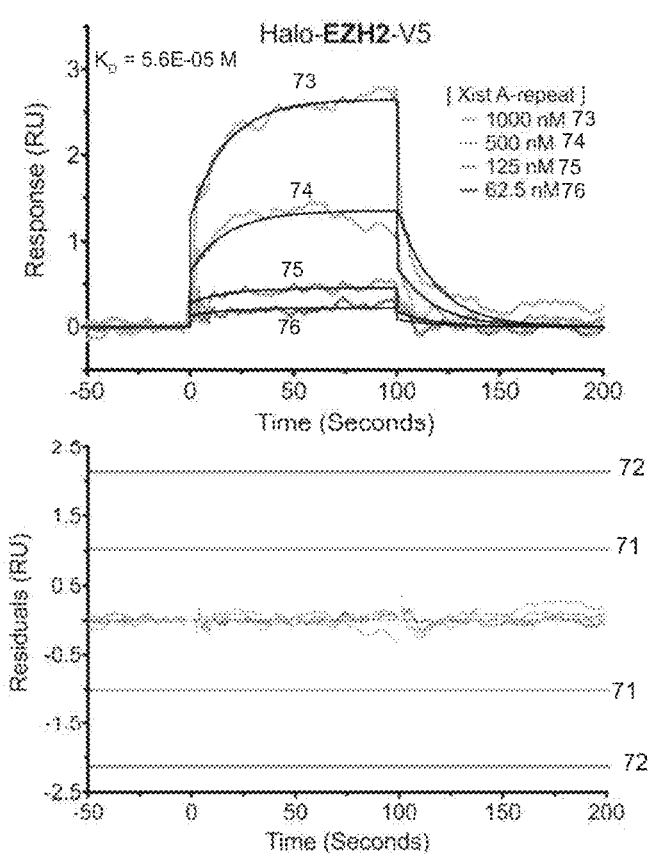
Figure 7F:
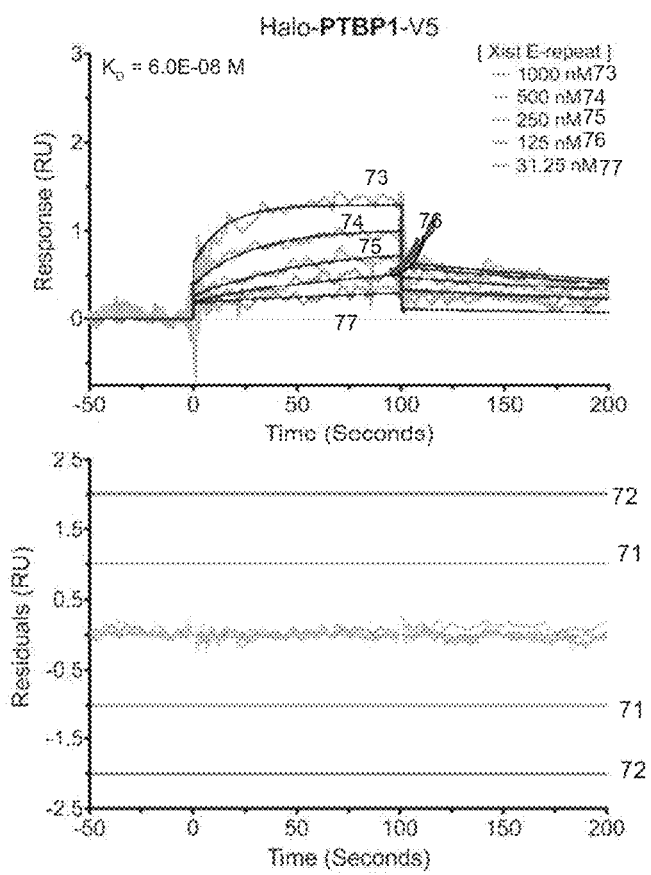
Figure 7G:
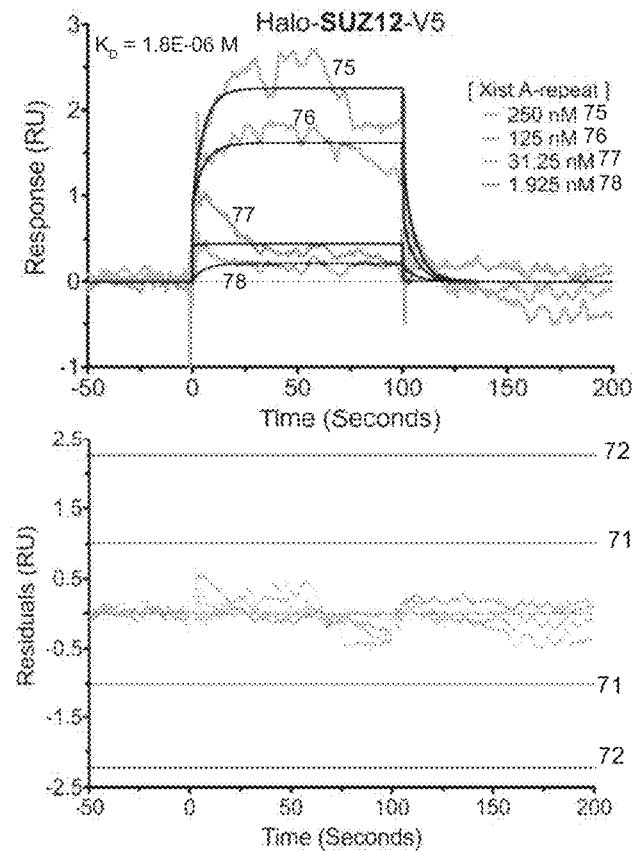
Figure 8A:
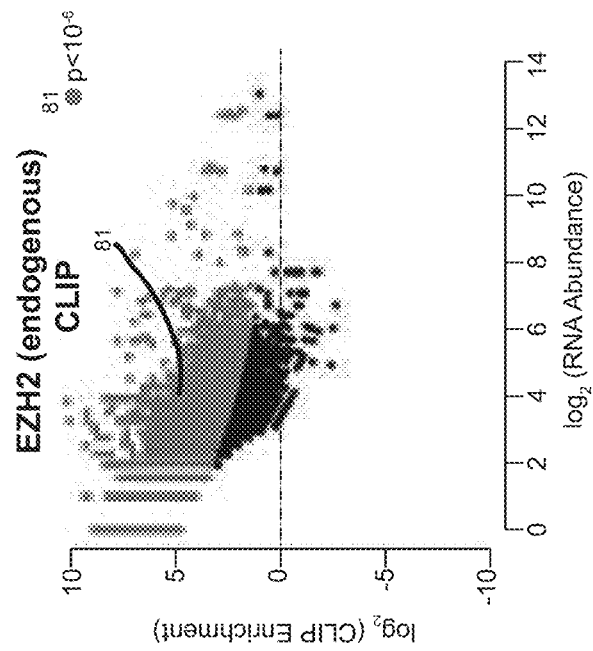
FIGS. 8A-F are a series of graphs showing CLIP on V5 tagged PRC2 components is comparable to CLIP performed on the endogenous proteins. Scatter plot of RNA abundance (log scale, x-axis) compared to the CLIP enrichment (log scale, y-axis) for the V5-tagged PRC2 components (FIGS. 8A, 8C, 8E) and CLIP performed using antibodies that recognize the endogenous proteins (FIGS. 8B, 8D, 8F) across 100-nucleotide windows of all annotated human RNAs. Windows with significant enrichment (binomial $p<10^{-6}$) 81 are shown.
Figure 8B:
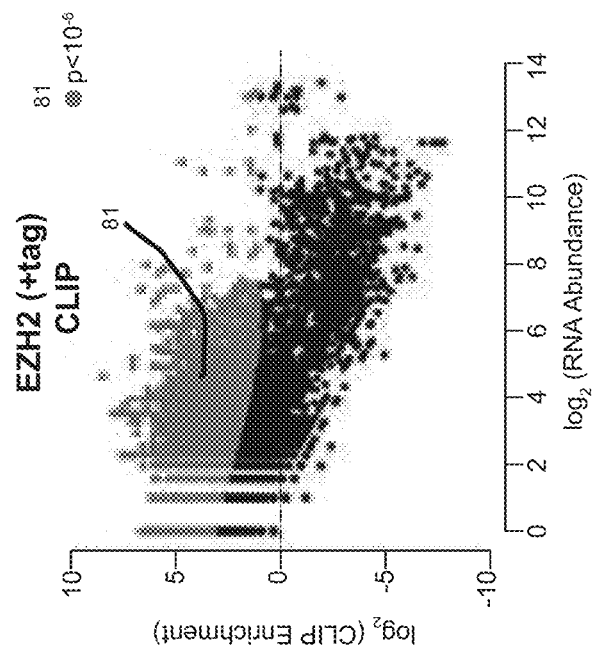
Figure 8D:
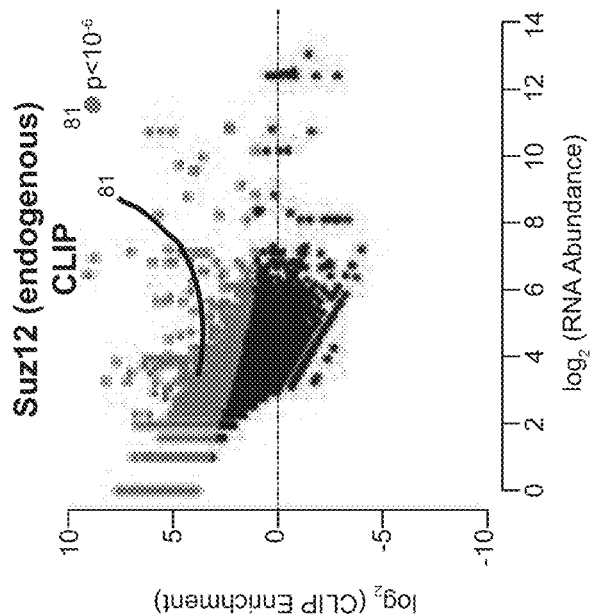
Figure 8C:
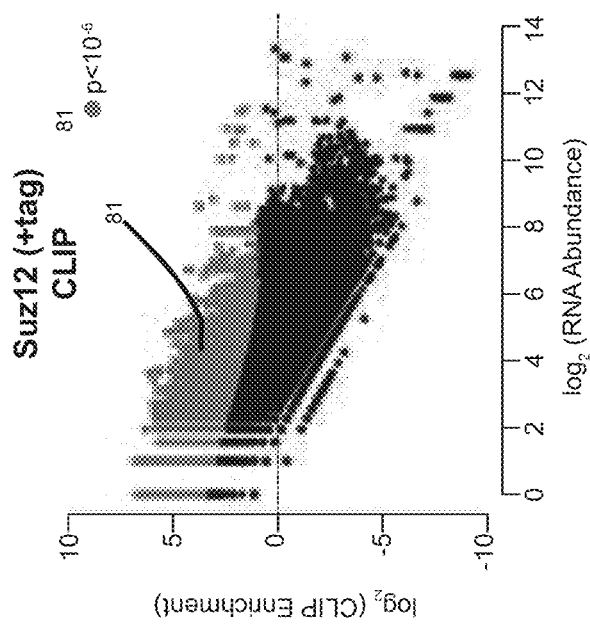
Figures 8E, 8F:
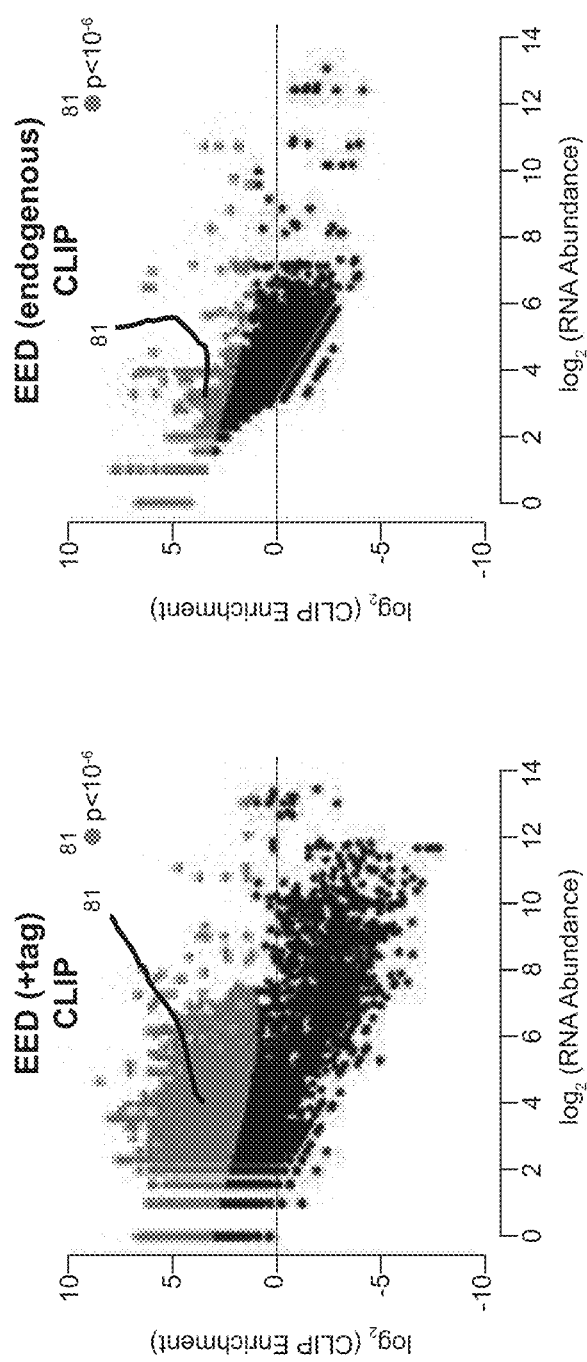
Figure 9:
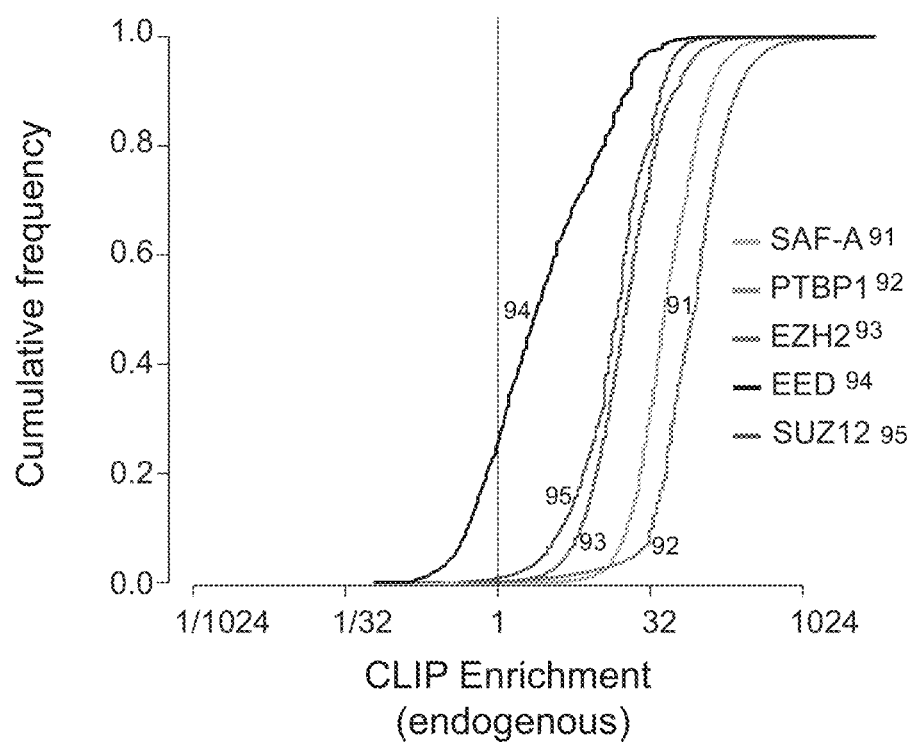
FIG. 9 is a graph of RNA regions identified by CLIP in V5-tagged proteins are also enriched when CLIP is performed on the endogenous proteins. Cumulative distribution showing the CLIP enrichment levels measured in the endogenous CLIP samples across all RNA regions that were identified as significantly enriched by CLIP in the corresponding V5-tagged proteins.
Figure 10A:
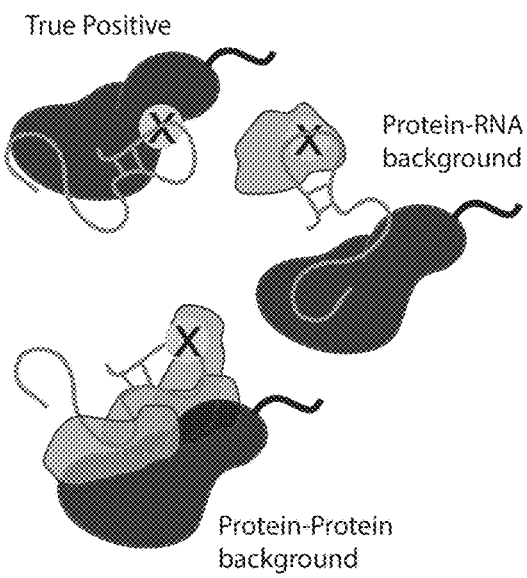
FIGS. 10A-F are a series of images and graphs showing that CLAP accurately separates crosslinked RNA-protein interactions from those that occur in solution in accordance with some embodiments.
Figure 10B:
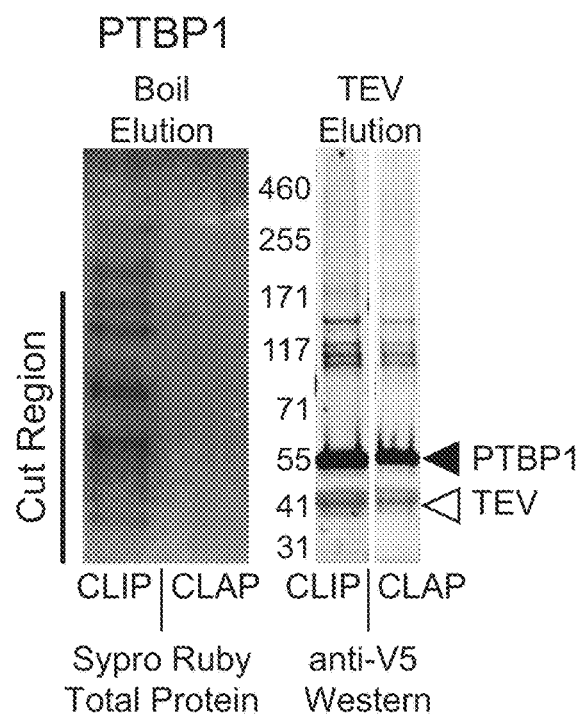
Figure 10C:
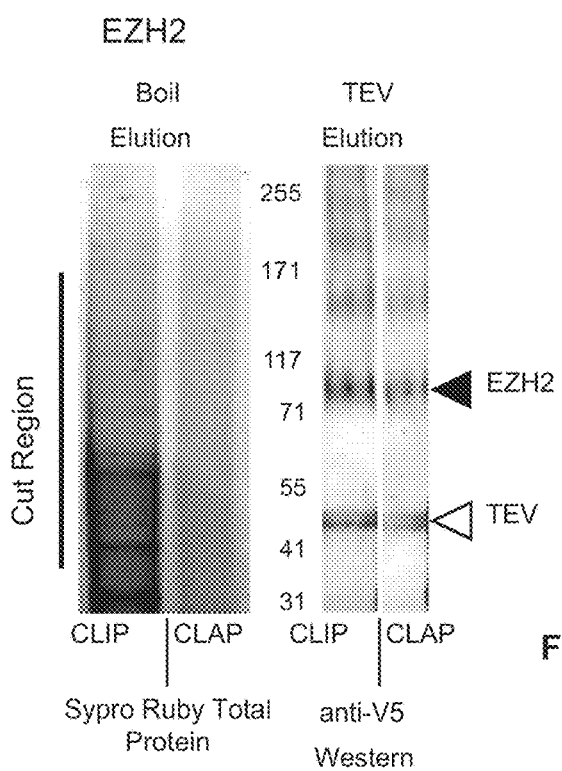
Figure 10D:
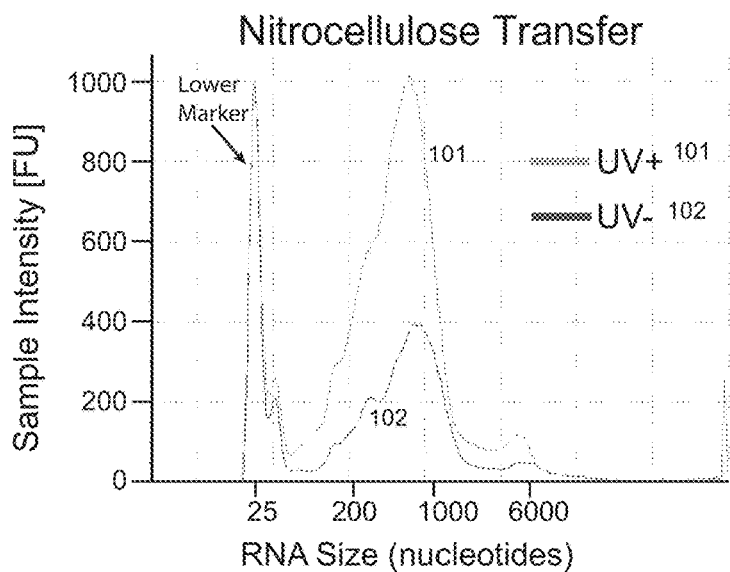
Figure 10E:
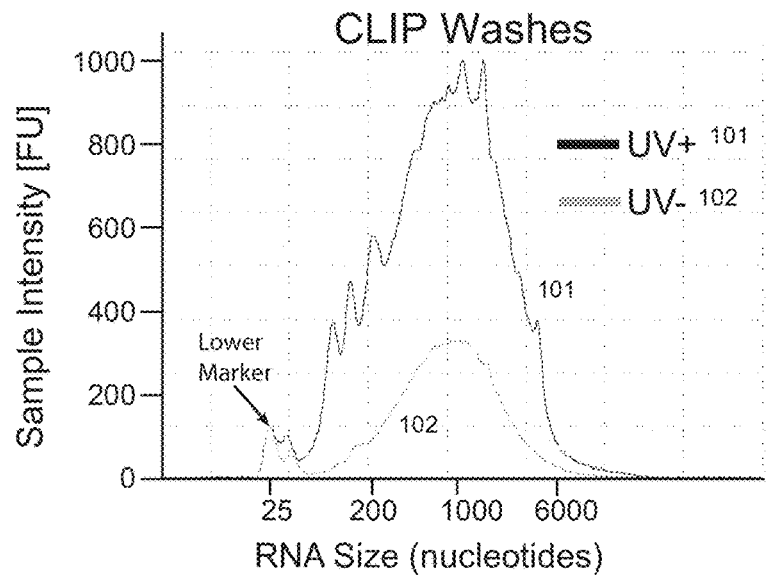
Figure 10F:
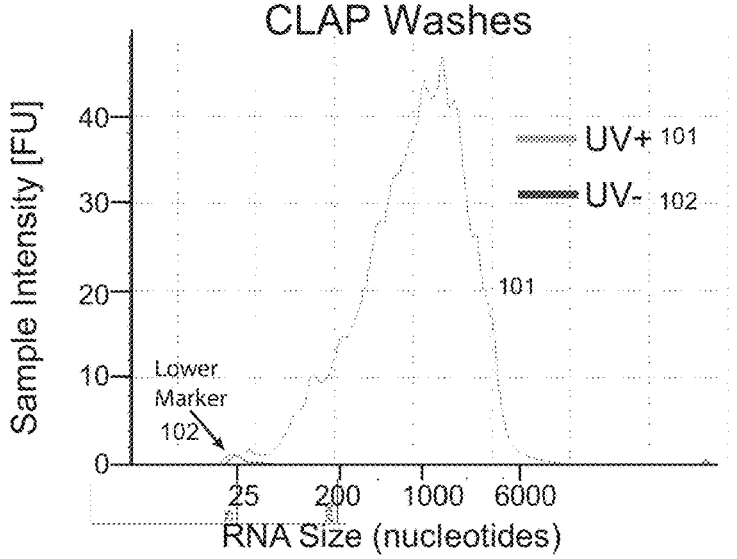
Figure 11C:
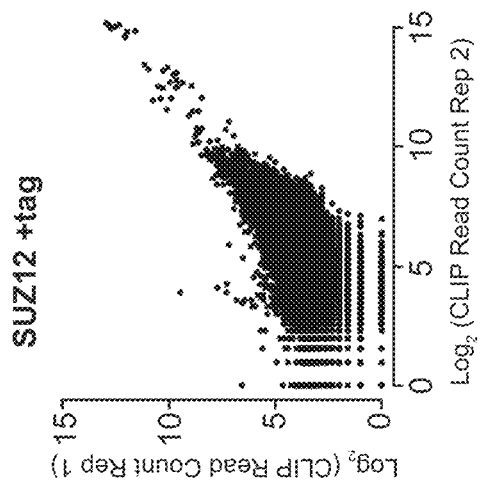
FIGS. 11A-L is a series of graphs showing that replicate CLIP and CLAP experiments show virtually identical results. Scatter plot comparing two independent CLIP (FIGS. 11A-F) and CLAP (FIGS. 11G-L) experiments for each of the 6 proteins studied. The read counts across all 100-nucleotide windows of all human RNAs (+tag) are shown.
Figure 11B:
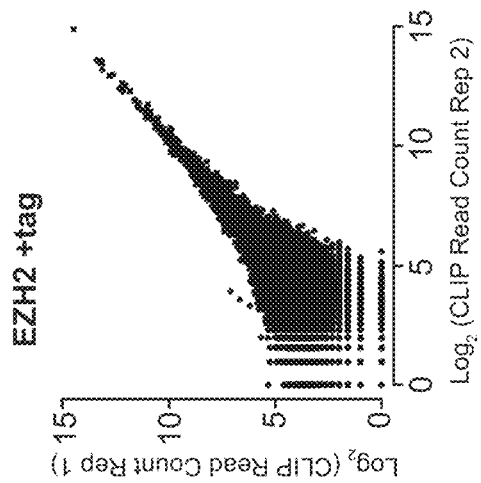
Figure 11A:
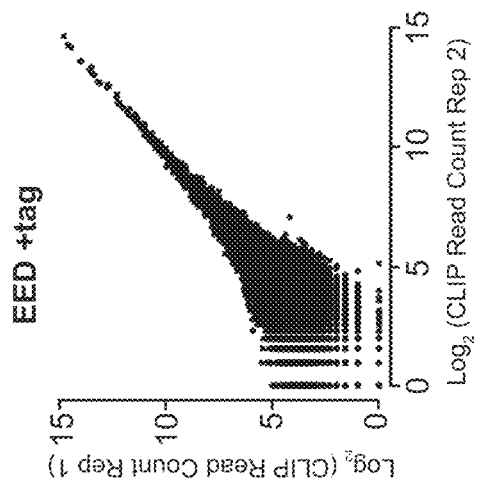
Figure 11D:
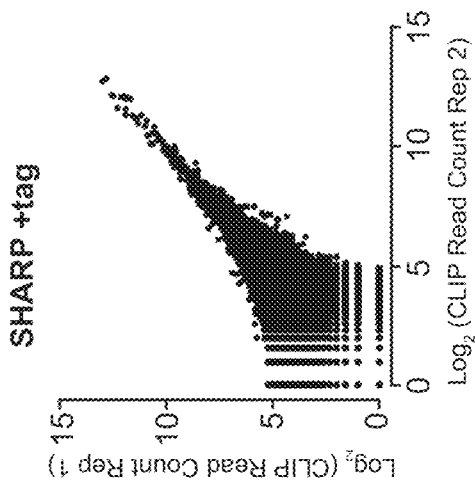
Figure 11E:
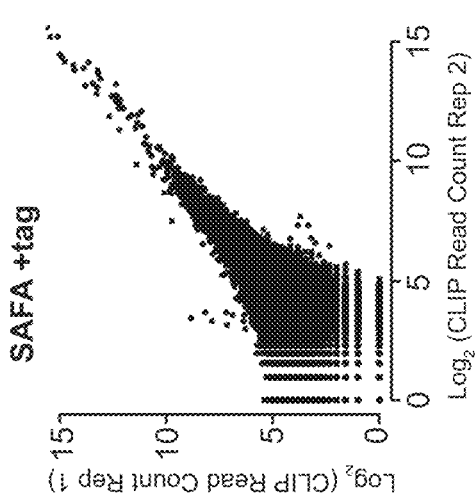
Figure 11F:
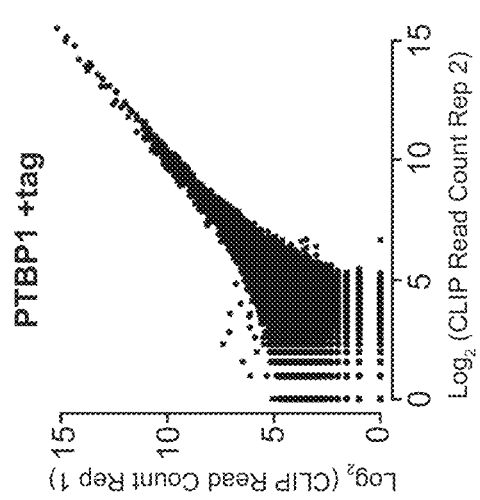
Figure 11I:
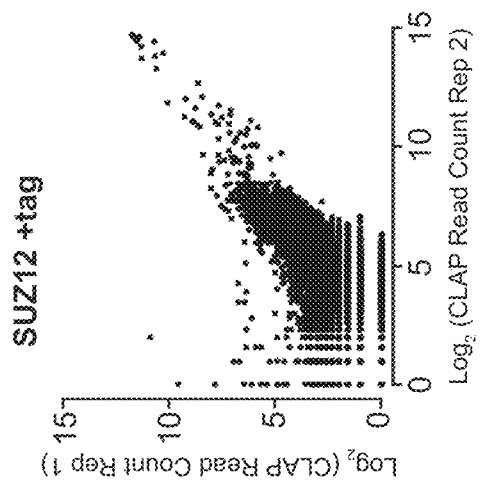
Figure 11H:
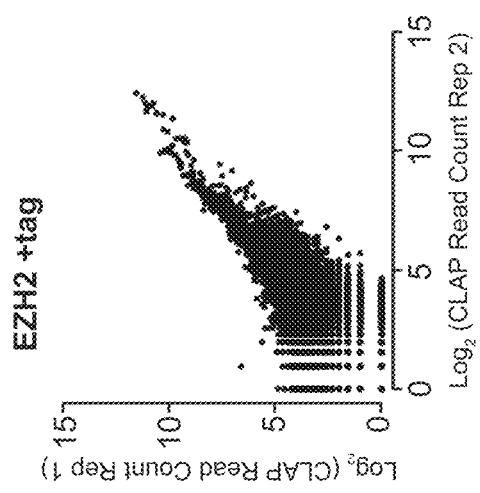
Figure 11G:
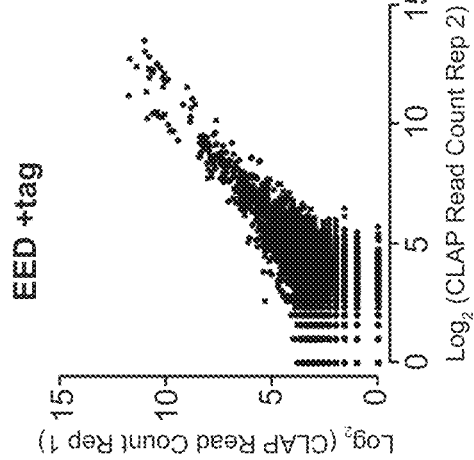
Figure 11L:
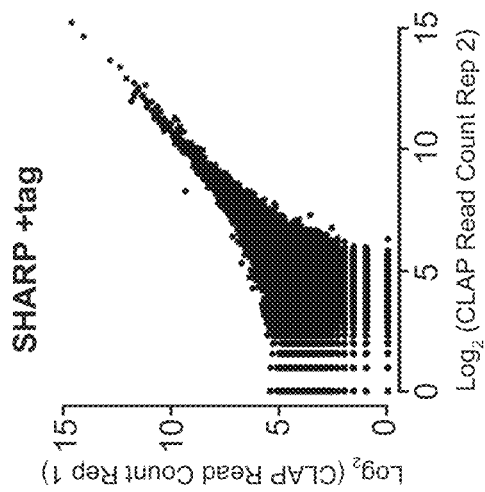
Figure 11K:
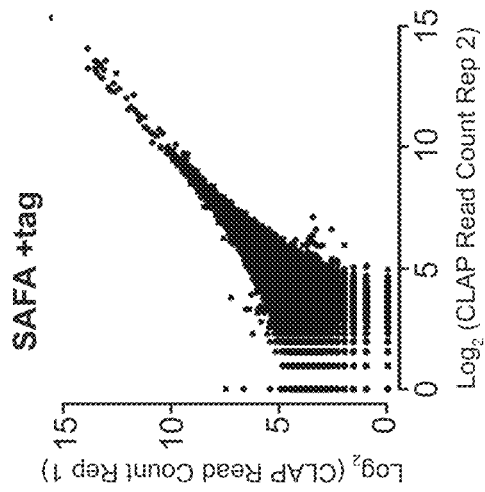
Figure 11J:
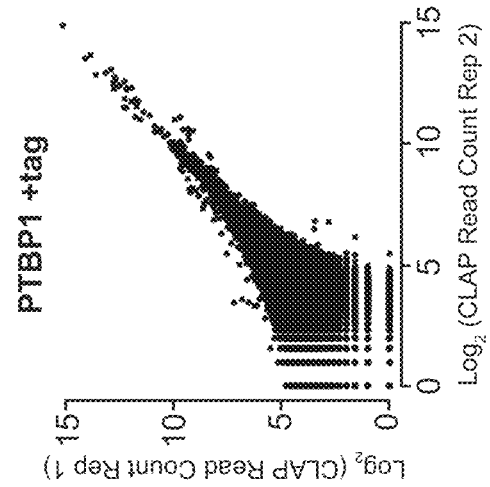
Figure 12B:
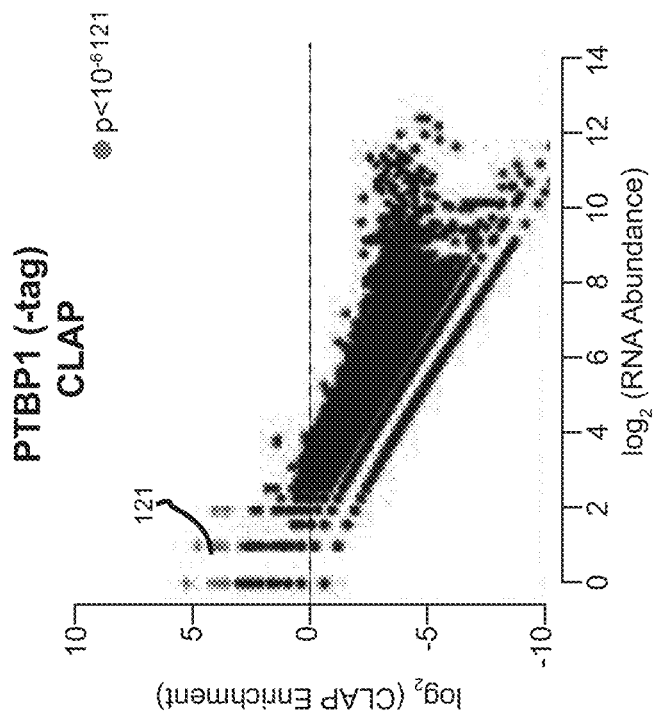
FIGS. 12A-D is a series of graphs showing that CLAP removes the few RNAs detected by CLIP of PTBP1 and SAF-A in the -tag samples. Scatter plot of RNA abundance compared to the CLIP enrichment (FIGS. 12A and 12C) or CLAP enrichment (FIGS. 12B and 12D) for PTBP1 (FIGS. 12A and 12B) or SAF-A (FIGS. 12C and 12D) in the -tag samples across 100-nucleotide windows of all annotated human RNAs. Windows with significant enrichment (binomial $p<10^{-6}$) are shown 121.
Figure 12A:
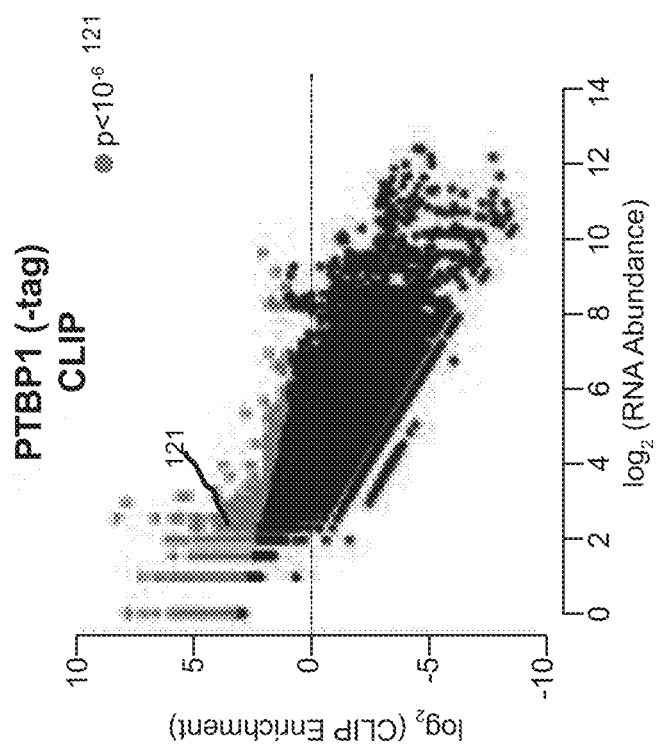
Figure 12D:
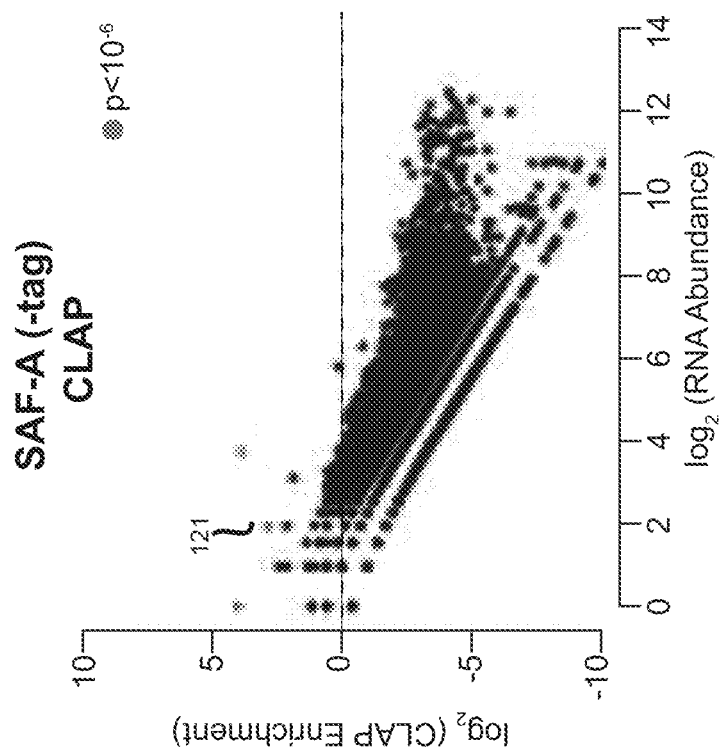
Figure 12C:
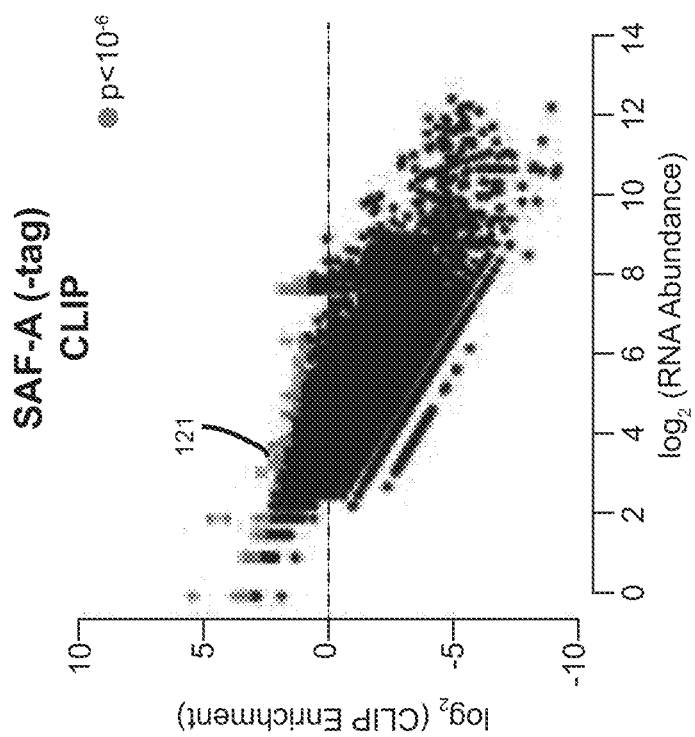

To ensure that the V5 and Halo epitope tags do not impact protein function or RNA binding, we performed several controls. (i) We compared the V5 CLIP data generated from these same tagged proteins to CLIP data generated using antibodies against each of the endogenous proteins and observed the same general binding profiles for all 6 proteins (FIGS. 9 and 13A-B). (ii) We found that these tagged proteins are properly incorporated into the PRC2 complex because immunoprecipitation of the endogenous PRC2 components co-purify with the tagged components (FIG. 6). (iii) We measured the RNA binding affinity of these tagged proteins in vitro and confirmed that they still retain RNA binding activity (FIGS. 7A-G, Table 1).

Co-Immunoprecipitation of PRC2 Components and AlexaFluor Labeling

5 μgs of Rabbit IgG (Cell Signaling, 2729S), anti-EZH2 (Active Motif, 39933), or anti-SUZ12 (Active Motif, 39357) antibodies were coupled to 50 μL of Protein G beads at room temperature for 30 minutes. Beads were washed 3 times with 300 μL mammalian lysis buffer (50 mM HEPES pH 7.5, 150 mM NaCl, 1% Triton X-100, 0.1% Na-Doc). HEK293T cells expressing Halo/V5 fusion proteins of EZH2, EED, or SUZ12 were lysed as in the CLAP procedure except that 1 mL of mammalian lysis buffer was used in place of iCLIP lysis buffer. Beads were then incubated with HEK293T lysates expressing either Halo-EZH2-V5, Halo-EED-V5, or Halo-SUZ12-V5. The antibody coupled beads were incubated with lysate overnight. After binding, the beads were washed 3 times with mammalian lysis buffer for 2 minutes with shaking (1500 rpm) on a thermomixer. After washes, 100 μL of lysis buffer was added to beads and transferred to PCR strip tubes. Once transferred, the beads were placed on a magnet and the supernatant was removed. The buffer was replaced with 18 μL of mammalian lysis buffer+2 uL of a 1:60 dilution of AlexaFluor660-Halo ligand (Promega, G8471). This was incubated at room temperature in the dark for 20 minutes. The reaction was quenched by adding 4×LDS loading buffer and heating at 70° C. for 7 minutes. After heating, the beads were placed on a magnet and the supernatant was loaded on a 3-8% Tris-Acetate gel. The gel was imaged directly on the LICOR Odyssey.

Measurement of In Vitro Binding of PRC2 Components to RNA

Direct binding of RNA to covalently immobilized HaloT-agged fusion proteins was assayed on a Biacore T200 (GE Healthcare Life Sciences) and Series S Sensor Chip CM5 (GE Healthcare Life Sciences, BR100530). We coupled the Halo capture reagent (chloroalkane) to the chip by amine coupling according to the manufacturer's protocol (Promega, P6741) with the following deviations. The Halo capture reagent was resuspended in anhydrous DMSO (5 mg/ml) and diluted to 2.5 mg/ml in 1×HBS-N Buffer (GE Healthcare) and injected onto the chip until 300 resonance units (RU) of amine ligand was immobilized. Ethanolamine (1 M, pH 8.5) (Sigma-Aldrich, 15014) was injected for 7 min at 10 μl/min to block remaining active sites on the chip.

HEK293T cells transfected with DasherGFP (ATUM Biosciences, FPB-27-609), DasherGFP-3x-λN, EZH2, EED, or PTBP1 fused to a N-terminal HaloTag were prepared as described above. Cells were resuspended in 2 ml of 1×HBS-EP+ buffer (GE Healthcare, BR100669) supplemented with 1× Protease Inhibitor (Promega, G6521), 2.5 mM manganese chloride, 0.5 mM calcium chloride, 40 U of Turbo DNase (Ambion, AM2239), 40 μg of RNase A and 100 U of RNase T1 mix (Ambion, EN0551) and incubated on ice for 10 minutes. Cells were then sonicated (Branson Ultrasonics) for 30 seconds at 5 W (0.7 seconds on, 0.7 seconds off) then incubated at 37° C. for 10 minutes at 1100 RPM on a Thermomixer. Samples were then placed on ice for 2 minutes prior to centrifugation at 16,000×g for 2 minutes at 4° C. Clarified lysate was injected onto flow cells 2 and 4 of the chip for 60 seconds to allow Halo tagged proteins to covalently bind the chip surface, followed by a 1 second injection of 50 mM NaOH to clean the chip surface and remove non-covalently bound RNA, DNA and protein. Injections of lysate and NaOH pulses were continued until 10 RU of Halo tagged protein was covalently immobilized on the chip surface. Flow cells 1 and 3 of the chip were left blank to be used as reference surfaces.

RNA derived from the Maltose Binding Protein (MBP, 1-240 nucleotides), MBP fused to 5 copies of the BoxB aptamer (MBP-5x-BoxB), the A-repeat (260-1,002 nucleotides), or the E-repeat (11,963-12,705 nucleotides) of the Xist RNA were in vitro transcribed using the T7 RiboMAX Express Large Scale RNA Production System (Promega, P1320) after PCR amplification to incorporate a T7 promoter. In vitro transcribed RNA was diluted with water and 10×HBS-EP+ Buffer to a final concentration of 1.1 μM prior to heat denaturation at 70° C. for 2 minutes. 1M Magnesium chloride was added to a final concentration of 3.25 mM and allowed to cool to room temperature. RNA was then stored on ice or at 4° C. prior to injection over all four flow cells at 25° C. at 100 µl/min for 60 sec. The different concentrations of RNA were injected by the instrument in a randomized order. After injection ended, dissociation was monitored in each flow cell for 500 seconds. Regeneration of the sensor chip surface was performed by injecting 50 mM NaOH at 100 µl/min for 3 sec, waiting 180 seconds for the baseline to stabilize, then injecting a 1 second pulse of NaOH, waiting 240 second for the baseline to stabilize, and washing the injection needle.

Sensorgrams were processed with Biacore T200 Evaluation Software, (version 3.0). The y-axes were zeroed at the baseline for each cycle and x-axes were aligned at the injection start. We used the first 100 seconds of the dissociation curve for global fitting. Bulk refractive index changes and systematic deviations in sensorgrams were removed by subtracting the responses in reference flow cells (1 and 3) corresponding to the sample flow cells (2 and 4). The averaged sensorgrams for 0 nM RNA were then subtracted from sensorgrams for all other concentrations. After double referencing kinetic data and removing injection and pump spikes, the data were fit globally by non-linear regression to a simple 1:1 Langmuir binding model to determine association/dissociation rate constants ($k_a$, $k_d$), analyte binding capacity ($R_{max}$) and the equilibrium dissociation constant ($K_D$). Sensorgrams and 1:1 binding model curve fits were exported and plotted.

REFERENCES

Each of the following references is incorporated by reference in its entirety herein:

1. Margueron, R. & Reinberg, D. The Polycomb complex PRC2 and its mark in life. *Nature* 469, 343-349 (2011).
2. Simon, J. A. & Kingston, R. E. Mechanisms of polycomb gene silencing: knowns and unknowns. *Nat Rev Mol Cell Biol* 10, 697-708 (2009).
3. Khalil, A. M. et al. Many human large intergenic non-coding RNAs associate with chromatin-modifying complexes and affect gene expression. *Proc. Natl. Acad. Sci. U.S.A.* 106, (2009).
4. Guttman, M. et al. lincRNAs act in the circuitry controlling pluripotency and differentiation. *Nature* 477, 295-300 (2011).
5. Zhao, J., Sun, B. K., Erwin, J. A., Song, J. J. & Lee, J. T. Polycomb proteins targeted by a short repeat RNA to the mouse X chromosome. *Science* (80-.). 322, 750-756 (2008).
6. Zhao, J. et al. Genome-wide identification of polycomb-associated RNAs by RIP-seq. *Mol Cell* 40, 939-953 (2010).
7. Rinn, J. L. et al. Functional demarcation of active and silent chromatin domains in human HOX loci by noncoding RNAs. *Cell* 129, 1311-1323 (2007).
8. Rinn, J. L. & Chang, H. Y. Genome regulation by long noncoding RNAs. *Annu Rev Biochem* 81, 145-166 (2012).
9. Pandey, R. R. et al. Kcnq1ot1 antisense noncoding RNA mediates lineage-specific transcriptional silencing through chromatin-level regulation. *Mol. Cell* 32, 232-46 (2008).
10. Kaneko, S. et al. Phosphorylation of the PRC2 component Ezh2 is cell cycle-regulated and up-regulates its binding to ncRNA. *Genes Dev.* 24, 2615-20 (2010).
11. Woo, C. J. et al. Gene activation of SMN by selective disruption of lncRNA-mediated recruitment of PRC2 for the treatment of spinal muscular atrophy. *Proc. Natl. Acad. Sci. U.S.A* 114, E1509-E1518 (2017).
12. Yang, L. et al. ncRNA- and Pc2 methylation-dependent gene relocation between nuclear structures mediates gene activation programs. *Cell* 147, 773-788 (2011).
13. Beltran, M. et al. The interaction of PRC2 with RNA or chromatin is mutually antagonistic. *Genome Res.* 26, 896-907 (2016).
14. Kaneko, S., Son, J., Shen, S. S., Reinberg, D. & Bonasio, R. PRC2 binds active promoters and contacts nascent RNAs in embryonic stem cells. *Nat Struct Mol Biol* 20, 1258-1264 (2013).
15. Kaneko, S. et al. Interactions between JARID2 and noncoding RNAs regulate PRC2 recruitment to chromatin. *Mol Cell* 53, 290-300 (2014).
16. Spitale, R. C., Tsai, M.-C. & Chang, H. Y. RNA templating the epigenome: long noncoding RNAs as molecular scaffolds. *Epigenetics* 6, 539-43 (2011).
17. Lee, J. T. Lessons from X-chromosome inactivation: long ncRNA as guides and tethers to the epigenome. *Genes Dev* 23, 1831-1842 (2009).
18. Guttman, M. & Rinn, J. L. Modular regulatory principles of large non-coding RNAs. *Nature* 482, (2012).
19. Koziol, M. J. & Rinn, J. L. RNA traffic control of chromatin complexes. *Curr. Opin. Genet. Dev.* 20, 142-8 (2010).
20. Wang, D. et al. LncRNA MALAT1 enhances oncogenic activities of EZH2 in castration-resistant prostate cancer. *Oncotarget* 6, 41045-55 (2015).
21. Zovoilis, A., Cifuentes-Rojas, C., Chu, H.-P., Hernandez, A. J. & Lee, J. T. Destabilization of B2 RNA by EZH2 Activates the Stress Response. *Cell* 167, 1788-1802.e13 (2016).
22. Davidovich, C., Zheng, L., Goodrich, K. J. & Cech, T. R. Promiscuous RNA binding by Polycomb repressive complex 2. *Nat Struct Mol Biol* 20, 1250-1257 (2013).
23. Froberg, J. E., Yang, L. & Lee, J. T. Guided by RNAs: X-Inactivation as a Model for lncRNA Function. *J. Mol. Biol.* 425, 3698-3706 (2013).
24. Wutz, A. Gene silencing in X-chromosome inactivation: advances in understanding facultative heterochromatin formation. *Nat. Rev. Genet.* 12, 542-553 (2011).
25. Galupa, R. & Heard, E. X-chromosome inactivation: new insights into cis and trans regulation. *Curr. Opin. Genet. Dev.* 31, 57-66 (2015).
26. Cifuentes-Rojas, C., Hernandez, A. J., Sarma, K. & Lee, J. T. Regulatory Interactions between RNA and Polycomb Repressive Complex 2. *Mol Cell* 55, 171-185 (2014).
27. Wutz, A., Rasmussen, T. P. & Jaenisch, R. Chromosomal silencing and localization are mediated by different domains of Xist RNA. *Nat. Genet.* 30, 167-174 (2002).
28. Lee, J. T. Epigenetic regulation by long noncoding RNAs. *Science* (80-.). 338, 1435-1439 (2012).
29. Schoeftner, S. et al. Recruitment of PRC1 function at the initiation of X inactivation independent of PRC2 and silencing. *EMBO J.* 25, 3110-3122 (2006).
30. Kalantry, S. & Magnuson, T. The Polycomb group protein EED is dispensable for the initiation of random X-chromosome inactivation. *PLoS Genet* 2, e66 (2006).
31. Plath, K. et al. Role of histone H3 lysine 27 methylation in X inactivation. *Science* (80-.). 300, 131-135 (2003).
32. da Rocha, S. T. et al. Jarid2 Is Implicated in the Initial Xist-Induced Targeting of PRC2 to the Inactive X Chromosome. *Mol Cell* 53, 301-316 (2014).
33. McHugh, C. A. et al. The Xist lncRNA interacts directly with SHARP to silence transcription through HDAC3. *Nature* 521, 232-6 (2015).

34. Kohlmaier, A. et al. A chromosomal memory triggered by Xist regulates histone methylation in X inactivation. *PLoS Biol.* 2, E171 (2004).
35. Cerase, A. et al. Spatial separation of Xist RNA and polycomb proteins revealed by superresolution microscopy. *Proc Natl Acad Sci USA* 111, 2235-2240 (2014).
36. Chu, C. et al. Systematic discovery of Xist RNA binding proteins. *Cell* 161, 404-416 (2015).
37. Minajigi, A. et al. Chromosomes. A comprehensive Xist interactome reveals cohesin repulsion and an RNA-directed chromosome conformation. *Science (80-.).* 349, (2015).
38. Moindrot, B. et al. A Pooled shRNA Screen Identifies Rbm15, Spen, and Wtap as Factors Required for Xist RNA-Mediated Silencing. *Cell Rep.* (2015). doi:10.1016/j.celrep.2015.06.053
39. Monfort, A., Minin, G. Di, Postlmayr, A., Arieti, F. & Wutz, A. Identification of Spen as a Crucial Factor for Xist Function through Forward Genetic Screening in Haploid Embryonic Stem. *Cell Rep.* 1-8 (2015). doi:10.1016/j.celrep.2015.06.067
40. Portoso, M. et al. PRC2 is dispensable for HOTAIR ?mediated transcriptional repression. *EMBO J.* 36, 981-994 (2017).
41. Brockdorff, N. Noncoding RNA and Polycomb recruitment. *RNA* 19, 429-442 (2013).
42. Peritz, T. et al. Immunoprecipitation of mRNA-protein complexes. *Nat. Protoc.* 1, 577-580 (2006).
43. Keene, J. D., Komisarow, J. M. & Friedersdorf, M. B. RIP-Chip: the isolation and identification of mRNAs, microRNAs and protein components of ribonucleoprotein complexes from cell extracts. *Nat. Protoc.* 1, 302-307 (2006).
44. G Hendrickson, D., Kelley, D. R., Tenen, D., Bernstein, B. & Rinn, J. L. Widespread RNA binding by chromatin-associated proteins. *Genome Biol.* 17, 28 (2016).
45. Darnell, R. B. HITS-CLIP: panoramic views of protein-RNA regulation in living cells. *Wiley Interdiscip Rev RNA* 1, 266-286 (2010).
46. Konig, J. et al. iCLIP reveals the function of hnRNP particles in splicing at individual nucleotide resolution. *Nat Struct Mol Biol* 17, 909-915 (2010).
47. Hafner, M. et al. Transcriptome-wide identification of RNA-binding protein and microRNA target sites by PAR-CLIP. *Cell* 141, 129-141 (2010).
48. Ule, J. et al. CLIP Identifies Nova-Regulated RNA Networks in the Brain. *Science (80-.).* 302, 1212-1215 (2003).
49. Licatalosi, D. D. et al. HITS-CLIP yields genome-wide insights into brain alternative RNA processing. *Nature* 456, 464-469 (2008).
50. Davidovich, C. et al. Toward a Consensus on the Binding Specificity and Promiscuity of PRC2 for RNA. *Mol Cell* 57, 552-558 (2015).
51. Wang, X. et al. Targeting of Polycomb Repressive Complex 2 to RNA by Short Repeats of Consecutive Guanines. *Mol. Cell* 65, 1056-1067.e5 (2017).
52. Mili, S. & Steitz, J. A. Evidence for reassociation of RNA-binding proteins after cell lysis: implications for the interpretation of immunoprecipitation analyses. *RNA* 10, 1692-1694 (2004).
53. Khalil, A. M. et al. Many human large intergenic noncoding RNAs associate with chromatin-modifying complexes and affect gene expression. *Proc Natl Acad Sci USA* 106, 11667-11672 (2009).
54. Guttman, M. et al. LincRNAs act in the circuitry controlling pluripotency and differentiation. *Nature* 477, (2011).
55. Kanhere, A. et al. Short RNAs are transcribed from repressed polycomb target genes and interact with polycomb repressive complex-2. *Mol. Cell* 38, 675-88 (2010).
56. Mohammad, F. et al. Kcnq1ot1/Lit1 noncoding RNA mediates transcriptional silencingby targeting to the perinucleolar region. *Mol. Cell. Biol.* 28, 3713-28 (2008).
57. Terranova, R. et al. Polycomb group proteins Ezh2 and Rnf2 direct genomic contraction and imprinted repression in early mouse embryos. *Dev. Cell* 15, 668-79 (2008).
58. Wu, H.-A. & Bernstein, E. Partners in Imprinting: Noncoding RNA and Polycomb Group Proteins. *Dev. Cell* 15, 637-638 (2008).
59. Tichon, A. et al. A conserved abundant cytoplasmic long noncoding RNA modulates repression by *Pumilio* proteins in human cells. *Nat. Commun.* 7, 12209 (2016).
60. Lee, S. et al. Noncoding RNA NORAD Regulates Genomic Stability by Sequestering PUMILIO Proteins. *Cell* 164, 69-80 (2016).
61. Ule, J. et al. CLIP identifies Nova-regulated RNA networks in the brain. *Science (80-.).* 302, 1212-1215 (2003).
62. Yeo, G. W. et al. An RNA code for the FOX2 splicing regulator revealed by mapping RNA-protein interactions in stem cells. *Nat. Struct. Mol. Biol.* 16, 130-137 (2009).
63. Sundararaman, B. et al. Resources for the Comprehensive Discovery of Functional RNA Elements. *Mol. Cell* 61, 903-913 (2016).
64. Ray, D. et al. Rapid and systematic analysis of the RNA recognition specificities of RNA-binding proteins. *Nat. Biotechnol.* 27, 667-670 (2009).
65. Ozdilek, B. A. et al. Intrinsically disordered RGG/RG domains mediate degenerate specificity in RNA binding. *Nucleic Acids Res.* (2017). doi:10.1093/nar/gkx460
66. Lu, Z. et al. RNA Duplex Map in Living Cells Reveals Higher-Order Transcriptome Structure. *Cell* 165, 1267-1279 (2016).
67. Chen, C.-K. et al. Xist recruits the X chromosome to the nuclear lamina to enable chromosome-wide silencing. *Science (80-.).* 354, (2016).
68. Cirillo, D. et al. Quantitative predictions of protein interactions with long noncoding RNAs. *Nat. Methods* 14, 5-6 (2016).
69. Tsai, M. C. et al. Long noncoding RNA as modular scaffold of histone modification complexes. *Science (80-.).* 329, 689-693 (2010).
70. Derrien, T. et al. The GENCODE v7 catalog of human long noncoding RNAs: analysis of their gene structure, evolution, and expression. *Genome Res* 22, 1775-1789 (2012).
71. Huarte, M. et al. A large intergenic noncoding RNA induced by p53 mediates global gene repression in the p53 response. *Cell* 142, 409-419 (2010).
72. Yang, Y. W. et al. Essential role of lncRNA binding for WDR5 maintenance of active chromatin and embryonic stem cell pluripotency. *Elife* 3, e02046 (2014).
73. Kwon, S. C. et al. The RNA-binding protein repertoire of embryonic stem cells. *Nat Struct Mol Biol* 20, 1122-1130 (2013).
74. Castello, A. et al. Insights into RNA biology from an atlas of mammalian mRNA-binding proteins. *Cell* 149, 1393-1406 (2012).
75. Castello, A., Hentze, M. W. & Preiss, T. Metabolic Enzymes Enjoying New Partnerships as RNA-Binding Proteins. *Trends Endocrinol. Metab.* 26, 746-57 (2015).

76. Kundu, S. et al. Polycomb Repressive Complex 1 Generates Discrete Compacted Domains that Change during Differentiation. *Mol. Cell* 65, 432-446.e5 (2017).
77. Cheutin, T. & Cavalli, G. Polycomb silencing: from linear chromatin domains to 3D chromosome folding. *Curr Opin Genet Dev* 25C, 30-37 (2014).
78. Bantignies, F. et al. Polycomb-Dependent Regulatory Contacts between Distant Hox Loci in *Drosophila. Cell* 144, 214-226 (2011).
79. Engreitz, J. M. et al. The Xist lncRNA exploits three-dimensional genome architecture to spread across the X chromosome. *Science* (80-.). 341, (2013).
80. Van Nostrand, E. L. et al. Robust transcriptome-wide discovery of RNA-binding protein binding sites with enhanced CLIP (eCLIP). *Nat. Methods* (2016). doi: 10.1038/nmeth.3810
81. Shishkin, A. A. et al. Simultaneous generation of many RNA-seq libraries in a single reaction. *Nat. Methods* 12, 323-5 (2015).
82. Bolger, A. M., Lohse, M. & Usadel, B. Trimmomatic: a flexible trimmer for Illumina sequence data. *Bioinformatics* 30, 2114-2120 (2014).
83. Xu, H. et al. FastUniq: A Fast De Novo Duplicates Removal Tool for Paired Short Reads. *PLoS One* 7, e52249 (2012).
84. Lassmann, T., Hayashizaki, Y. & Daub, C. O. Tag-Dust—a program to eliminate artifacts from next generation sequencing data. *Bioinformatics* 25, 2839-2840 (2009).
85. Dobin, A. et al. STAR: ultrafast universal RNA-seq aligner. *Bioinformatics* 29, 15-21 (2013).

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods, compositions, kits, and uses described herein without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one of skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Wherever a method of using a composition (e.g., a method of detecting an association between a query protein and a target moiety) is disclosed herein, the corresponding composition for use is also expressly contemplated. For example, for the disclosure of a method of detecting an association between a query protein and a target moiety, comprising the a query protein, the corresponding query protein for use in detecting an association between a query protein and a target moiety is also contemplated.

While various aspects and embodiments have been disclosed herein, other aspects and embodiments will be apparent to those of skill in the art. The various aspects and embodiments disclosed herein are for purposes of illustration and are not intended to be limiting, with the true scope and spirit being indicated by the following claims.

What is claimed is:

1. A method of detecting an association between a query protein and a target moiety, the method comprising:
   providing the query protein comprising a tag and a barcode; wherein
      the barcode comprises a polynucleotide comprising a coding sequence of the query protein;
   contacting the query protein with a composition comprising the target moiety, whereby the target moiety associates with the query protein;
   applying a crosslinking agent or force to the query protein and the composition, thereby crosslinking the query protein to the target moiety associated therewith;
   covalently binding the tag to a substrate, thereby covalently immobilizing the query protein and crosslinked target moiety on the substrate;
   washing the immobilized query protein and crosslinked target moiety under denaturing conditions, wherein the query protein remains immobilized on the substrate; and
   detecting the target moiety associated with the query protein after said washing.

2. The method of claim 1, wherein the method is performed in multiplex, comprising two or more different query proteins, each comprising a different barcode.

3. The method of claim 1, wherein the barcode comprises a covalent polypeptide tag fused to the polynucleotide, and wherein said covalent polypeptide tag is covalently bound to a counterpart polypeptide sequence on the query protein.

4. The method of claim 3, wherein the counterpart polypeptide sequence is disposed at an N terminus of the query protein.

5. The method of claim 3, wherein the covalent polypeptide tag and counterpart polypeptide sequence comprise a Spytag and SpyCatcher; or Isopeptag and pilin-C; or SnoopTag and SnoopC-atcher; or DogTag and SnoopTagJr; or SdyTag and SdyCatcher.

6. The method of claim 3, wherein providing the query protein comprises:
   fusing the covalent polypeptide tag to the polynucleotide encoding the query protein, wherein the counterpart polypeptide sequence is disposed at an N-terminal portion of the query protein;
   transcribing the polynucleotide in vitro, thereby producing the query protein comprising the counterpart polypeptide sequence disposed at the N-terminal portion and further comprising the tag; and
   covalently binding the polypeptide tag to the counterpart polypeptide sequence, thereby making the query protein comprising the tag and the barcode.

7. The method of claim 1, wherein the contacting and applying are in vivo.

8. The method of claim 7, wherein providing the query protein comprising the tag comprises expressing a nucleic acid encoding the query protein comprising the tag in vivo.

9. The method of claim 8, further comprising administering a vector comprising the nucleic acid encoding the query protein comprising the tag to a cell.

10. The method of claim 1, wherein:
   the tag comprises a haloalkane dehalogenase and the substrate comprises a haloalkane resin; or
   the tag comprises a DNA methyltransferase and the substrate comprises a benzylguanine resin; or
   the tag comprises a DNA methyltransferase and the substrate comprises a benzylcytosine resin; or
   the tag comprises an isopeptag and the substrate comprises a pilin-C protein; or
   the tag comprises a SpyTag and the substrate comprises a SpyCatcher protein; or
   the tag comprises SnoopTag and the substrate comprises a SnoopCatcher protein; or
   the tag comprises DogTag and the substrate comprises SnoopTagJr; or
   the tag comprises SdyTag and the substrate comprises SdyCatcher; or
   the tag comprises $Cpe0147_{565-587}$ and the substrate comprises $Cpe0147_{439-563}$.

11. The method of claim 1, wherein the target moiety is a protein, a nucleic acid, or a protein-nucleic acid complex.

12. The method of claim 1, wherein the target moiety comprises an RNA, and wherein the washing is at a temperature effective to fragment RNA, thereby fragmenting the target moiety.

13. The method of claim 1, wherein the crosslinking agent or force comprises ultraviolet radiation, or an amine-to-amine crosslinker, or a sulfhydryl-to-sulfhydryl crosslinker, or an aryl-azide, or a diazirine.

14. The method of claim 1, wherein covalently binding the tag to the substrate and washing are performed in a single container.

15. A composition comprising
   a query protein comprising a tag and a barcode; wherein
      the barcode comprises a polynucleotide comprising a coding sequence of the query protein;
   a substrate, wherein the tag is covalently bound to the substrate;
   a target moiety crosslinked to the query protein;
   wherein the composition is under denaturing conditions.

16. The composition of claim 15, wherein the barcode comprises a covalent polypeptide tag fused to the polynucleotide, and wherein said covalent polypeptide tag is covalently bound to a counterpart polypeptide sequence on the query protein.

* * * * *

```
                          SEQUENCE LISTING

<160> NUMBER OF SEQ ID NOS: 5

<210> SEQ ID NO 1
<211> LENGTH: 16
<212> TYPE: PRT
<213> ORGANISM: Artificial Sequence
<220> FEATURE:
<223> OTHER INFORMATION: Synthetic; isopeptag

<400> SEQUENCE: 1

Thr Asp Lys Asp Met Thr Ile Thr Phe Thr Asn Lys Lys Asp Ala Glu
1               5                   10                  15

<210> SEQ ID NO 2
<211> LENGTH: 13
<212> TYPE: PRT
<213> ORGANISM: Artificial Sequence
<220> FEATURE:
<223> OTHER INFORMATION: Synthetic; SpyTag

<400> SEQUENCE: 2

Ala His Ile Val Met Val Asp Ala Tyr Lys Pro Thr Lys
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic; SnoopTag

<400> SEQUENCE: 3

Lys Leu Gly Asp Ile Glu Phe Ile Lys Val Asn Lys
1               5                   10

<210> SEQ ID NO 4
<211> LENGTH: 23
<212> TYPE: PRT
<213> ORGANISM: Artificial Sequence
<220> FEATURE:
<223> OTHER INFORMATION: Synthetic; DogTag

<400> SEQUENCE: 4

Asp Ile Pro Ala Thr Tyr Glu Phe Thr Asp Gly Lys His Tyr Ile Thr
1               5                   10                  15

Asn Glu Pro Ile Pro Pro Lys
            20

<210> SEQ ID NO 5
<211> LENGTH: 13
<212> TYPE: PRT
<213> ORGANISM: Artificial Sequence
<220> FEATURE:
<223> OTHER INFORMATION: Synthetic; SdyTag

<400> SEQUENCE: 5

Asp Pro Ile Val Met Ile Asp Asn Asp Lys Pro Ile Thr
1               5                   10
```